(12) United States Patent
Cameron

(10) Patent No.: US 11,768,594 B2
(45) Date of Patent: Sep. 26, 2023

(54) SYSTEM AND METHOD FOR VIRTUAL REALITY BASED HUMAN BIOLOGICAL METRICS COLLECTION AND STIMULUS PRESENTATION

(71) Applicant: Electric Puppets Incorporated, Halifax (CA)

(72) Inventor: Ryan Cameron, Chester (CA)

(73) Assignee: Electric Puppets Incorporated, Halifax (CA)

(*) Notice: Subject to any disclaimer, the term of this patent is extended or adjusted under 35 U.S.C. 154(b) by 0 days.

(21) Appl. No.: 17/780,417

(22) PCT Filed: Nov. 26, 2020

(86) PCT No.: PCT/CA2020/051620
§ 371 (c)(1),
(2) Date: May 26, 2022

(87) PCT Pub. No.: WO2021/102577
PCT Pub. Date: Jun. 3, 2021

(65) Prior Publication Data
US 2023/0004284 A1 Jan. 5, 2023

Related U.S. Application Data

(60) Provisional application No. 62/942,000, filed on Nov. 29, 2019.

(51) Int. Cl.
*G06F 3/0484* (2022.01)
*G06F 3/04847* (2022.01)
(Continued)

(52) U.S. Cl.
CPC .......... *G06F 3/04847* (2013.01); *A61B 3/005* (2013.01); *A61B 3/032* (2013.01);
(Continued)

(58) Field of Classification Search
CPC ...... G06F 3/04847; G06F 3/012; G06F 3/013; G06F 3/04842; G06F 3/011;
(Continued)

(56) References Cited

U.S. PATENT DOCUMENTS 6,047,259 A * 4/2000 Campbell .............. G16H 15/00
705/2
6,386,706 B1 5/2002 McClure et al.
(Continued)

FOREIGN PATENT DOCUMENTS

WO 2017115366 A1 7/2017
WO 2018022521 A1 2/2018
(Continued)

OTHER PUBLICATIONS

International Search Report and Written Opinion dated Mar. 3, 2021 in International Patent Application No. PCT/CA2020/051620 (20 pages).

*Primary Examiner* — Jordany Nunez
(74) *Attorney, Agent, or Firm* — BERESKIN & PARR LLP/ S.E.N.C.R.L. s.r.l; Tonino Rosario Orsi

(57) ABSTRACT

A method of updating a protocol for a Virtual Reality (VR) medical test via a user device having a processor, the VR medical test being performed on a subject via a VR device worn by the subject, wherein the method is performed by the processor and the method comprises: displaying GUI elements associated with the protocol on the user device, the GUI elements having user adjustable settings for modifying a functioning of the VR medical test; receiving a selection input from the user device corresponding to a selection of the GUI elements; receiving a setting input from the user device that corresponds to the selected GUI elements; modifying the user adjustable setting for each of the selected GUI elements according to the corresponding setting input; and
(Continued)

updating the protocol based on the user adjustable setting for each of the selected GUI elements and operations associated with the VR device.

23 Claims, 35 Drawing Sheets

(51) Int. Cl.
*H04L 67/131* (2022.01)
*A61B 3/00* (2006.01)
*A61B 3/032* (2006.01)
*G06F 3/01* (2006.01)
*H04N 13/344* (2018.01)
*H04N 23/62* (2023.01)
*G06F 3/04842* (2022.01)

(52) U.S. Cl.
CPC .............. *G06F 3/012* (2013.01); *G06F 3/013* (2013.01); *H04L 67/131* (2022.05); *G06F 3/04842* (2013.01); *H04N 13/344* (2018.05); *H04N 23/62* (2023.01)

(58) Field of Classification Search
CPC ..... G06F 3/04815; A61B 3/005; A61B 3/032; A61B 5/6803; A61B 5/6814; A61B 2562/0219; A61B 5/743; A61B 3/113; A61B 5/0077; A61B 5/1103; A61B 5/1123; A61B 5/1128; A61B 5/291; A61B 5/369; H04L 67/131; H04N 13/344; H04N 23/62; G16H 40/63; G16H 50/20
See application file for complete search history.

(56) References Cited

U.S. PATENT DOCUMENTS

| | | | | |
|---|---|---|---|---|
| 7,614,745 | B2* | 11/2009 | Waldorf | A61B 3/113 351/209 |
| 8,055,324 | B1* | 11/2011 | Parker | A61B 8/465 600/407 |
| 8,967,809 | B2* | 3/2015 | Kirschen | A61B 3/032 351/239 |
| 9,514,275 | B2* | 12/2016 | Profio | G16H 50/20 |
| 10,026,328 | B2* | 7/2018 | Knoche | G09B 7/00 |
| 10,209,773 | B2* | 2/2019 | Khaderi | G02B 27/0172 |
| 10,332,315 | B2 | 6/2019 | Samec et al. | |
| 10,345,590 | B2* | 7/2019 | Samec | A61B 8/461 |
| 10,354,261 | B2 | 7/2019 | Rogers et al. | |
| 10,413,172 | B2* | 9/2019 | Jensen | G10L 15/22 |
| 10,437,062 | B2 | 10/2019 | Samec et al. | |
| 10,460,497 | B1 | 10/2019 | Steinbach et al. | |
| 10,481,402 | B1* | 11/2019 | Abou Shousha | G02B 27/0179 |
| 10,485,421 | B1* | 11/2019 | Abou Shousha | A61B 3/113 |
| 10,545,341 | B2* | 1/2020 | Samec | G02B 27/0093 |
| 10,599,657 | B1* | 3/2020 | Balogh | G06F 16/90335 |
| 11,510,650 | B2* | 11/2022 | Yoneyama | A61B 8/5261 |
| 2004/0141152 | A1* | 7/2004 | Marino | A61B 3/032 351/222 |
| 2006/0079842 | A1* | 4/2006 | Small | A61M 5/14546 600/432 |
| 2009/0115965 | A1* | 5/2009 | Waldorf | G06V 20/597 351/210 |
| 2009/0115966 | A1* | 5/2009 | Waldorf | A61B 3/112 351/210 |
| 2009/0138280 | A1* | 5/2009 | Morita | G16H 30/40 705/3 |
| 2011/0060219 | A1* | 3/2011 | Small | A61M 5/14546 600/432 |
| 2012/0075586 | A1* | 3/2012 | Kirschen | A61B 3/028 351/239 |
| 2012/0141970 | A1* | 6/2012 | Pompilio | G06F 9/453 434/362 |
| 2014/0128763 | A1* | 5/2014 | Fadem | A61B 5/38 600/544 |
| 2014/0364720 | A1* | 12/2014 | Darrow | A61B 5/055 600/410 |
| 2015/0150455 | A9* | 6/2015 | Epley | A61B 5/1104 600/559 |
| 2016/0000401 | A1* | 1/2016 | Mienkina | G16H 50/30 600/443 |
| 2016/0092347 | A1* | 3/2016 | Edwards | G06F 11/3684 717/125 |
| 2017/0000329 | A1* | 1/2017 | Samec | G02B 27/0172 |
| 2017/0290504 | A1* | 10/2017 | Khaderi | A61B 3/0091 |
| 2018/0008141 | A1 | 1/2018 | Krueger | |
| 2018/0064330 | A1* | 3/2018 | Markus | A61B 3/0075 |
| 2018/0110409 | A1 | 4/2018 | Tsapakis | |
| 2018/0121608 | A1 | 5/2018 | Gross et al. | |
| 2018/0211728 | A1* | 7/2018 | Chillemi | A61B 5/7435 |
| 2018/0300433 | A1 | 10/2018 | Maxam et al. | |
| 2019/0150727 | A1 | 3/2019 | Blaha et al. | |
| 2019/0175011 | A1* | 6/2019 | Jensen | G10L 15/22 |
| 2019/0239850 | A1* | 8/2019 | Dalvin | A61B 8/4245 |
| 2019/0274610 | A1 | 9/2019 | Wang et al. | |
| 2019/0298166 | A1 | 10/2019 | Smith et al. | |
| 2019/0303110 | A1 | 10/2019 | Brude | |
| 2019/0362850 | A1* | 11/2019 | Chillemi | A61B 5/743 |
| 2019/0362851 | A1* | 11/2019 | Chillemi | G16H 40/63 |
| 2019/0379869 | A1* | 12/2019 | Abou Shousha | A61B 3/0025 |
| 2019/0391398 | A1* | 12/2019 | Abou Shousha | A61B 3/024 |
| 2020/0221990 | A1* | 7/2020 | Chiofolo | G06N 3/02 |
| 2021/0112226 | A1* | 4/2021 | Abou Shousha | G06V 10/764 |
| 2021/0290051 | A1* | 9/2021 | Tang | A61B 3/022 |
| 2021/0312833 | A1* | 10/2021 | Betteridge | G16H 50/20 |
| 2022/0014720 | A1* | 1/2022 | Abou Shousha | A61B 3/085 |
| 2022/0171456 | A1* | 6/2022 | Siddiqi | G06F 3/011 |
| 2023/0040764 | A1* | 2/2023 | Govari | B06B 1/0284 |

FOREIGN PATENT DOCUMENTS

| | | |
|---|---|---|
| WO | 2018191731 A1 | 10/2018 |
| WO | 2019028268 A1 | 2/2019 |
| WO | 2019036038 A1 | 2/2019 |
| WO | 2019036051 A1 | 2/2019 |
| WO | 2019071166 A1 | 4/2019 |
| WO | 2019157448 A1 | 8/2019 |
| WO | 2019173765 A1 | 9/2019 |
| WO | 2020014237 A1 | 1/2020 |
| WO | 2020044124 A1 | 3/2020 |
| WO | 2020084351 A1 | 4/2020 |

* cited by examiner

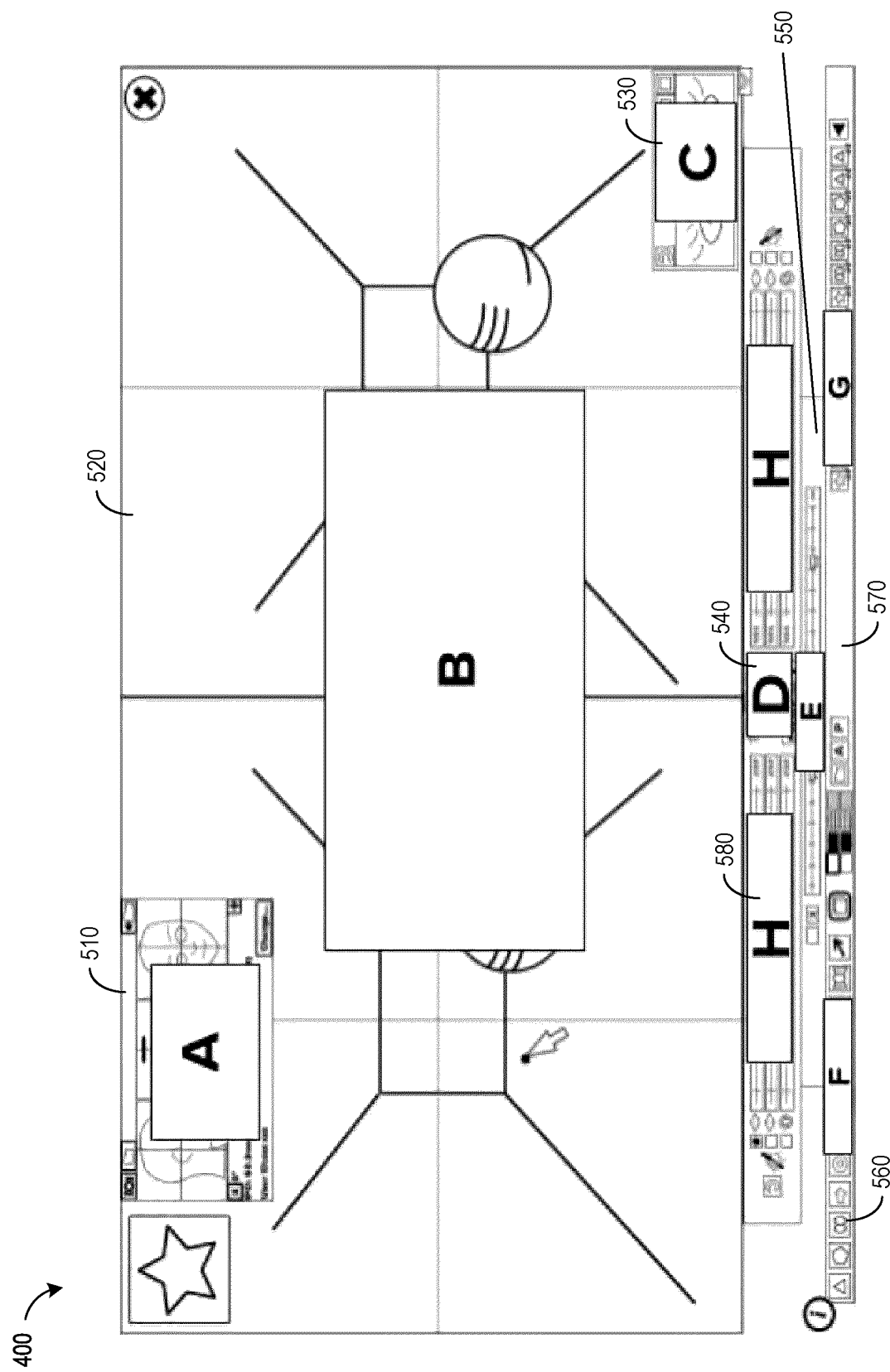

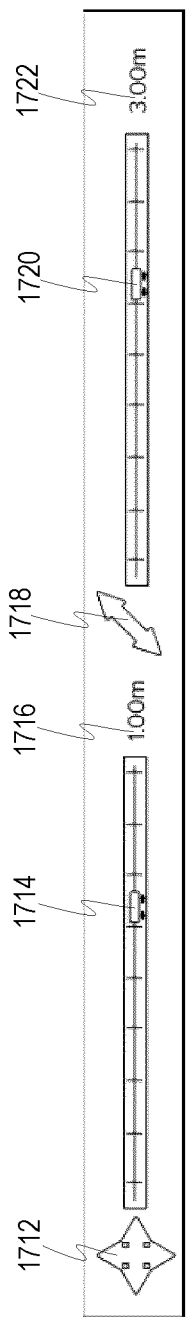
FIG. 17A
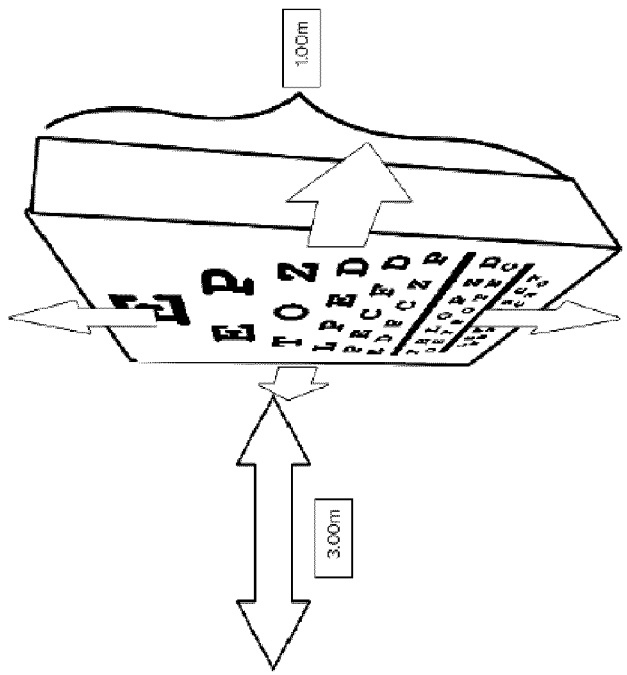
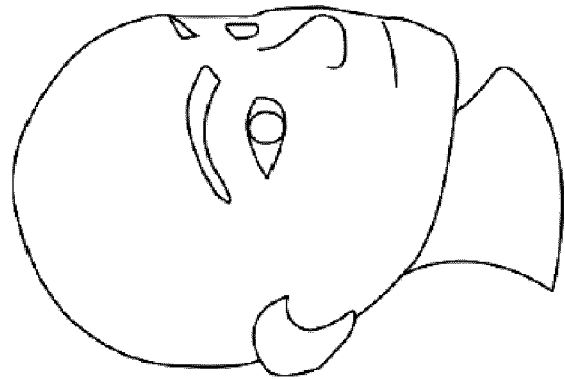
FIG. 17B

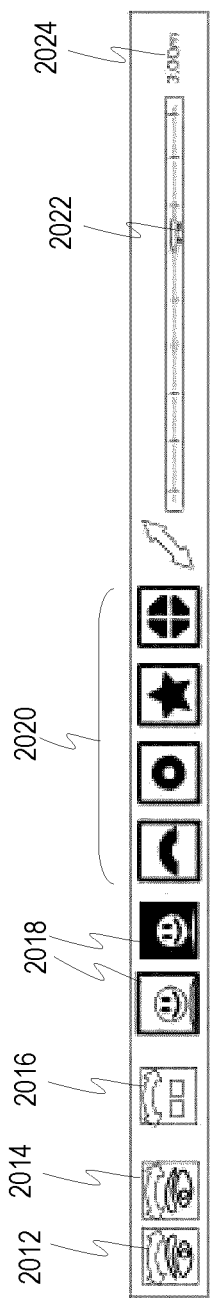
FIG. 20A
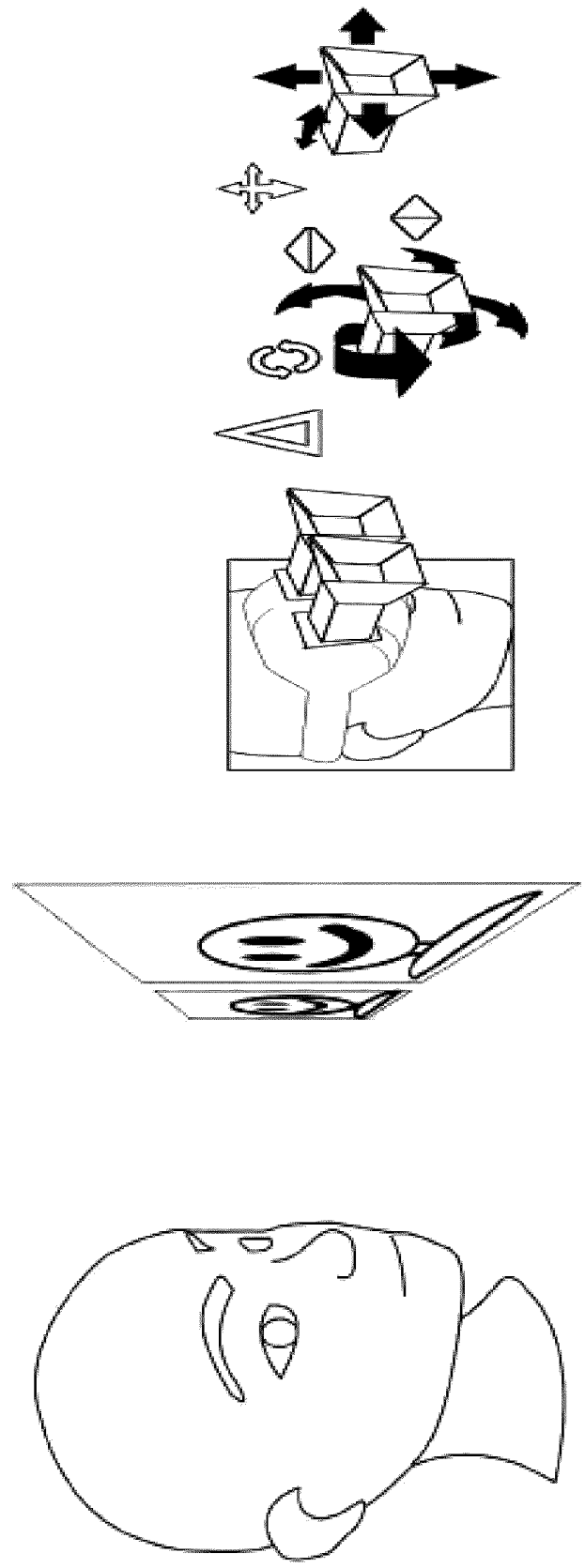
FIG. 20C
FIG. 20B

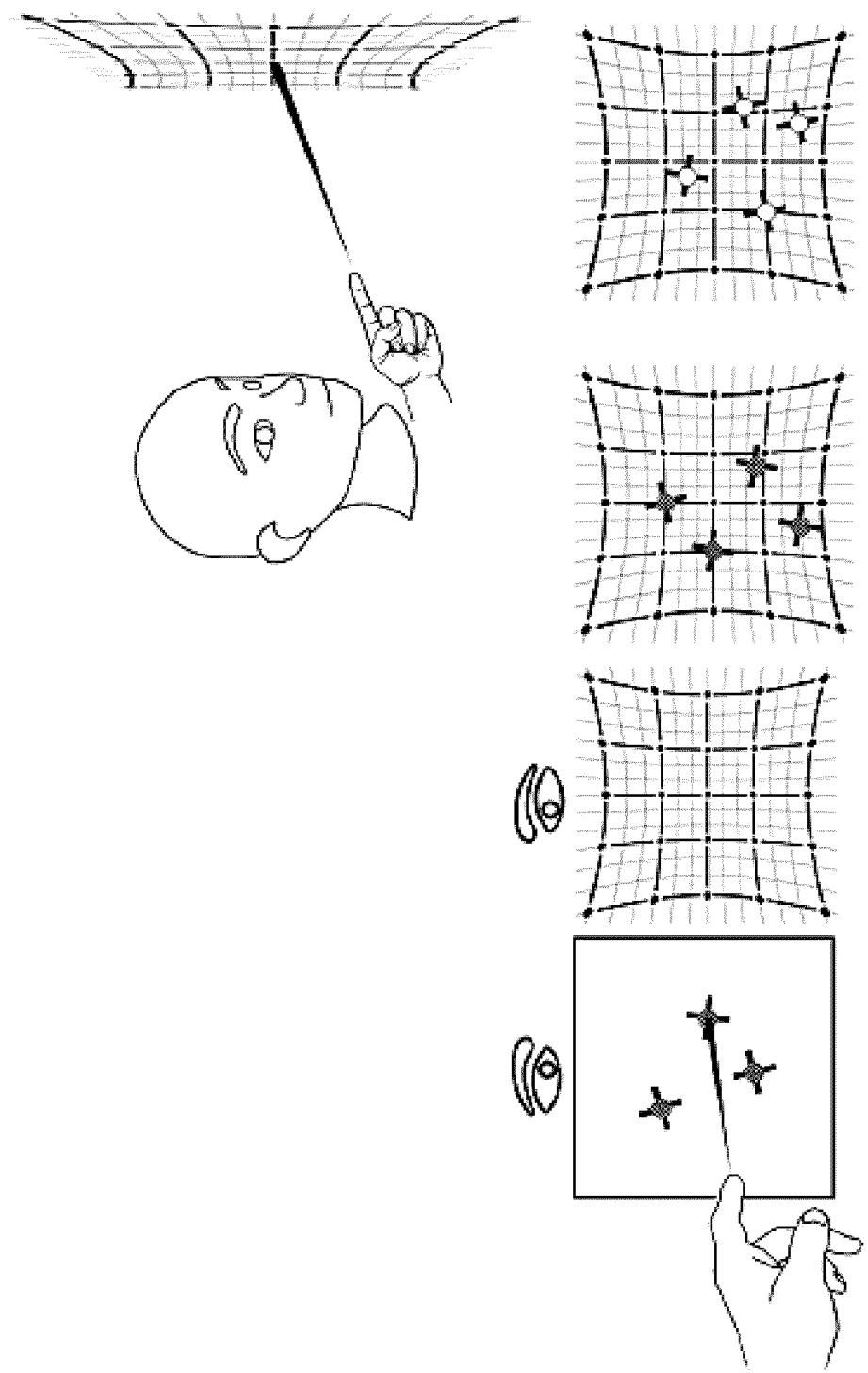

SYSTEM AND METHOD FOR VIRTUAL REALITY BASED HUMAN BIOLOGICAL METRICS COLLECTION AND STIMULUS PRESENTATION

CROSS-REFERENCE

This application is a 35 USC § 371 national stage entry of International Patent Application No. PCT/CA2020/051620, filed Nov. 26, 2020, entitled "SYSTEM AND METHOD FOR VIRTUAL REALITY BASED HUMAN BIOLOGICAL METRICS COLLECTION AND STIMULUS PRESENTATION", which claims the benefit of U.S. Provisional Patent Application No. 62/942,000, filed Nov. 29, 2019, and the entire contents of each of which are hereby incorporated by reference.

FIELD

Various embodiments are described herein that relate to generating and delivering virtual reality based medical testing systems and methods.

BACKGROUND

The following paragraphs are provided by way of background to the present disclosure. However, the following paragraphs are not an admission that anything discussed therein is prior art or part of the knowledge of persons skilled in the art.

A portion of every eye exam requires subjective feedback from subjects (e.g., patients) to determine the level of functioning of the visual system. The feedback includes, for example, what letter does the subject see, or whether the subject can tell if any shapes stick out of a book. These become more challenging in a pediatric ophthalmology service or in clinics specializing in disorders of binocular vision. Current technology is antiquated, expensive, and time consuming. The market has not seen any substantial advances in several decades.

Virtual reality (VR) has advanced over the years to the point that it is being used to simulate more and more real-life experiences. However, combining VR technology and clinical testing presents challenges, both for the developer (i.e., the person developing a system for use with a VR device) and for the user (i.e., the person administering the clinical test on a VR device).

There is a need for a system and method for the generation and delivery of virtual reality based medical (e.g., visual) testing that addresses the challenges and/or shortcomings described above.

SUMMARY OF VARIOUS EMBODIMENTS

Various embodiments of a system and method for virtual reality based human biological metrics collection and stimulus presentation, and computer products for use therewith, are provided according to the teachings herein.

In one aspect, in accordance with the teachings herein, there is provided a method of updating a protocol for a Virtual Reality (VR) medical test via a user device having at least one processor, the VR medical test being performed on a subject via a VR device worn by the subject, wherein the method is performed by the at least one processor and the method comprises: displaying GUI elements associated with the protocol on the user device, the GUI elements having user adjustable settings for modifying a functioning of the VR medical test; receiving at least one selection input from the user device corresponding to a selection of at least one of the GUI elements; receiving at least one setting input from the user device that corresponds to the selection of the at least one selected GUI elements; modifying the user adjustable setting for each of the at least one selected GUI elements according to the corresponding at least one setting input; and updating the protocol based at least on the user adjustable setting for each of the at least one selected GUI elements and the plurality of operations associated with the VR device.

In at least one embodiment, the method comprises determining at least one of the plurality of operations to be executed on the VR device during the VR medical test based at least in part on the at least one selection input and the at least one setting input.

In at least one embodiment, the VR medical test is a VR vision test.

In at least one embodiment, the GUI elements comprise at least one of one or more VR methods, one or more VR features, or one or more VR controls.

In at least one embodiment, the one or more VR methods comprise at least one of: left eye tracking, right eye tracking, head rotation tracking, or laser pointer placement.

In at least one embodiment, the one or more VR features comprise at least one of: a subject data area, a subject VR view, or an eye camera area.

In at least one embodiment, the one or more VR controls comprise at least one of: at least one state button, at least one toggle button, at least one slider, and at least one VR controller icon.

In at least one embodiment, determining at least one of the plurality of operations comprises organizing a VR visual stimulus including determining an intensity, one or more colors, and one or more shapes of at least one object in the VR visual stimulus.

In at least one embodiment, determining at least one of the plurality of operations comprises filtering a visual stimulus with specific wavelengths of color at varying intensities to obtain data from the subject during VR testing relating to color sensitivity.

In at least one embodiment, determining at least one of the plurality of operations comprises at least one of altering an orientation and/or position of an object in the visual stimulus, and displaying the visual stimulus to one or both eyes of the subject.

In at least one embodiment, determining at least one of the plurality of operations comprises representing and recording each axis of rotation of the subject's head relative to a direction of presentation of the VR visual stimulus to the subject.

In at least one embodiment, the at least one of the GUI elements comprises a user controllable setting for allowing the user to set at least one of a distance, an orientation, and an intensity of a visual VR stimulus using the user device.

In at least one embodiment, the at least one of the GUI elements comprises a sensor control and the user adjustable setting therefor allows the user to select when the sensor is used to obtain measurements of the subject during testing.

In at least one embodiment, the method comprises receiving user input for the sensor control for controlling at least one of an eye tracker, a camera, a force feedback sensor, an EEG sensor, and a motion tracker.

In at least one embodiment, the functionality of the selection comprises at least one of displacement, rotation, or color filtering.

In at least one embodiment, the method comprises: receiving at least one recording input from the user device corresponding to recording instructions associated with recording data during execution of the VR medical test on the VR device.

In at least one embodiment, the recording instructions comprise at least one of tracking one or both subject eyes, recording a position of the subject's head, recording a rotation of the subject's head, and recording a selection made by the subject through a hand gesture or interaction with a VR controller.

In at least one embodiment, the VR vision test is a Bagolini Striated Lens VR test and the method comprises receiving user input to adjust settings for GUI elements associated with a gradations input, a distance input, and a rotation input.

In at least one embodiment, the VR vision test is a Frisby Stereopsis VR test and the method comprises receiving user input to adjust settings for GUI elements associated with a stereopsis stimulus selection input and a distance input.

In at least one embodiment, the VR vision test is a Synoptophore VR test and the method further comprises receiving user input to adjust settings for GUI elements associated with a reverse eye stimulus input, a swap eye stimulus input, an actual stimulus input, and a stimulus distance input.

In at least one embodiment, the VR vision test is a Lees Screen VR test and the method further comprises receiving user input to adjust settings for GUI elements associated with a show close-up stimulus input, a show distant stimulus input, and a show eye orientation input.

In another aspect, in accordance with the teachings herein, there is provided a system for allowing a user to update a protocol for a Virtual Reality (VR) medical test to be performed on a subject via a VR device worn by the subject, wherein the system comprises: a display that shows a graphical user interface having GUI elements representing settings for the protocol; an input device that is adapted to receive user inputs from the user for at least one of the GUI elements; a memory unit that is adapted to store a protocol data file for the updated protocol; and a processor unit that is operatively coupled to the display, the input device and the memory unit, the processor unit having at least one processor, the memory unit comprising a non-transient computer-readable storage medium having stored thereon computer-executable instructions for execution by the processor unit to perform the method of updating a protocol for a Virtual Reality (VR) medical test in accordance with the teachings herein.

In another aspect, in accordance with the teachings herein, there is provided a computer readable medium comprising a plurality of instructions that are executable on a processor of a system for adapting the system to implement a method to allow a user to update a protocol for a Virtual Reality (VR) medical test to be performed on a subject via a VR device worn by the subject, wherein the method is defined in accordance with the teachings herein In another aspect, in accordance with the teachings herein, there is provided a method for generating and displaying a graphical user interface for a Virtual Reality (VR) medical test via a user device having at least one processor, the VR medical test being performed on a subject via a VR device worn by the subject, wherein the method is performed by the at least one processor and the method comprises: displaying a subject viewing area that comprises a view of the subject during testing or during playback of a recorded test; displaying a camera settings area that comprises camera inputs for receiving user input for modifying images that are displayed in the subject viewing area; and displaying a test-specific UI area that comprises test parameters that indicate settings for controlling different aspects of VR visual stimuli that are displayed to the subject via the VR device during testing.

In at least one embodiment, the method comprises showing real-time data about the subject during testing in the subject viewing area.

In at least one embodiment, the subject viewing area comprises an eye camera area and the method comprises displaying a video of one or both eyes along with eye tracker data comprising pupil diameter of the subject in the eye camera area during testing or when playing back stored results of a previous test.

In at least one embodiment, the method comprises displaying a subject VR view that shows what is displayed by the VR device to the subject during testing.

In at least one embodiment, the method comprises: displaying main camera settings in the camera settings area; receiving user input associated with the main camera settings for a desired view; and displaying the desired view in the subject viewing area.

In at least one embodiment, the method comprises displaying the camera settings area to show camera settings sliders that control at least one of eye blurring, eye rotation, color filter, or displacement during VR testing.

In at least one embodiment, the method comprises changing a display of the test inputs shown in the test-specific UI area due to user input from the user device when the user selects a particular VR medical test.

In at least one embodiment, the method comprises using the graphical user interface to display at least one of a Bagolini Striated Lens VR test, a Frisby Stereopsis VR test, a Synoptophore VR test, and a Lees Screen VR test.

In another aspect, in accordance with the teachings herein, there is provided a system for generating and displaying a graphical user interface for a Virtual Reality (VR) medical test to allow a user to perform the VR medical test on a subject via a VR device worn by the subject, wherein the system comprises: a display for showing the graphical user interface; an input device that is adapted to receive user inputs; a memory unit that is adapted to store a protocol data file having values for settings for the VR medical test; and a processor unit that is operatively coupled to the display, the input device, and the memory unit, the processor unit having at least one processor that is configured to perform a method for generating and displaying a graphical user interface for a Virtual Reality (VR) medical test in accordance with the teachings herein.

In another aspect, in accordance with the teachings herein, there is provided a computer readable medium comprising a plurality of instructions that are executable on a processor of a system for adapting the system to implement a method for generating and displaying a graphical user interface for a Virtual Reality (VR) medical that is performed on a subject via a VR device worn by the subject, wherein the method is defined in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 5 shows a letter-coded computer screen image of the VR test creation interface of FIG. 4 for creating VR based medical tests.

FIG. 17A shows an example embodiment of a test-specific UI area for a Contrast Sensitivity and Visual Acuity VR test.

FIG. 17B shows a schematic diagram of an example of the Visual Acuity VR test corresponding to the UI of FIG. 17A.

FIG. 20A shows an example embodiment of a test-specific UI area for a Synoptophore VR test.

FIGS. 20B and 20C show schematic diagrams of first and second example representations of a Synoptophore VR test corresponding to the UI of FIG. 20A.

FIGS. 21B and 21C show schematic diagrams of first and second example representations of the Lees Screen VR test corresponding to the UI of FIG. 21A.

Figure 1:
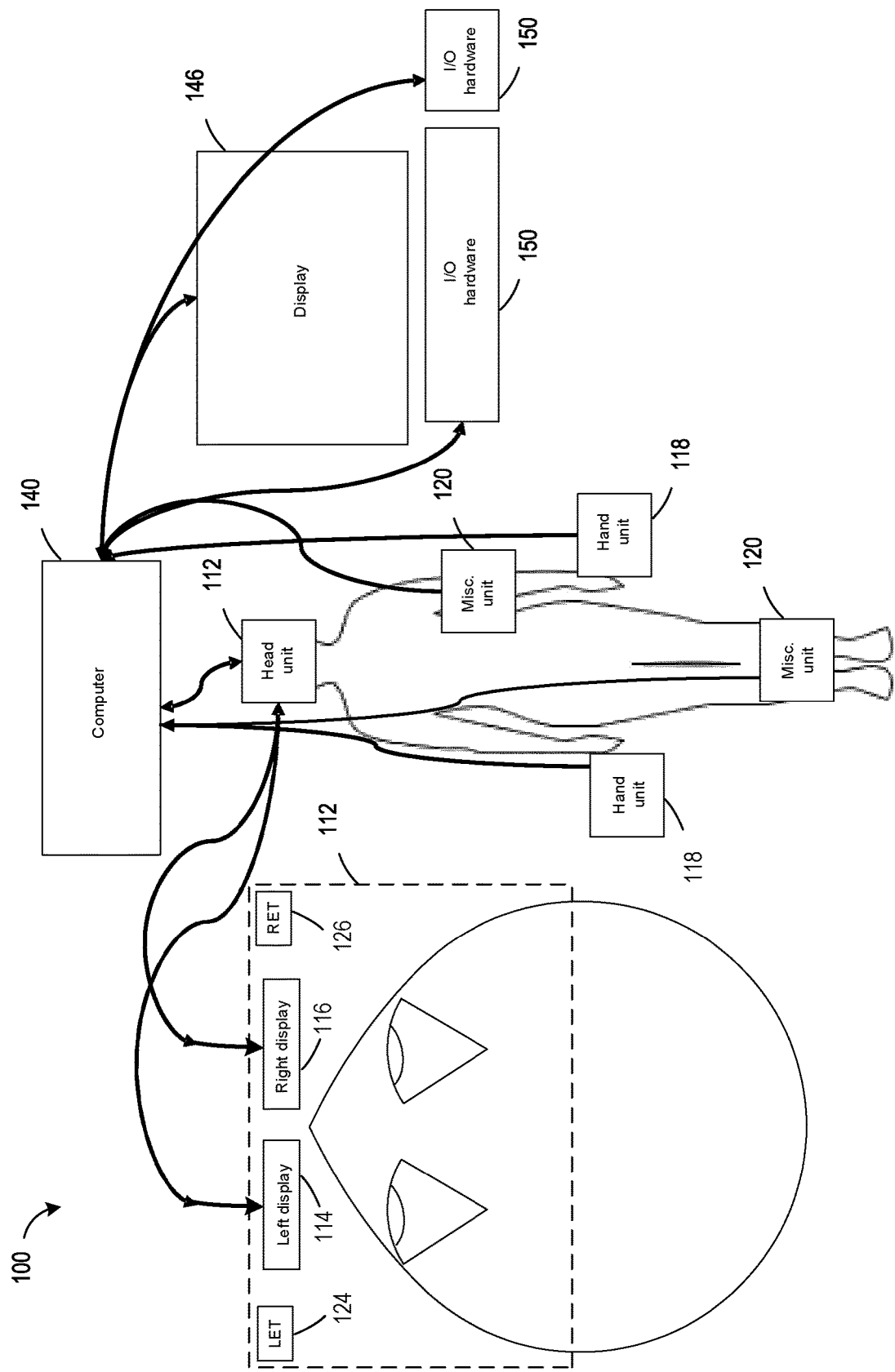
FIG. 1 shows a block diagram of an example embodiment of a VR system for generating and providing VR medical tests to a subject.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems, or methods having all of the features of any one of the devices, systems, or methods described below or to features common to multiple or all of the devices, systems, or methods described herein. It is possible that there may be a device, system, or method described herein that is not an embodiment of any claimed subject matter. Any subject matter that is described herein that is not claimed in this document may be the subject matter of another protective instrument, for example, a continuing patent application, and the applicants, inventors, or owners do not intend to abandon, disclaim, or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical signal, radio signal, electrical connection, or a mechanical element depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5%, or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

It should also be noted that the use of the term "window" in conjunction with describing the operation of any system or method described herein is meant to be understood as describing a user interface for performing initialization, configuration, or other user operations.

The example embodiments of the devices, systems, or methods described in accordance with the teachings herein may be implemented as a combination of hardware and software. For example, the embodiments described herein may be implemented, at least in part, by using one or more computer programs, executing on one or more programmable devices comprising at least one processing element and at least one storage element (i.e., at least one volatile memory element and at least one non-volatile memory element). The hardware may comprise input devices including at least one of a touch screen, a keyboard, a mouse, buttons, keys, sliders, and the like, as well as one or more of a display, a printer, and the like depending on the implementation of the hardware. The terms "mouse click" or "mouse drag" for example are understood to be interchangeable with the term "touch", meaning tapping a touch screen or dragging a finger across a touch screen, respectively.

It should also be noted that there may be some elements that are used to implement at least part of the embodiments described herein that may be implemented via software that is written in a high-level procedural language such as object-oriented programming. The program code may be written in C++, C#, JavaScript, Python, or any other suitable programming language and may comprise modules or classes, as is known to those skilled in object-oriented programming. Alternatively, or in addition thereto, some of these elements implemented via software may be written in assembly language, machine language, or firmware as needed. In either case, the language may be a compiled or interpreted language.

At least some of these software programs may be stored on a computer readable medium such as, but not limited to, a ROM, a magnetic disk, an optical disc, a USB key, and the like that is readable by a device having a processor, an operating system, and the associated hardware and software that is necessary to implement the functionality of at least one of the embodiments described herein. The software program code, when read by the device, configures the device to operate in a new, specific, and predefined manner (e.g., as a specific-purpose computer) in order to perform at least one of the methods described herein.

At least some of the programs associated with the devices, systems, and methods of the embodiments described herein may be capable of being distributed in a computer program product comprising a computer readable medium that bears computer usable instructions, such as program code, for one or more processing units. The medium may be provided in various forms, including non-transitory forms such as, but not limited to, one or more diskettes, compact disks, tapes, chips, solid state drives, cloud storage, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

By way of background relating to the technical challenges presented, research into the utilization of VR in the domain of medical testing is still in its infancy. The spectrum of clinical tests developed may be utilized differently by different levels of health care professionals, i.e., by primary care professionals (screening tool), secondary eye care providers (triaging tool), and tertiary care services for diagnostic and management purposes (treatment tools). There is also a market for private practices in optometry, who are the foremost interface with the general population, which will benefit from improved medical testing while expanding their scope of practice to include some of the ophthalmic assessment capabilities offered herein.

Current tests are cumbersome, time consuming, and expensive. There is a need for a system that combines multiple tests into one device that is a consumer-grade, readily available, and relatively inexpensive device. For example, current offerings for certain tests (administered using separate equipment) can cost as much as $100,000 per test or more. A system that combines multiple tests into one device not only increases efficiency, but also provides an environment that can enhance or replace multiple tests, or even create entirely new tests that are not currently developed and may not even be possible or feasible outside of the VR world.

While the various teachings herein are described with respect to generating and performing VR-based medical tests including VR-based vision tests, for illustrative purposes, in alternative embodiments, the teachings herein may be used to generate and perform other types of medical tests including, but not limited to, at least one of VR-based mental, emotional, and cognitive functioning tests, for example, related to various conditions such as, but not limited to, autism, Alzheimer's, dementia, and post-traumatic stress disorder (PTSD). Generally, medical tests refer to the displaying and recording of distance, orientation, and visual/audio context data of a subject and video/audio stimulus in a medical context. As such, a medical test does not necessarily mean providing scores, diagnosis, or any kind of algorithmically derived medical assessment. The intention is to provide doctors and clinicians with appropriate expertise with more precise measurements and data so they may be better informed in making assessments, making diagnoses, and prescribing therapies.

With respect to VR-based vision testing, the teachings herein may be used to generate and perform various vision tests including, but not limited to, at least one of a visual acuity test, a depth perception test such as a Brock string test, a color vision test, as well as tests for fovea functioning and binocular vision, for example.

VR-based tests may assist in the measurement of eye function by presenting stimuli that approximate or improve upon the gold standard testing currently in use throughout ophthalmology and optometry. The various VR-based vision tests described herein may provide information related to, for example, at least one of visual acuity, eye function, eye and head movement, visual field, eye alignment, color detection, and pupillary response.

In accordance with the teachings herein, the example embodiments that are described provide technical solutions to the challenges of implementing VR versions of physical tests that are as good as, if not better than, the Gold standard. The VR versions may, for example, improve on the Gold standard in at least one of the following areas depending on the particular test: better precision, better consistency, unlimited stimulus shape/size, stimulus being configurable to be displayed to either eye without the need for at least one of lens polarization or color filtering; and eye movement, head movement, hand movement, vocal sounds, and/or biometric data capable of being recorded with the visual stimulus context preserved in full 3D for later analysis.

As it happens, visual systems function the same way in VR as they do in real life, so it is therefore possible to do many of the conventional eye tests conducted in an ophthalmological setting while benefiting from the precision and reproducibility of performing these tests in a simulated VR environment. This may greatly speed up setup and testing time, and help ensure less qualified individuals can meaningfully contribute to gathering data, helping to free up valuable time of the experts and/or the devices they use.

In order to make the testing experience more precise, VR tests can use protocols, in accordance with the teachings herein, to ensure test settings are consistent from subject to subject (i.e., patients), and from appointment to appointment for the same subject. This may include setting specific values for at least one of the scale of the visual stimuli, the distance of the visual stimuli from the subject's eyes, the rotation of the visual stimulus, the lighting (e.g., light intensity) of the visual stimuli, and other context settings, for example. All of these settings can be perfectly consistent across different tests since VR is used to deliver the visual tests.

In accordance with the teachings herein, VR tests may be generated and delivered using conventional VR hardware to deliver one or more VR vision tests to a subject and record the subject performance/behavior. However, in alternative embodiments, the VR vision tests may be augmented to be provided, along with ophthalmological apparatus, to a subject in order to obtain certain data about the subject's vision or data for correcting the subject's vision such as visual refractive corrections, which may be obtained when VR stimulus is combined with a phoropter equipped with, for example, deformable lenses. VR vision tests may be generated for providing Fundas images or performing visual field tests when the VR system is equipped with an appropriate ophthalmological device such as a device having a visual field greater than 110 degrees, for example. Accordingly, as hardware devices evolve, an increasing number of VR vision tests can be created using the teachings herein.

In one aspect, in accordance with the teachings herein, there are provided various embodiments for a system and method for a protocol authoring tool to allow a user to create and/or modify VR based medical tests and record data from subjects who undergo the tests, as well as computer products for use therewith.

In another aspect, in accordance with the teachings herein, there is at least one embodiment of a system and method for generating and administering the VR version of currently employed clinical tests on a single head-mounted VR viewing device (these tests can be referred to as VR clinical tests). The VR clinical tests that can be designed range from vision tests performed on a standard vision chart to vision tests that use eye tracking technology to detect and quantify disorders of eye movements while simultaneously confirming secondary cortical adaptations from these disturbances. In the latter case, in at least one embodiment, an Eye Tracking Sensor Device (ETS) can be embedded in a VR headset to present innovative stimuli attractive to children and monitor their responses via the ETS rather than traditional tests that include receiving verbal answers. As another example, in at least one embodiment, the VR headset may be used to perform a quasi-simultaneous assessment of the subject's two eyes by using the VR headset to present dichoptic stimuli to the subject.

In another aspect, in at least one embodiment described herein, there is provided a method of recording the actual physical movement of a subject while the subject is being shown visual stimulus that is controlled by a user, presenting visual stimulus for other vision tests to the subject using pre-programmable protocols, recording data from the subject during each of these VR tests and then playing back the recorded data such that subject movement can be viewed by the user in VR on 2D monitors via an avatar representing the subject in VR. The method is implemented, for example, on one or more computers and/or electronic devices.

In another aspect, in at least one embodiment described herein, there is provided a system and method which allows a user to organize visual stimuli including manipulating existing visual stimuli, which may then be presented to the subject while data from the subject is recorded and which may be played back later as described previously. In at least one embodiment, the stimulus can be automatically set up with one click. Automatic setup may be achieved with a preset, and possibly modifiable, protocol. For example, at least one embodiment of the system described herein provides means to set up and save a protocol for later access, and possibly save groups of protocols to comprise a given study. Protocols may be shared and used across systems to ensure consistent testing stimulus for every subject regardless of location.

In another aspect, in at least one embodiment described herein, there is provided a system and method that enables the user to use mouse movement, or another control input, to control a stimulus that is displayed concurrently to the subject in VR. The user can then direct the subject using the control input. The subject's actions may be either self-directed or instructed by the user (e.g., clinician, ophthalmologist, or tester). For example, the subject may regard a particular provided VR visual stimulus and answer questions from the user on how it appears. The interaction between the user and subject (e.g., their questions and answers) may be recorded into (e.g., audio) data for later playback, for example, if the user has input that they have permission to do so. Alternatively, or in addition, speech recognition telemetry may be used to record a confidence score that the user responded with one of a few choices to capture relevant data (e.g., whether the subject identified the correct letters on an eye chart), which may be modified (e.g., masked, scrubbed, encrypted) to protecting identity.

In another aspect, in at least one embodiment described herein, there is provided a system and method for recording the subject's movements while they are undergoing a test in VR including movement of at least one of their limbs, body, head, eyes, and pupil size. For example, the system may record biometric data by using appropriate sensor hardware and then digitally represent it in 3D virtual playback for later analysis. The recorded subject movements can then be played back to the user in the real world using a computer display, or played back to the user in VR.

In another aspect, in at least one embodiment described herein, there is provided a system and method for generating and presenting visual stimuli as specific VR vision tests in which a VR vision stimulus is provided to the subject that will have the same effect on the vision of the subject as if the stimulus was provided to the subject in the real world. Data from the subject is recorded while the VR vision stimulus is being presented, and the recorded subject data may be useful in the assessment of various vision disorders depending on how the VR vision stimulus was defined.

In another aspect, in at least one embodiment described herein, there is provided a system and method that allows a user to filter a VR visual stimulus so that the filtered VR visual stimulus has specific light wavelengths (i.e., specific types of color) at varying light intensities. Specific simulated light wavelengths may also be provided, as RGB displays cannot output light wavelengths; rather, they output combinations of red, green, and blue to simulate as many light wavelengths as possible. The filtered VR stimulus is presented to the subject in VR while data is recorded from the subject where the recorded subject data can be analyzed to determine the subject's color sensitivity.

In another aspect, in at least one embodiment described herein, there is provided a system and method that allows a user to alter the rotation and position of a VR vision stimulus that is presented to each of the subject's individual eyes while the subject is in VR. Subject data is recorded simultaneously to the presentation of the VR stimulus. The recorded subject data can provide data relating to the subject's eye alignment and rotation.

In another aspect, in at least one embodiment described herein, there is provided a system and method for representing and recording each axis of rotation of the subject's head relative to the direction of a VR visual stimulus while the subject is in VR. The various axis of rotation of the subject's head can then be played back to the user either in the real world or in VR.

In another aspect, in at least one embodiment described herein, there is provided a system and method for accessing previously recorded subject data where this subject data may include data about one or more of: (a) the movement of at least one of the subject's head, hands, eyes, and fingers; and (b) the subject's interactions with VR-based controllers and test stimuli. The accessed subject data can then be displayed to another person, e.g., the user, a clinician, or a doctor, while this person is also in the same VR environment as the subject was when the subject data was recorded. For example, the system may comprise VR hardware that supports tracking several joints/body parts, or only the head, or head and hands, etc. of the subject. The software driving the hardware may be configured to communicate with whatever capabilities for tracking the hardware has and record them for later playback in VR. Support for new types of tracking and other biometric capture may be added as needed.

At least some of the programs associated with the devices, systems, and methods of the embodiments described herein apply principles and/or operations relating to 3D manipulation of images. For example, the programs may incorporate six degrees of freedom (also known as "6DOF") for the purposes of translation and rotation of a VR visual stimulus along or around the x-axis, y-axis, and z-axis. "Translation" may be used to represent movement in 3D space. Rotation may refer to pitch, yaw, and roll, for example when applied to camera rotation. Rotation may be represented by x,y,z rotation. Prismatic rotational translation effects may be measured in diopters, Δ, or torsional rotation, for example as used in eye movement measured in degrees. Other terms of art may also be used in the context of vision testing, film/camera work, VR, or digital 3D modelling and design, where applicable.

Reference is first made to FIG. 1, showing a block diagram of an example embodiment of a VR system 100 that can be used to generate VR tests and present VR stimuli to the subject for performing medical testing. The VR system 100 may also be used to record data from the subject when a VR stimulus is presented to the subject and perform an action on the subject data including at least one of storing the recorded subject data, presenting the recorded subject data to a user in VR or in the real world and sending the subject data to another device over a wired or wireless communication network. The VR medical testing (e.g., a VR visual test) may be controlled by a user (e.g., a clinician, or an operator).

The VR system 100 comprises a head unit 112 that includes a left display 114 and a right display 116 that are configured to provide a left VR view and a right VR view to the subject's left eye and right eye, respectively, when the head unit 112 is worn by the subject. The left display 114 and the right display 116 display VR images that provide the subject with the impression that they are inside a realistic VR environment that visually follows the same rules of perspective and vision as in the real world. Examples of such rules include, but are not limited to, further away objects appearing smaller, closer objects occluding further objects, and perspective distorting shapes of objects depending on their relative spatial relationship. The left display 114 and the right display 116 can be virtually rotated or moved relative to each of the subject's left eye and right eye, respectively. Color and other types of image distortion filters may also be applied individually or in combination prior to displaying the visual stimuli on at least one of the left display 114 and the right display 116.

The head unit 112 may also include a left eye tracking sensor 124 disposed adjacent to the left display 114 and a right eye tracking sensor 126 disposed adjacent to the right display 116. Each or both of the left eye tracking sensor 124 and the right eye tracking sensor 126 may be referred to as an eye tracker. The left eye tracking sensor 124 and the right eye tracking sensor 126 may generate eye tracking data of the subject's left eye and right eye, respectively. The eye tracking data can provide data specific to the subject's eyes which can be analyzed by a user device, such as a computer 140. Examples of such eye tracking data include, but are not limited to, eye position, pupil size, or pupil shape.

The computer 140 (e.g., a central computing unit) is configured to render the VR environment and send the VR data associated with the correct VR views to the left display 114 and the right display 116. The computer 140 can also receive eye tracking data from the left eye tracking sensor 124 and right eye tracking sensor 126 to be stored by the computer 140 or sent to another user device. Additionally, the computer 140 receives position and rotation data from a head unit 112, hand unit(s) 118, and miscellaneous unit(s) 120 for additional processing and simulation purposes. The computer 140 utilizes an operating system and support software to provide the appropriate functions.

The head unit 112 may contain sensors to collect position data and rotation data of the subject's head which can be sent to the computer 140. The hand units 118 contain sensors to collect position and rotation data of the subject's hands or arms which can be sent to the computer 140. Additionally, the hand units 118 (e.g., VR controllers or VR wands) can be used by the subject to provide input data that can be sent to the computer 140, including, but not limited to, button presses, button clicks, trackpad tracking, and joystick tracking, for example, so that the user can perform certain functions in the VR environment. The miscellaneous units 120 may collect and send position and rotation data for other areas of the subject's body. Alternatively, or in addition, the miscellaneous units 120 may be implemented using sensors that can collect biometric data from the subject which include, but are not limited to, at least one of rate of breath, heart rate, galvanic skin response, electroencephalogram (EEG) data, and electrocardiogram (ECG) data. Accordingly, the miscellaneous units 120 may be one or more trackers and/or one or more physiological sensors. The miscellaneous units 120 may be controlled by a sensor control that may be accessed through software or hardware, or a combination thereof. The head unit 112, hand units 118, and miscellaneous units 120 may be connected to the computer 140, for example, by physical cable, or by a wireless signals transmitted according to a wireless communication protocol, or via a wired or wireless local area network.

A display 146 is connected to the computer 140 for use by the user. The user may provide inputs on various input/output (I/O) hardware 150 which may include, but are not limited to, a computer keyboard or a touchscreen display for input of commands and text entries. Other I/O hardware 150 the user may use includes a mouse for input from the user to interact with the software user interface and control certain aspects of the VR visual stimuli.

In at least one embodiment, the system 100 is capable of simulating a virtual 3D world with VR images that are updated at an appropriate rate, such as at least 90 times per second, relative to the subject's head position and eyes. The computer 140 may, for example, run Windows or a similar supported operating system and be computationally powerful enough to update the volumetric scene at least 90 times per second. The left display 114 and the right display 116 may be implemented using tiny displays along with lenses that focus an image into each of the subject's eyes so as to simulate stereopsis and enable the subject to adjust interpupillary distance as required between their eyes and the displays based on the subject's particular ocular and facial physiology. In addition, the lenses may be implemented such that they are moveable so that the user can ensure as much proper visual focus as possible for the subject.

In at least one embodiment, the system 100 may be compatible with one or more of OpenVR, OSVR, and OpenXR standards. The system 100 may support SteamVR. The system 100 may be run on an HTC VIVE™ or HTC VIVE™ Pro. The system 100 may use or be compatible with Oculus, Pico Neo, or Windows-based VR headsets and equipment. The system 100 may also use eye tracking software, such as Tobii VR or Pupil Labs VR eye trackers.

Figure 2:
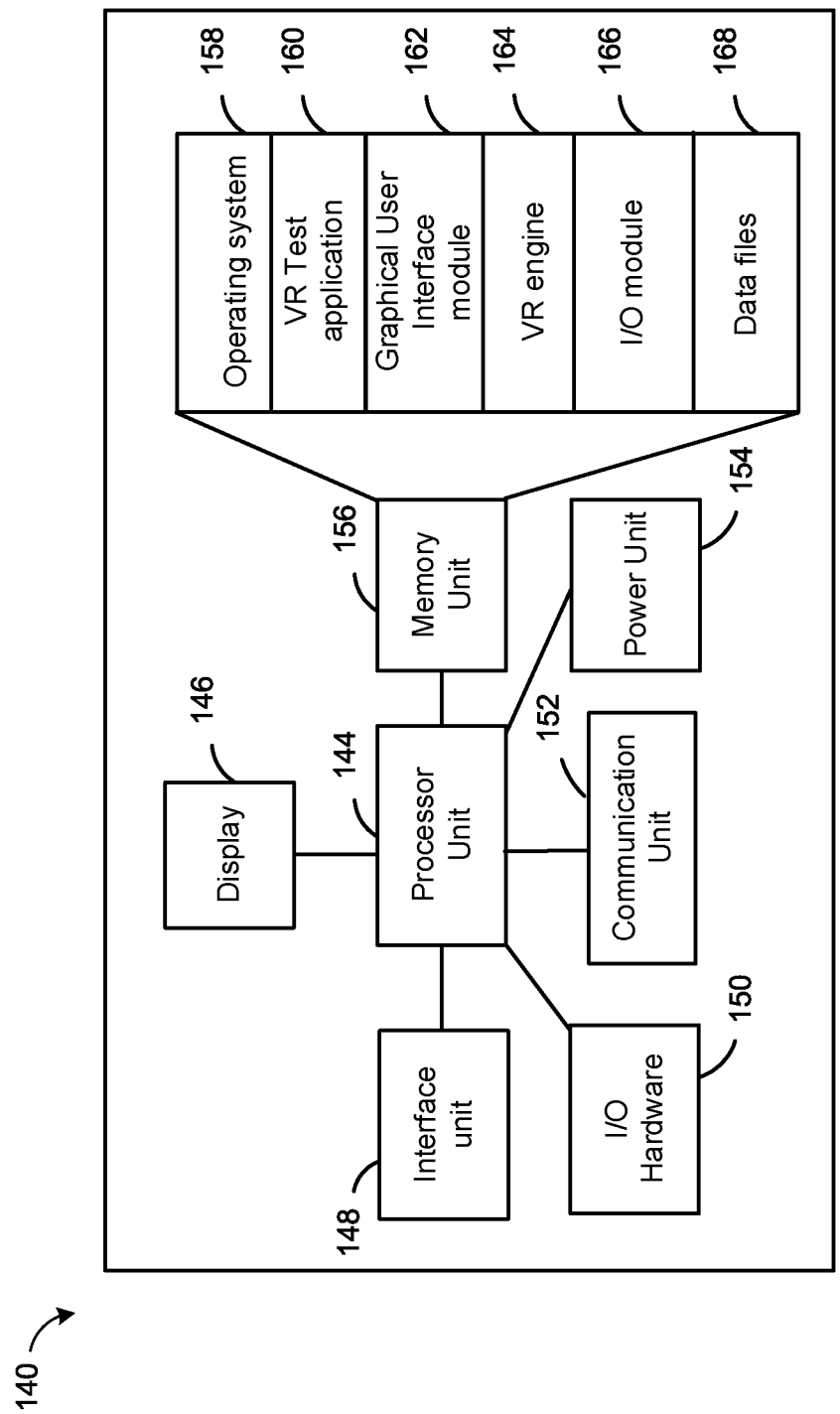
FIG. 2 shows a block diagram of an example embodiment of a computing device that can be used with the VR system of FIG. 1.

Referring now to FIG. 2, shown therein is a block diagram of an example embodiment of the computer 140 that can be used with the VR system 100 of FIG. 1. The computer 140 may run on a single computing device (e.g., desktop, laptop, notepad), and includes a processor unit 144, the display 146, an interface unit 148, the input/output (I/O) hardware 150, a communication unit 152, a power unit 154, and a memory unit (also referred to as "data store") 156. In other embodiments, the computer 140 may have more or less components but generally function in a similar manner. For example, the computer 140 may be implemented using more than one computing device. The computer 140 may function as a server.

The processor unit 144 may include one processor. Alternatively, there may be a plurality of processors that are used by the processor unit 144, and these processors may function in parallel and perform certain functions. The display 146 may be, but not limited to, a computer monitor or an LCD display such as that for a tablet device or a desktop computer. The communication unit 152 includes various communication hardware for allowing the processor unit 144 to communicate with other devices. The communication hardware includes at least one of a network adapter, such as an Ethernet or 802.11x adapter, a BlueTooth radio or other short range communication device, and a wireless transceiver for wireless communication.

The memory unit 156 stores program instructions for an operating system 158, a VR test application 160, a graphical user interface (GUI) module 162, a VR engine 164, an input/output (I/O) module 166, and one or more data files 168. The VR test application 160 comprises software instructions that, when executed, configures the processor unit 144 to operate in a particular manner to implement various functions, tools, processes, and methods for the system 100. For example, the VR test application 160 can include programs for instructing the various hardware trackers to record and transmit movement data for at least one of the subject's body parts including one or more of their eyes. Accordingly, the functionality of the VR test application 160 may be implemented, for example, using a combination of hardware, firmware, and/or software.

The graphical user interface module 162 stores, uploads, creates, generates, modifies, and/or outputs GUI elements (or GUI building blocks). The GUI elements may serve as the building blocks for a VR test creation interface. The GUI elements may be manipulated by a user to control the operation of the head unit 112 during VR medical testing. When the GUI elements are displayed, the GUI elements may be associated with a protocol on a user device. The GUI elements may have user adjustable settings for modifying the functioning of a VR medical test (e.g., a VR visual test). The GUI module 162 may, for example, operate in conjunction with the VR engine 164 to associate 2D inputs viewed on the display 146 with 3D outputs in the head unit 112. Accordingly, the functionality of the GUI module 162 may be implemented, for example, using a combination of hardware, firmware, and/or software.

The VR engine 164 generates the VR environment and outputs an image of the VR environment to the head unit 112, such as to the left display 114 and the right display 116. The VR engine 164 may update a virtual action and display the virtual action on the head unit 112. For example, input from the head unit 112 or the hand unit 118 may be received by the I/O hardware 150, processed by the I/O module 166, and/or processed by the VR engine 164. The VR engine 164 may then provide any necessary data (e.g., positional, graphical) to the head unit 112 to update any visual stimuli that is provided to the head unit 112. Accordingly, the functionality of the VR engine 164 may be implemented, for example, using a combination of hardware, firmware, and/or software.

The VR engine 164 may generate the images, video, and/or stimuli to be displayed in the head unit 112 using, for example, the Steam VR engine, Unity VR engine, OpenVR API, Oculus VR Plugin, PicoVR, or Unreal engine. The Unity VR engine may include a virtual reality tool kit (VRTK) plugin. The VR engine 164 may use sensor data that represent the subject's head position and orientation, for example, to update the images that are shown to the subject in the subject's field of view (FOV).

The input/output module 166 receives input data that was obtained by the I/O hardware 150, processes the input data, and/or generates output data (or signals) that are then sent to the I/O hardware 150. The input/output module may, for example, operate in conjunction with the VR engine 164 to communicate data (or signals) between one or more of the computer 140, the head unit 112, the hand unit 118, and miscellaneous units 120. Accordingly, the functionality of the input/output module 166 may be implemented, for example, using a combination of hardware, firmware, and/or software.

The data files 168 may store any temporary data (e.g., data that is not needed after a VR test is completed) or permanent data (e.g., data saved for later use), such as subject data (e.g., a subject ID), camera settings, screenshots, and recordings.

The data files 168 may, for example, be generated by data processed by one or more of the VR test application 160, the graphical user interface module 162, the VR engine 164, and the input/output module 166. The data files 168 may also include various subject data for each subject that undergoes VR medical testing such as identification data, physiological data and recorded subject data during VR medical testing.

In at least one embodiment, the computer 140 is compatible with, configured to operate under, or built to OpenVR standards (or functionally equivalent standards). In at least one embodiment, the computer 140 comprises components (e.g., operating system 158, processor unit 144, I/O hardware 150) capable of supporting 3D authoring software and VR software to OpenVR standards.

Figure 3:
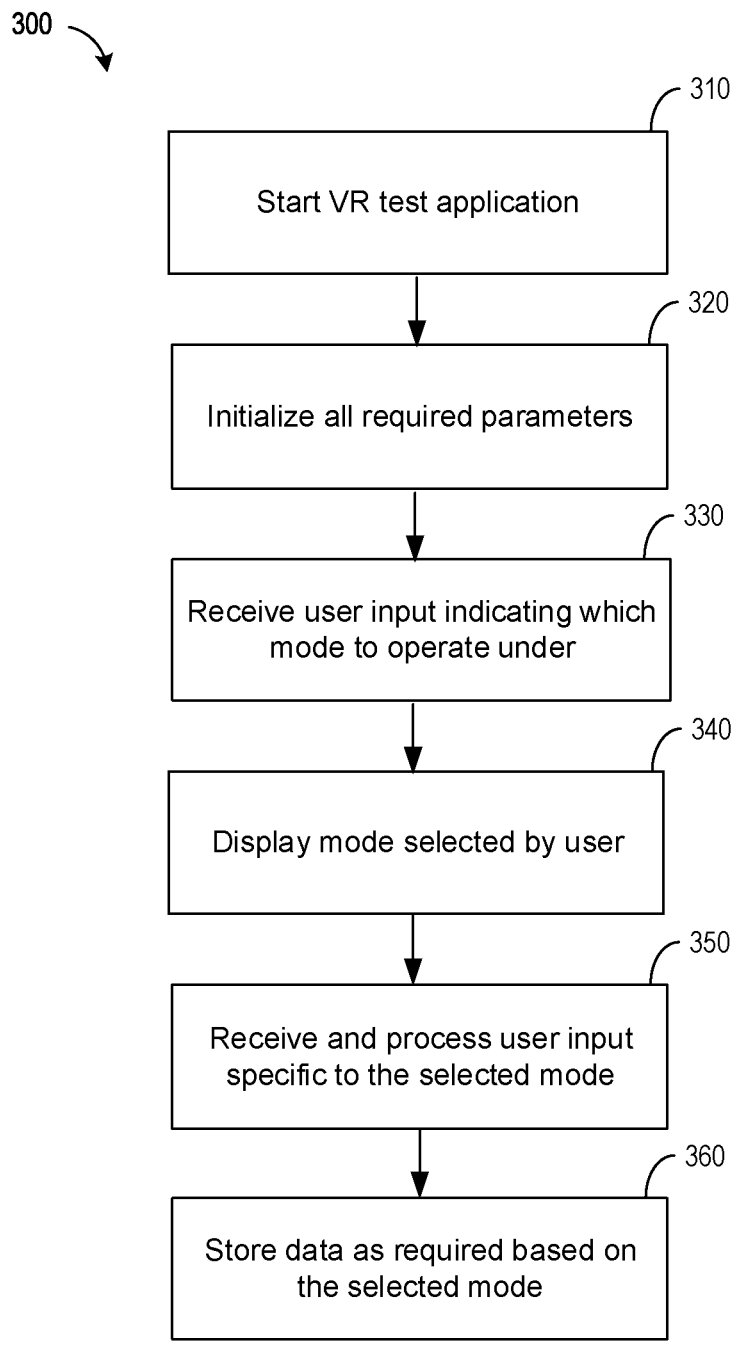
FIG. 3 shows a flow chart of an example embodiment of a method of creating, updating, and conducting VR based medical tests.

Referring now to FIG. 3, shown therein is a flow chart of an example embodiment of a method 300 of creating, updating, and conducting VR-based medical tests. Method 300 may be carried out, for example, by some or all of system 100. Method 300 may be implemented, for example, on some or all of computer 140.

At 310, the computer 140 starts the VR test application 160.

At 320, the computer 140 initializes all required parameters for the VR test application 160 and for any other modules (e.g., GUI module 162, VR engine 164, input/output module 166) as needed.

At 330, the computer 140 receives user input indicating which mode to operate under, such as authoring a protocol, conducting a VR test, or recording subject data.

Figure 33A:
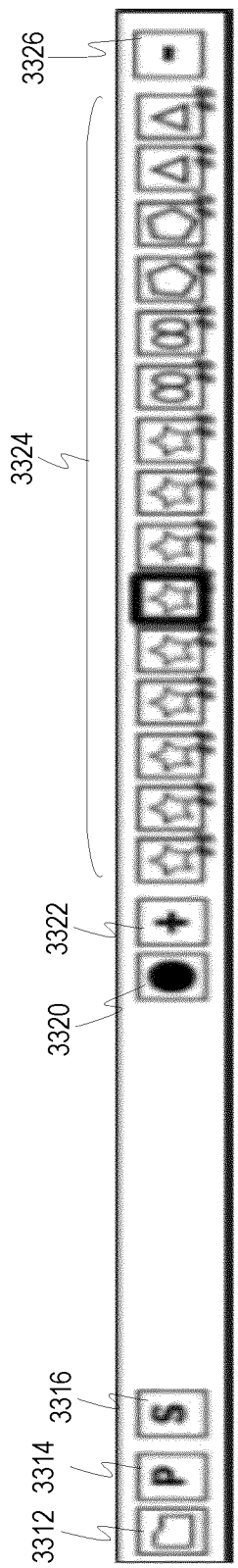
Figure 34:
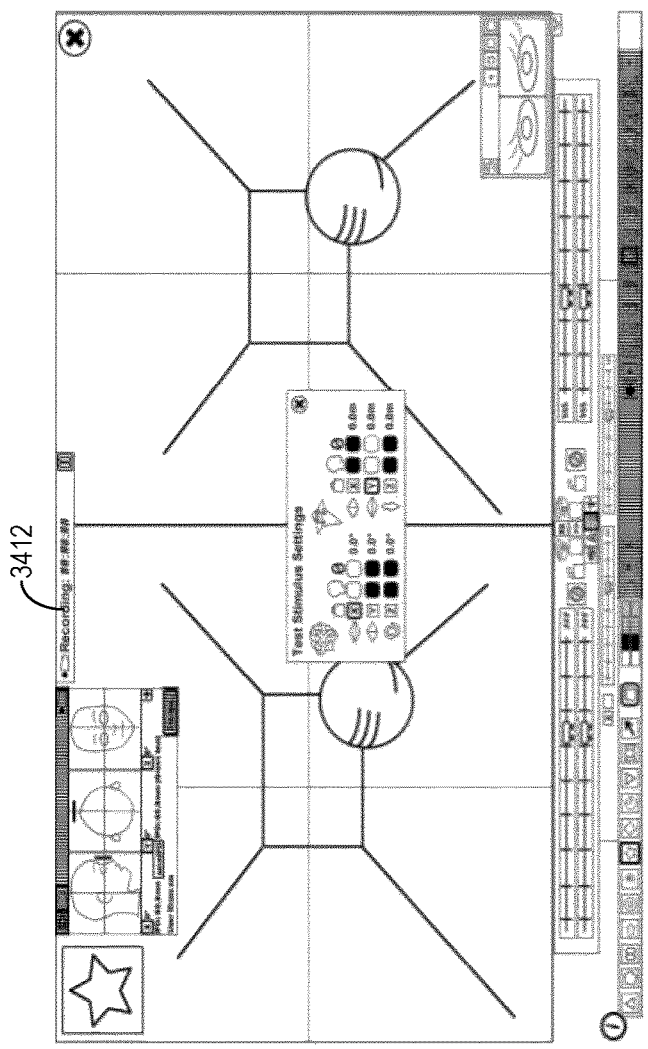
FIG. 34 shows an example embodiment of a recording user interface.

At 340, the computer 140 displays a user interface according to the mode that was selected by the user. For example, if authoring a protocol was selected, the computer 140 displays a GUI for the protocol authoring mode (e.g., as shown in FIG. 33A). For example, if conducting a VR test was selected, the computer 140 displays a VR test (e.g., as shown in any one of FIGS. 14A to 22). For example, if recording subject data was selected, the computer 140 displays a recording user interface (e.g., as shown in FIG. 34).

Figure 4:
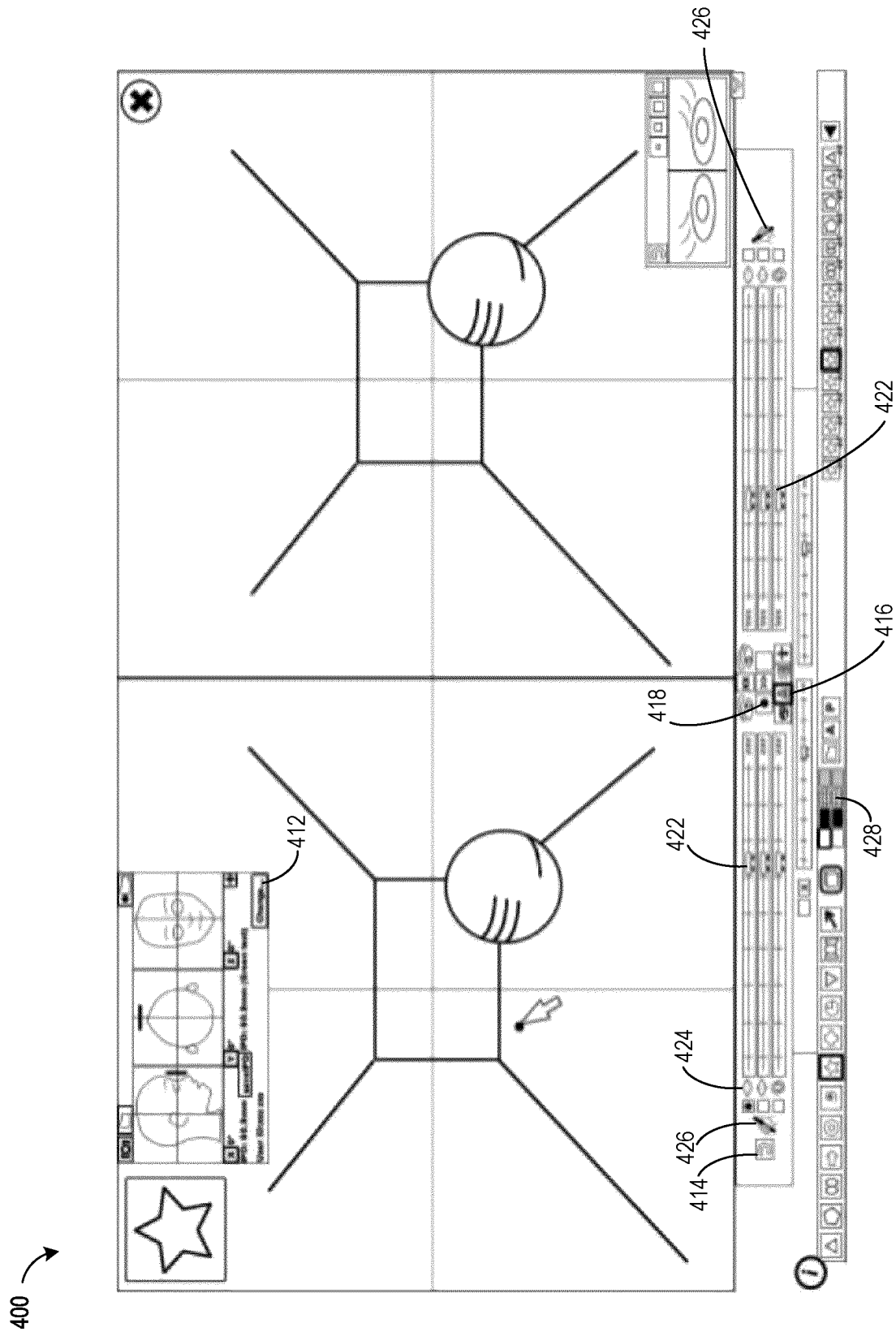
FIG. 4 shows a computer screen image of an example embodiment of a VR test creation interface for creating VR based medical tests.
Figure 42:
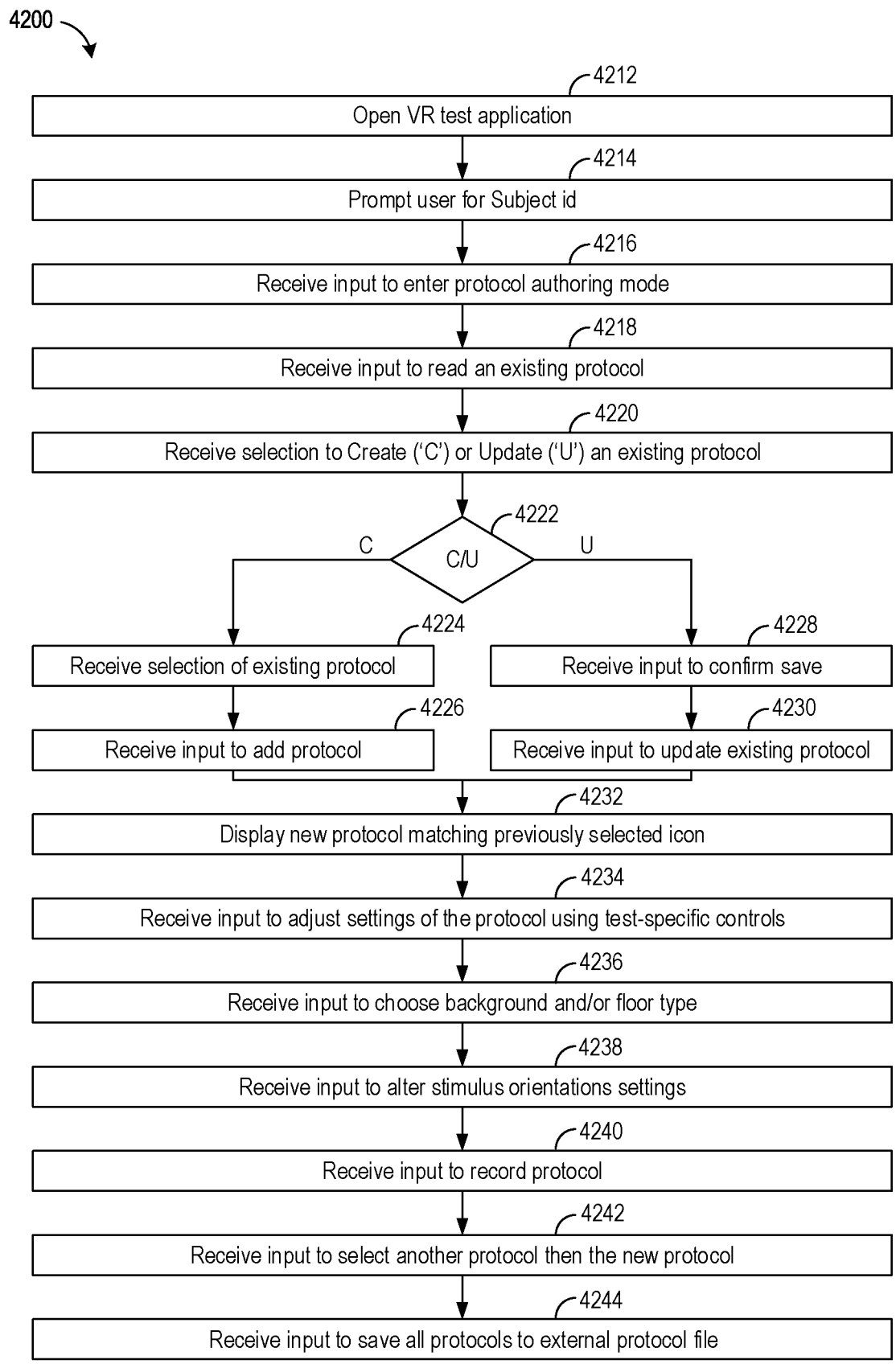
FIG. 42 shows a flow chart of an example embodiment of a method of creating and updating a protocol.

At 350, the computer 140 receives and processes user input specific to the mode that the user selected. For example, if the "authoring a protocol" mode was selected by the user, the computer 140 carries out a method of creating and updating a protocol (e.g., as shown in FIG. 42). As another example, if the "conducting a VR test" mode was selected by the user, the computer 140 allows the user to interact with the subject in VR through the head unit 112 by generating and presenting stimuli for a selected VR test (e.g., as shown in FIG. 4). As another example, if the "recording subject data" mode was selected by the user, the computer 140 allows the user to record subject data while conducting a VR test (e.g., as shown in FIG. 34).

At 360, the computer 140 stores data as required based on the mode the user selected, the data generated while in that mode, and the data (e.g., settings, recordings) that the user selected to save. Each of these modes are described in further detail below.

Referring now to FIG. 4, shown therein is a computer screen image of an example embodiment of a VR test creation interface 400 for creating VR-based medical tests. Some or all of the VR test creation interface 400 may be implemented, for example, on some or all of computer 140.

The VR test creation interface 400 may be used, for example, to provide an integrated development environment (IDE) for a user (e.g., a clinician) or a developer (e.g., a person developing a medical test) that provides the development tools to create and/or modify a medical test, such as a VR vision test (e.g., to test binocular vision).

For the purposes of describing the VR test creation interface 400, the following terms are defined as follows:

Subject: person currently viewing a medical test in VR via a VR headset; the person may be subjected to a VR based stimulus; the person may interact with VR controllers.

Subject ID: a unique way to identify a given subject, which may be configured to reveal no personally identifiable data.

User: a person (e.g., clinician) administering the test who may be trained in how to administer the VR-based medical test and interpret verbal patient responses for proper diagnosis; the user may see a version of what the subject is experiencing on a computer plus an overlaid user interface that can be accessed to alter the subject's VR experience.

Developer: a person who creates or modifies the VR-based medical test (the user and developer may be the same person).

VR space: virtual 3D space that the subject is visually immersed in through the VR technology.

Subject HUD: a heads-up display or 2D overlay that appears in front of at least one the subject's eyes but not in the VR space per se.

3D authoring a software-development environment for creating 3D or VR software: projects (e.g., simulations, games), such as Unity 3D.

Prefab: a code module that is compatible with 3D authoring software projects and can run inside them, and interoperate with code written within guidelines specified by the 3D authoring software.

VR headset: includes at least one display inside a headset worn by the subject that simulates VR and may be used to precisely track the subject's eye movement.

Gold standard a test that has been proven over time and with multiple peer test: reviewed studies to be effective to deliver measurements within a specified tolerance of error.

In the VR test creation interface 400, there is a plurality of GUI elements including, but not limited to, one or more of at least one button, at least one slider, at least one icon, at least one control input, at least one indicator, at least one toggle, and at least one text box. In this example embodiment, the GUI elements may include:

A. Subject-related single state buttons 412;
B. General buttons 414 (e.g., in grey);
C. First toggle buttons 416 with an icon in the center that indicate the ON state which may have a colored (e.g., gold) frame around them;
D. Second toggle buttons 418 without an icon that indicate the ON state with a dot in the center (e.g., colored or white depending on the function);
E. Third toggle buttons (not shown) that are not a regular button shape such as the goggle toggles in a Worth Four Dot (WFD) test, which may use a gradient glow to indicate "on" status;
F. Sliders 422 with detents and, where applicable, the numerical representation of their value in a user-friendly unit;
G. A first icon 424 showing the type of value a slider will affect, which may appear next to the slider, e.g. a distance slider; and
H. A VR controller icon 426, when VR is associated with or required to provide a certain type of functionality or input by the subject during a VR vision test.

A background menu 428 may be used to generate a background for the VR test creation interface 400. For example, the background menu 428 may be used to select a background that may be dark grey with some texture. The overall interface may be dark and reversed text. This can help ensure it does not detract from the view in subject VR view, or add any unnecessary light to the room. For example, if a room is very bright, a white VR visual stimulus will be visible when an appropriate VR background is used. If a room is very dark, a dark VR visual stimulus will be visible when an appropriate VR background is used. Furthermore, adjusting room color based on the current VR visual stimulus can be useful to establish proper contrast.

In at least one embodiment, the VR test creation interface 400 can provide a user interface that is configured to send and receive data to and from 3D authoring software, which may be system 100 or an external program that is compatible with system 100. Alternatively, or in addition, the VR test creation interface 400 can include 3D authoring software functionality. Alternatively, or in addition, the VR test creation interface 400 can include an editor in which the functionality of the GUI elements can be programmed, such as a protocol authoring tool.

In at least one embodiment, the VR test creation interface 400 can run as a standalone application. Alternatively, or in addition thereto, in at least one embodiment the VR test creation interface 400 can run on and be compatible with an available VR system. Alternatively, or in addition thereto, in at least one embodiment the VR test creation interface 400 can be compatible with eye tracking functionality of a VR system, if available and running. Alternatively, or in addition thereto, in at least one embodiment the VR test creation interface 400 can be generated without the ability to use eye tracking functionality. Alternatively, or in addition thereto, in at least one embodiment the VR test creation interface 400 can be used to enable VR data to be sent to a VR headset display in order to display VR environments reflective of the related settings determined in a main client window display such as display 146.

Referring now to FIG. 5, shown therein is a letter-coded computer screen image of the VR test creation interface 400 of FIG. 4 for creating VR-based medical tests. For ease of reference, the major sections of the VR test creation interface 400 can be divided as follows:

A. Subject data area 510. This area can be used to obtain real-time data about the subject as measured by a VR headset.
B. Subject VR view 520. This area approximately shows what the subject is seeing in VR (with limited field of view depending on the VR system and hardware display in use).
C. Eye camera area 530. These windows display eye videos of the subject's eyes that are recorded by cameras in the head unit 112 when such cameras are available.
D. Main camera settings area 540. These input buttons and toggles control the subject's VR view as well as which settings in the camera settings slider areas (H) are currently visible.
E. Test-specific UI area 550. These input controls change depending on which vision test is currently selected for testing a subject or modifying a test protocol during a protocol authoring process.
F. Test selection area 560. These input buttons allow the selection of a specific test and highlight which test is active.

G. Protocol selection & authoring area 570. This area includes several input buttons that allow the user to create, read, update, and delete protocols.

H. Camera settings sliders area 580. This is where, depending on which camera setting is chosen in the main camera settings area (D), a specific set of sliders (for each eye) can be accessed and altered. For example, the set of sliders may include sliders for rotating the eye cameras, sliders for displacing the eye cameras, sliders for blurring the eye cameras, sliders for applying a color filter to the cameras, sliders for turning one eye or both eye video windows on or off, sliders for turning the virtual laser pointer on or off, and/or sliders to swap eye on/off left to right and back.

For ease of reference, sections D to H may be referred to as the bottom user interface (UI) when they are located at the bottom of the VR test creation interface 400. Furthermore, for ease of reference, sections E and F may be referred to collectively as the test settings area and one or more of sections A to H may be referred to as the user UI.

In at least one embodiment, some or all of the user UI may be optionally displayable on mobile/tablet based devices, and the subject VR experience may be displayable on mobile VR/wireless devices (e.g., when they are on the same network, which can be a Local Area Network or a long-range wireless network). Therefore, in some embodiments, a subject's VR devices (i.e., VR headset, VR controller and an input device like a keyboard or touchscreen) may be connected to a clinician's computing device across the wireless network, for example through the Internet, to allow for remote VR vision testing to be performed on the subject.

In at least one embodiment, VR test creation interface 400 comprises one or more of the major sections A to H. Alternatively, or in addition, VR test creation interface 400 can be implemented such that one or more of the major sections A to H is hidden or disabled. Hiding or disabling major sections may be useful in certain contexts. For example, the user may want to prevent altering the eye position sliders by accident while running the subject through a series of protocols. Also, the user may be primarily concerned with viewing the VR environment in the GUI and want to maximize the view.

In at least one embodiment, the GUI module 162 has program code for generating a subject initialize UI that is presented on the display 146 of the computer 140 to the user. On launch of the VR test application 160, the subject initialize UI provides a message to the user to prompt the user to enter a subject ID and has a text box for receiving the subject ID. If the subject ID (e.g., a folder name in the data files 168) exists, then camera settings, screenshots, recordings, and any other subject-specific data may be stored in the data files 168. If the subject ID does not exist, then a new folder and default files are created and saved in the data files 168. Input of the subject ID may be programmatically forced to conform with a subject ID naming convention (e.g., VA-001-###) as well as file folder naming standards enforced by Microsoft Windows.

Figure 6A:
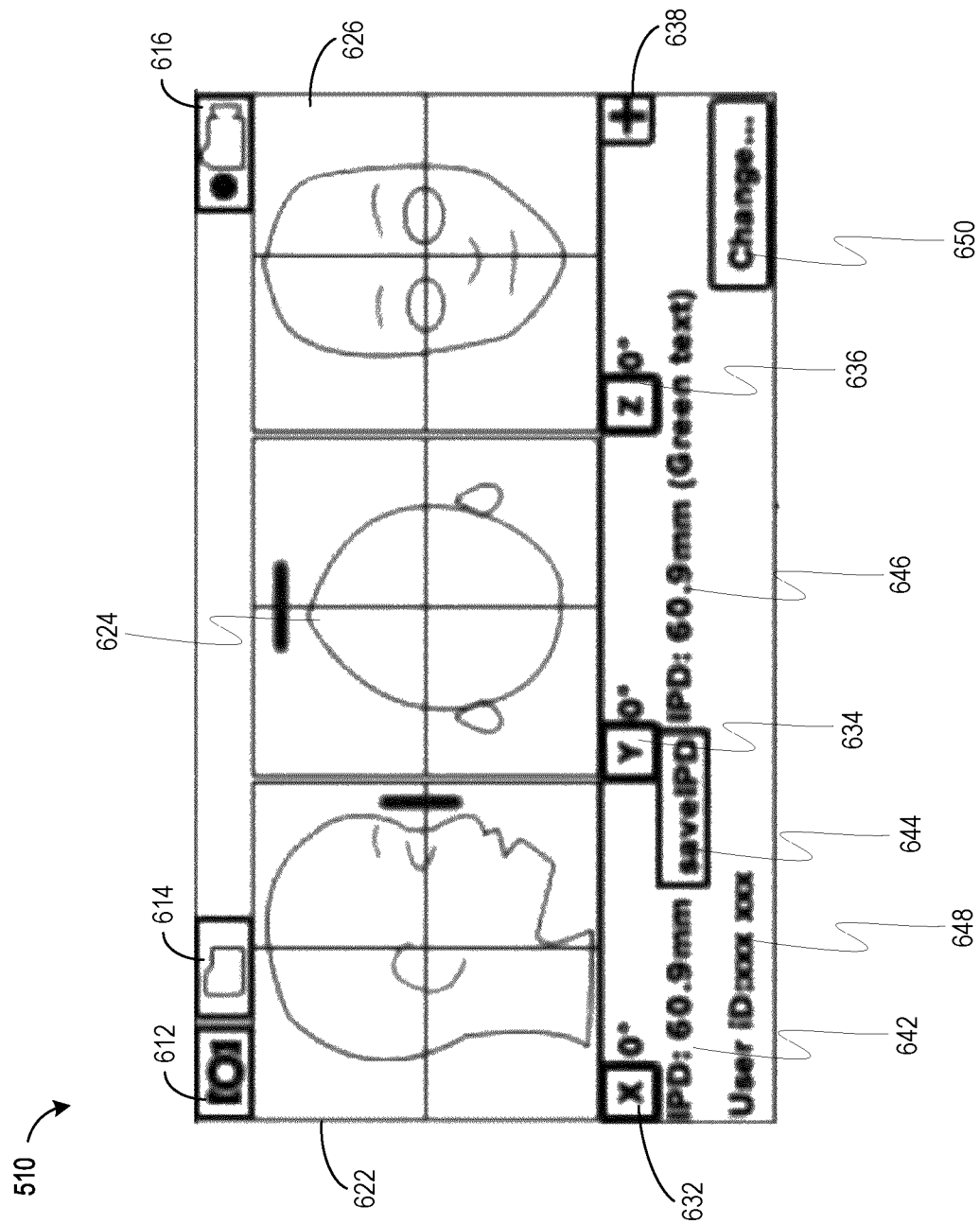
FIG. 6A shows an example embodiment of a subject data window.

Referring now to FIG. 6A, shown therein is an example of the subject data area 510 of the VR test creation interface 400. In the subject data area 510 (e.g., at the top), there may be one or more of: a screenshot button 612, a file window open button 614, and a record scene button 616.

The screenshot button 612, when selected by the user, may render a complete edge-to-edge image on the display 146 and immediately save the file in a .png format inside the current subject data folder, with a filename indicating the current test name (e.g., Worth 4 Dot test), date, and time. Simultaneously a file containing all UI settings when the screenshot was taken may be created as an ".ev" file in the same folder with the same name (except for the file extension).

The file window open button 614, when selected by the user, may launch the current subject folder in the operating system UI so the user can access files and or verify the existence of the files. There may be a preferences file for a given subject that contains at least one of the following information: displacement settings (see FIG. 12), color filter settings (see FIG. 11), blur settings (see FIG. 9), rotation settings (see FIG. 10), and subject saved InterPupillary Distance (IPD). These settings may be updated and then saved every time they are changed.

The record scene button 616, when selected, starts a recording of the subject. The recordings may contain, for example, for every frame (e.g., up to 60 or 100 per second), one or more of the following data: head/controllers position and rotation, user interface settings, eye telemetry data, and eye video. The head/controllers position and rotation may be obtained from sensors in the head unit 112 and the hand unit 118. The user interface settings may be the settings saved by the user during operation of the VR test application 160. The eye telemetry data and eye video may be obtained from the left eye tracking sensor 124 and the right eye tracking sensor 126.

In the subject data area 510 (e.g., in the middle), there may be an X real-time head rotation indicator 622, a Y real-time head rotation indicator 624, and a Z real-time head rotation indicator 626, which indicate the position/movement of the subject's head in the X, Y and Z axes. If the user selects one of the indicators 622, 624, and 626 when tracking is performed on the subject, this will pause the tracking functionality (e.g., for the particular axis selected). Likewise, if tracking is paused for a particular axis, the user can select one of the indicators 622, 624, and 626 to continue tracking in that particular axis. Crosshairs may be shown in one of the indicators 622, 624, and 626 for reference (e.g., to a central position of the head). A bar, which may have a color, such as red for example, may be displayed within at least one of the indicators 622, 624, and 626 to show the relative position of a visual stimulus compared to the orientation of the subject's head during vision testing. In other embodiments, another object may be used instead of a bar to show the relative position of the visual stimulus.

Associated with each of the real-time head rotation indicators (e.g., below them), there may be corresponding toggle indicators: an X toggle indicator 632, a Y toggle indicator 634, and a Z toggle indicator 636 that can be used to obtain a measurement along one of the axes during testing. For example, three "camera heads" icons may be displayed in the subject data area 510, indicating that real-time rotation in the x, y, and z axis are being displayed and tracked, along with cross hairs and text displaying the degrees of rotation in the corresponding axis. The toggles 632, 634, and 636 indicate the axis for which each degree corresponds, and when any of the toggles 632, 634, and 636 are selected by the user and toggled off, the real-time update of the visual indication is stopped, which allows the user to read a prior degree setting at a certain point during a vision test. To continue the real-time update, the user can select the toggle that was toggled "off" so that it is now toggled "on".

For example, there may be three windows showing a head oriented straight on, from the profile, and from the top down. These may show the exact rotation of the head in real time. They may be paused by clicking on them, which then causes them to freeze in place at the rotation when clicked. A small red line in the Y and Z windows may show the relative position of the target test stimulus for reference.

Figure 6B:
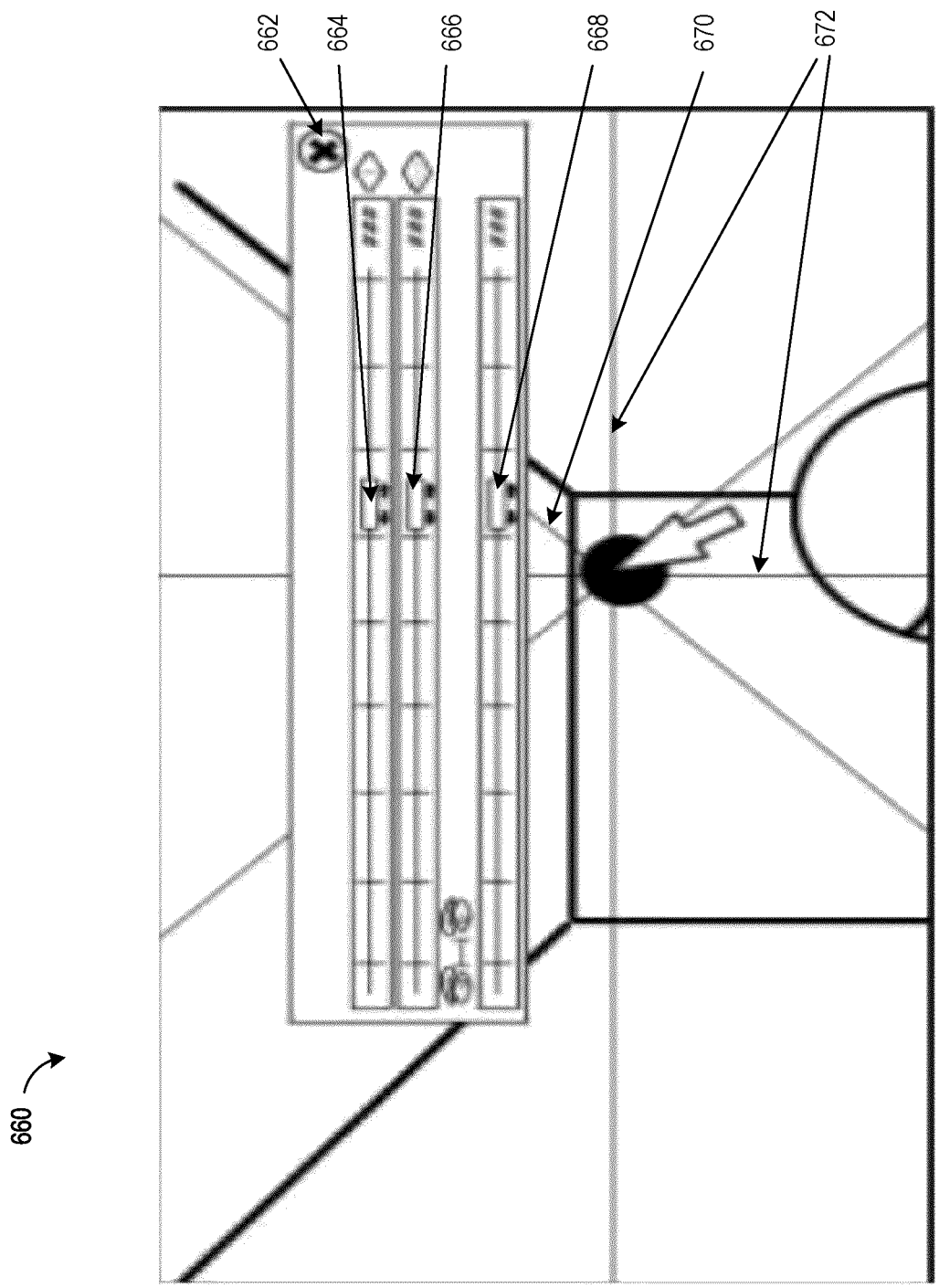
FIG. 6B shows an example embodiment of a portion of a user interface for a virtual laser pointer adjustment.

In the subject data area 510 (e.g., at the right), there may be a laser pointer adjustment button 638 (which may also be referred to as an "edit laser toggle calibration sliders button"). The laser pointer adjustment button 638 may, when selected by the user, reveal a laser pointer adjustment UI 660 with three sliders allowing for width, height, and IPD compensation to calibrate the screen for the laser pointer (as shown in FIG. 6B). The sliders may be used to adjust the position of the laser pointer relative to the mouse. Adjustments may be necessary as the monitor resolution and resolution of the headset as well as the IPD may affect the laser pointer tracking precision. The adjustments may be made, for example, when not running the program in full screen mode, or when the headset or monitor hardware is changed and resolutions are different than before in either device.

To position the VR laser pointer at the appropriate location of the displays 114 and 116 in the head unit 112, the computer 140 may, for example, take as input values corresponding to the display part of the screen height/width in pixels for each side of the display 146, and make a calculation that is relative to the width/height of the head unit 112 in order to properly position the laser pointer under the mouse pointer on the display 146 so that the laser pointer appears similarly in the head unit 112 on either eye. Calibrating the display 146 for the laser pointer may require the collection of the input values by the manipulation of three sliders, as the user then only has to make the visible rectangles take up as much space as possible without overlapping. The computer 140 stores the values, and as long as the software is run on the same computer 140 with the same head unit 112, further adjustments may not be necessary.

The laser pointer adjustment UI 660 may be a window having one or more of a close button 662, a width adjust slider 664, a height adjust slider 666, and an IPD offset slider 668. The width adjust slider 664 and height adjust slider 666 adjust the width and height of the boxes that appear, for example, in both the left and right sides of the monitor. One objective may be to make the boxes as wide and as tall as possible without going over a width limit or over a height limit. The IPD offset slider 668 centers the boxes based on the current IPD. There may be, for example, slight "cross hairs" 672 on the computer monitor, such that the centers of the large X 670 in each box line up with the center of the cross hairs on the left and right sides respectively.

The laser pointer adjustment UI 660 may be used, for example, to make adjustments more than once if the IPD varies from subject to subject, while the width/height may remain the same once the hardware is set and does not change. Settings may be saved as they are changed. When complete, the close button 662 may be selected by the user to close the 3 sliders window.

In a particular implementation, the current real-time hardware device IPD reported by the VR test application software 160 can be displayed below the three rotating heads in millimeters to a precision of 1/10th of a millimeter. Other degrees of precision may be used, whether greater such as 1/100th of a millimeter or lesser such as 1/2 of a millimeter.

In the subject data area 510 (e.g., at the bottom), there may be one or more of: IPD real-time text 642, a save current IPD button 644, saved IPD text 646, subject ID text 648, and a change subject button 650.

The save current IPD button 644 may allow the user to store the current real-time IPD as a preference for the specific subject. As each subject may have their own IPD setting, this allows a quick reset of the IPD so the user can ensure the hardware IPD setting is consistent across visits. If the saved IPD and the current real-time IPD do not match, the current real-time IPD text, such as saved IPD text 646, can turn red, from its original light grey color. It can return to green when the current real-time IPD is adjusted and matches the saved IPD setting, indicated, for example, directly to the right of the save current IPD button 644 in similar but green text.

As an example, on HTC VIVE™, the hardware IPD setting is controlled by a small dial on the headset itself. This may or may not be programmatically controlled. When it is not, the system 100 can read its current setting and save it in the subject preferences, for future reference. To ensure a consistent IPD setting for the subject, once the IPD is set to where the subject prefers it, the save current IPD button 644 may be pressed, and then whenever that subject is loaded into the system in the future, it can be noted whether the current IPD matches their previously chosen IPD setting. If they do not match, the IPD text turns red. When they do match, the IPD text turns back to its default white color.

The change subject button 650 may be used by the user to change the subject at any time (with the exception of during recording and playback) to a different subject. Pressing the change subject button 650 may generate a prompt to go through the steps of choosing a Subject ID or creating a new one.

Figure 7:
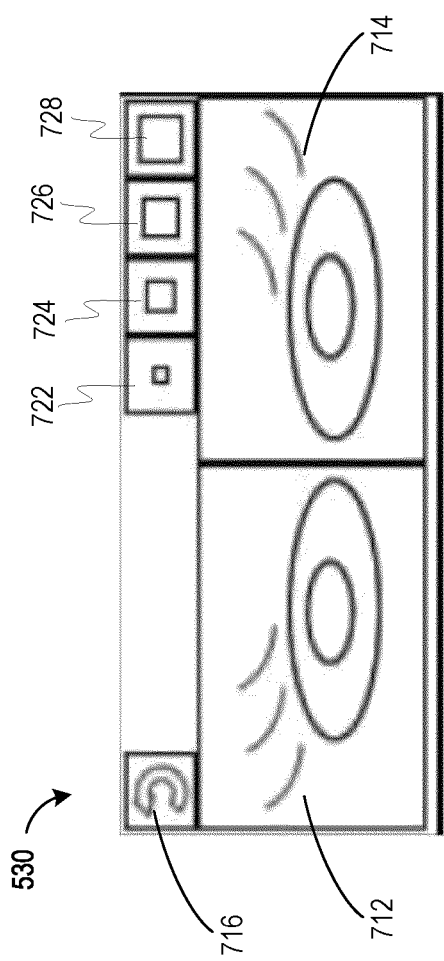
FIG. 7 shows an example embodiment of an eye camera area.

Referring now to FIG. 7, shown therein is an example embodiment of the eye camera area 530 of VR test creation interface 400.

In the eye camera area 530, there may be one or both of a left eye video display 712 and a right eye video display 714. In development mode or during use, for example, white areas or previous (or stock) images may represent the left and/or right eye videos. In development mode, during VR testing or during recording playback, for example, actual video of the left and/or right eyes may be displayed. The actual video may, for example, come from the left eye tracking sensor 124 and/or the right eye tracking sensor 126, or from one or more cameras within the head unit 112. If the corresponding eye tracking sensor allows, pupil size in mm may be displayed.

The eye camera area 530 may be configured to display videos of the subject's eyes if they are available, and if not this area may just be blank. The eye camera area 530 may have, for example, 4 sizes from very small to approximately 700 px wide proportionate to contain two 4×3 aspect ratio video windows.

The eye camera area 530 may have a refresh button 716 (e.g., near the top-left corner) that may be programmed to retry the connection to the hardware video stream (e.g., from a camera) if it has become disconnected and reconnected for some reason.

In the eye camera area 530, there may be one or more toggle buttons (e.g., at the top right) that can be selected by the user to resize the eye camera window between its largest and its smallest settings. These toggle buttons may include, for example, a smallest resize button 722, a small resize button 724, a medium resize button 726, and a largest resize button 728.

The eye camera area 530 may be, for example, located just above the bottom UI and almost all the way to the right, to just before the right edge of the camera settings sliders area 580. There may be a button that the user can select to toggle between showing or hiding the camera settings UI, such as a small down arrow far right of the camera settings UI. There may also be an info button that, when selected by the user, causes a program info screen popup to be displayed (e.g., in the center of the display).

Figure 8A:
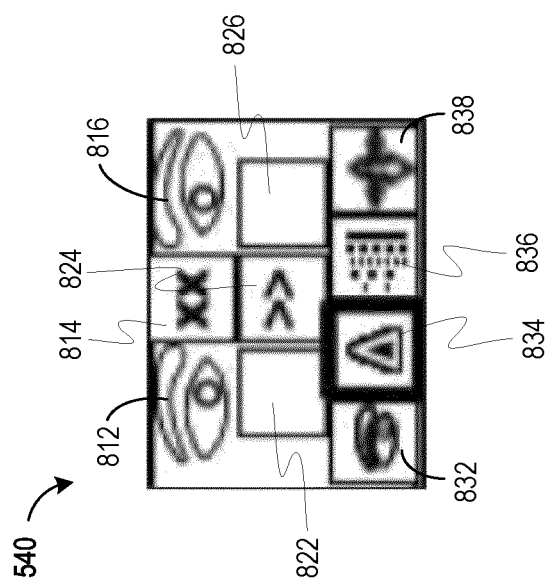
FIG. 8A shows an example embodiment of a main camera settings area.

Referring now to FIG. 8A, shown therein is an example embodiment of the main camera settings area 540 of VR test creation interface 400. In the main camera settings area 540, there may be buttons and toggles that affect camera display and/or launch other settings that may be normally hidden for convenience and clarity. For example, there may be one or more of: a left eye (camera) off button 812; a both eyes off button 814; a right eye (camera) off button 816; a laser pointer on in left eye toggle 822; a swap on/off state in left/right eyes button 824; a laser pointer on in right eye toggle 826; a show blur eye settings button 832; a show eye (camera) rotation settings button 834; a show color filter settings button 836; and a show displacement settings button 838.

The left eye off button 812 and the right eye off button 816 can operate as on/off toggles that, when selected by the user, cause the view of either the left or right eye off to be turned off, showing only a completely black screen on the monitor left/right eye area and/or in the VR headset left/right eye. The both eyes off button 814 may be selected to turn both eyes off or on at once.

The swap on/off state in left/right eyes button 824 may be selected by the user to enable quick switching of which eye of the subject is provided with a VR stimulus during testing. This may enable certain kinds of testing, such as the "swinging flashlight test" (e.g., as long as eye video is available for the user to monitor pupillary response times and the stimulus is sufficiently bright when on).

Figure 8B:
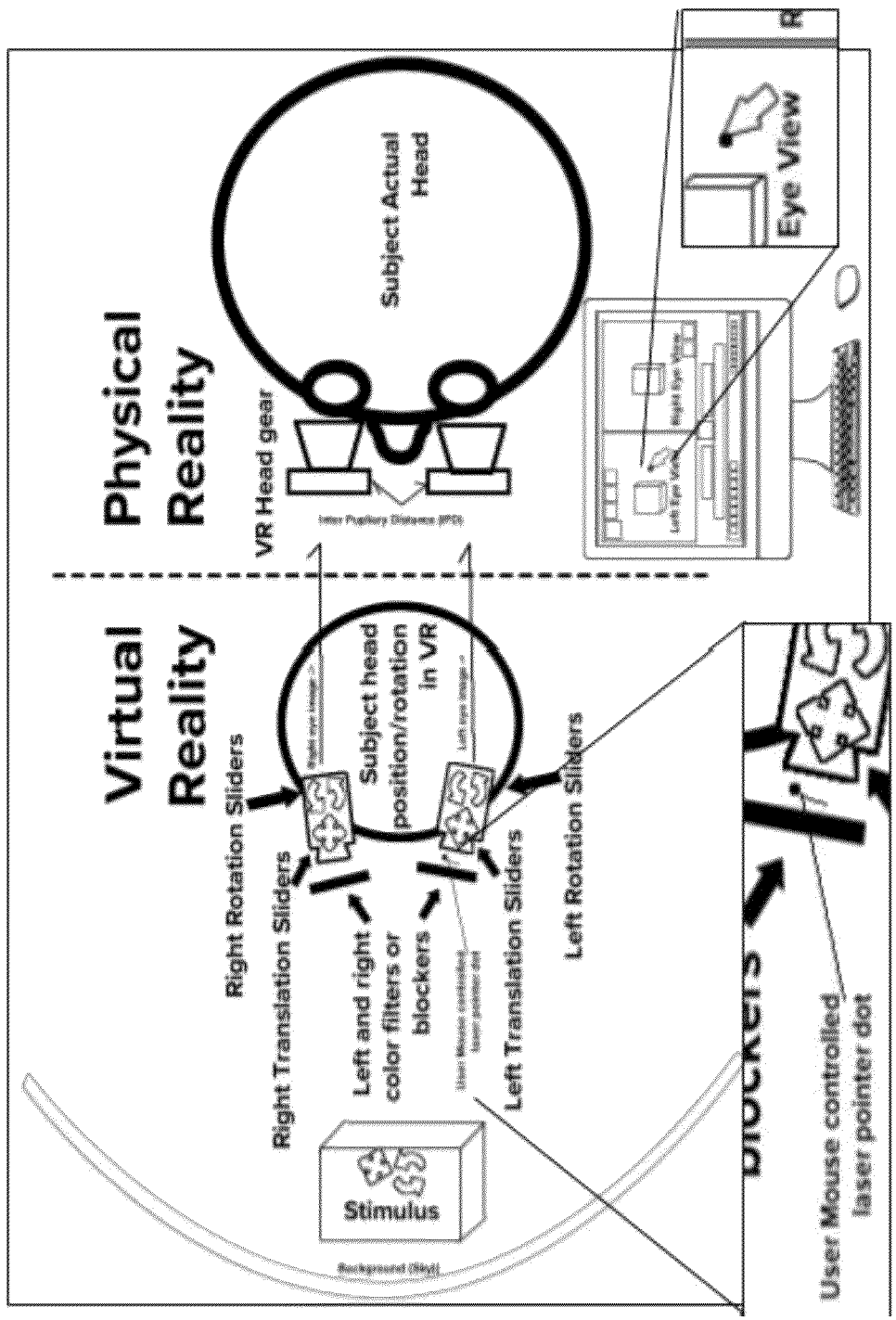
FIG. 8B shows a schematic drawing of an example of a virtual laser pointer simultaneously in VR view and on a computer screen, side-by-side.

The laser pointer on in left eye toggle button 822 and the laser pointer on in right eye toggle button 826 operate as laser toggle buttons and can be selected by the user to show the laser pointer in the left eye or the right eye of the subject during VR testing. The laser pointer can track with the mouse pointer so the user and the subject in VR can see the mouse movements and relative position (of the laser pointer to the mouse). The laser pointer can appear in VR and on the computer monitor simultaneously (as shown in FIG. 8B). Given all the different possible screen sizes and headset specifications, the laser pointer may be calibrated by width/height and IPD compensation. The controls for calibration may be shown in the laser pointer section of the subject data area 510. The user may control the laser pointer so that it is configured to appear in either the left or right eye but not both, due to stereo convergence.

In at least one embodiment, FIG. 8B provides a model functioning of a virtual laser pointer, where the Physical Reality side shows an overhead view of the subject's actual head while wearing the head unit 112. On the other side of the dotted line, the subject's head is recreated in Virtual Reality with the location of the virtual cameras determining the visual image in the videos in the hardware. The virtual cameras, like physical cameras, can be moved and/or rotated, and the VR images in the head unit 112 that are presented to each eye are updated accordingly. The virtual laser pointer appears in both the display 146 (for the user) and directly in front of one of the cameras in Virtual Reality.

The laser pointer may be, for example, a small red sphere that tracks with the mouse, with both the subject and the user being able to see where it is. It may be virtually a few centimeters in front of the subject's eye in VR, such that, for example, it can only be shown to either the subject's left eye or right eye but not both or the subject will attempt to bring it into focus, which can be very uncomfortable for a stimulus that is so close to the eyes. When the user deselects both sides, the laser pointer may be turned off. Its current setting may be saved in the subject preferences whenever it changes. The laser pointer may be a handy communication feature, allowing the user to visually refer to a stimulus and help guide the subject to view certain elements/objects.

Figure 8C:
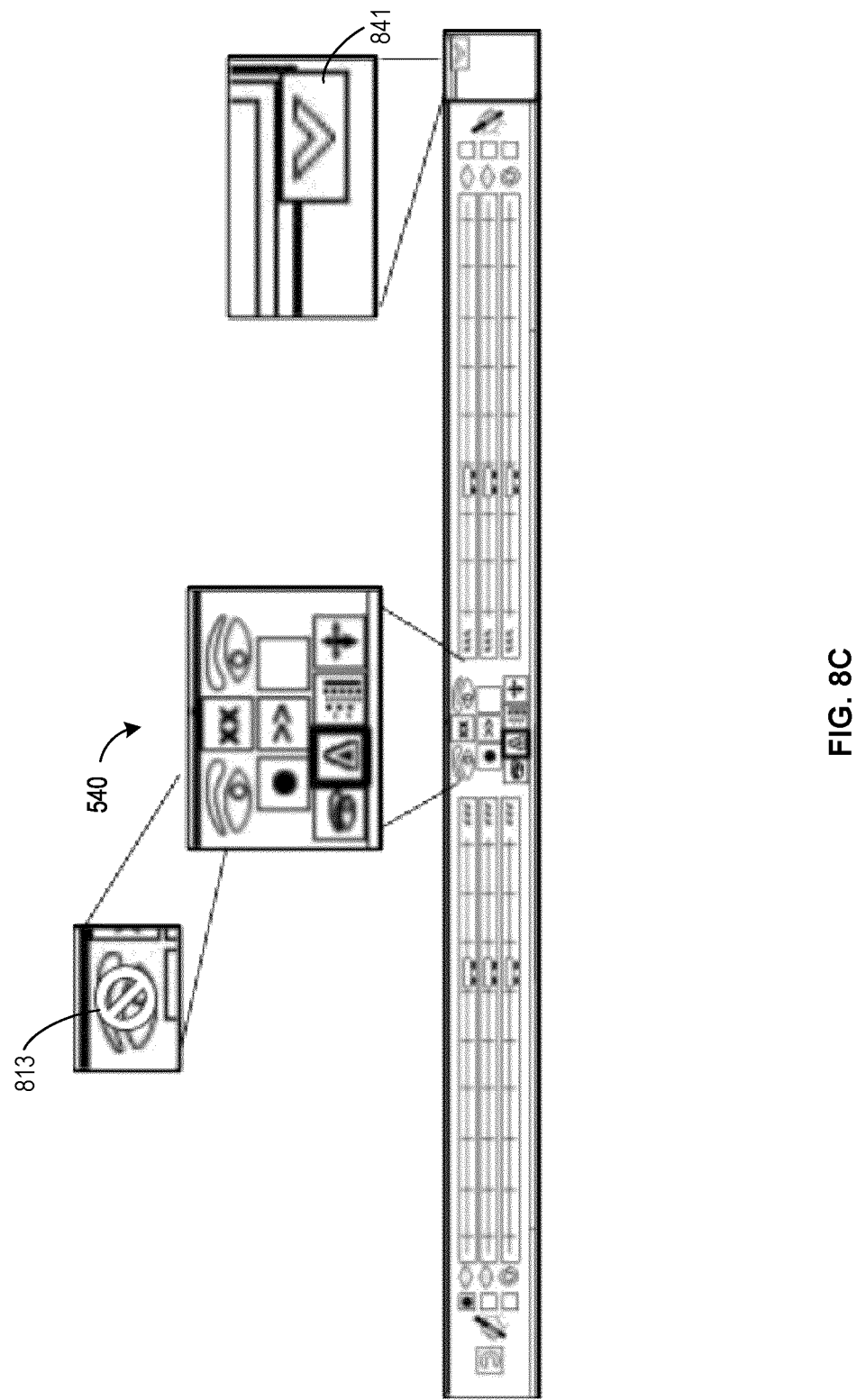
FIG. 8C shows magnified portions of an example embodiment of a main camera settings area integrated with a camera settings sliders area with magnified portions.

Referring now to FIG. 8C, shown therein is an example of the main camera settings area 540 integrated with the camera settings sliders area 580 of VR test creation interface 400 (with magnified portions for ease of reference).

The left eye off button 812 and the right eye off button 816 can be toggled on and off when selected by the user. When the buttons 812 and 816 are in an off position, a cancel icon 813 can be overlaid on these eye off buttons (or a similar means may be used to indicate that they are off).

There may be a collapse camera settings button 841 located, for example, at a corner of the camera settings sliders area 580. When the collapse camera settings button 841 is selected by the user, it causes the camera settings sliders area 580 to collapse or disappear from view.

Figure 9:
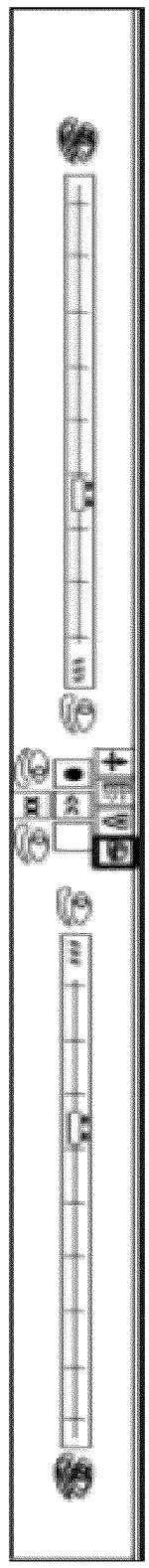
FIG. 9 shows an example embodiment of show blur eye settings sliders.

When the show blur eye settings 832 is selected by the user, the camera settings sliders area 580 may display (or toggle on/off) a specific set of sliders (for each of the subject's eye) relating to eye blurring that can be accessed and altered. An example of these, the show blur eye settings sliders 900, is shown in FIG. 9.

The show blur eye settings sliders 900 (e.g., one for the left eye and one for the right eye of the subject) may be used to apply a Gaussian blur to everything in the VR Headset corresponding to the selected eye of the subject. For example, this can be implemented such that the higher the slider value, the greater the blur effect. The blur effect can be used to remove stimulus detail while maintaining general light levels for certain kinds of assessment. Blur settings can be continuously saved to the specific user's preference file in their data folder whenever they are changed.

The show blur eye settings sliders 900 may be used in ophthalmologic testing, where it may be necessary to obscure detail but not light levels in one eye of the subject or the other for testing purposes. With this setting, the user can provide "blurring" in the VR stimulus that is presented to one or both eyes of the subject or put a portion or all of the VR stimulus out of focus to a specific intensity. This setting may be updated on change and saved in the subject preferences.

For example, subject-specific preferences may be saved in a subject preferences file when the show blur eye settings sliders 900 are changed, such that when the subject returns later, the last settings used with that particular subject are loaded from the subject preferences files and set so that assessment can continue from where it left off in the last test session. The settings of the sliders, accessible from the main camera settings area 540 (as shown in FIG. 8A), and toggle buttons may be saved separately from the protocols. The sliders in the test-specific settings, as well as the VR environment, the VR stimulus rotation, and which test is to be displayed, may be saved separately to a particular protocol data file.

Figure 10:
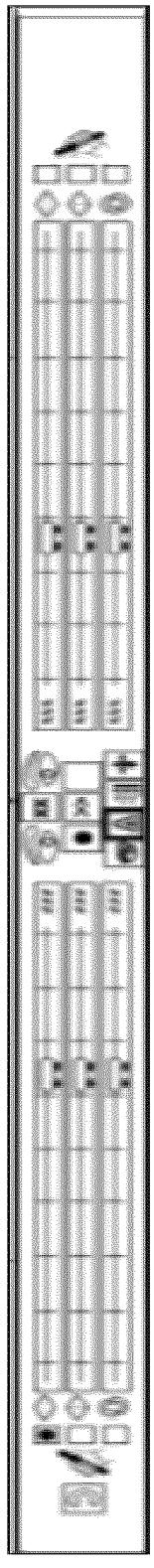
FIG. 10 shows an example embodiment of show eye camera rotation settings sliders.

When the show eye (camera) rotation settings 834 is selected by the user, the camera settings sliders area 580 may display (or toggle on/off) a specific set of sliders (for each eye) relating to eye (camera) rotation that can be accessed and altered by the user. The show eye rotation settings 834 may be referred to as diopter settings. An example of these, the show eye camera rotation settings sliders 1000, is shown in FIG. 10.

The show eye camera rotation settings sliders 1000 may be used by the user to alter the rotation of each eye camera in the x, y, and z rotational axes. There may then be a total of 6 sliders, one for each axis on each eye. Numbers indicating the "diopter" converted from degrees may be indicated next to the horizontal and vertical sliders. Diopters are normally thought of as how glass prisms indicate strength, but in this case they may correspond by a fractional amount to degrees of turn in a given axial plane. The third slider, torsional rotation, is indicated in degrees and is unrelated to prisms.

The show eye camera rotation settings sliders 1000 may be used by the user to adjust rotation settings (prismatic/torsional), where each eye camera in VR can be rotated around the x, y, or z axis up to + or − some maximum number of degrees (e.g., where in the display degrees are converted to diopters). This, like holding prisms in front of an eye, can either simulate a turn or help indicate how much of a turn a patient has horizontally, vertically. Additionally, torsional rotation can be altered, which is not a prismatic effect but possible in VR as virtual eye cameras are rotatable in all three orientations. Rotation settings may be saved whenever they are changed to the subject's preference file. Sliders for each eye may represent horizontal, vertical, and torsional rotation. Next to each slider may be a "VR control" toggle where, if selected, the VR controller thumb pad enables the subject to move that particular slider back and forth with thumb movements.

Figure 11:
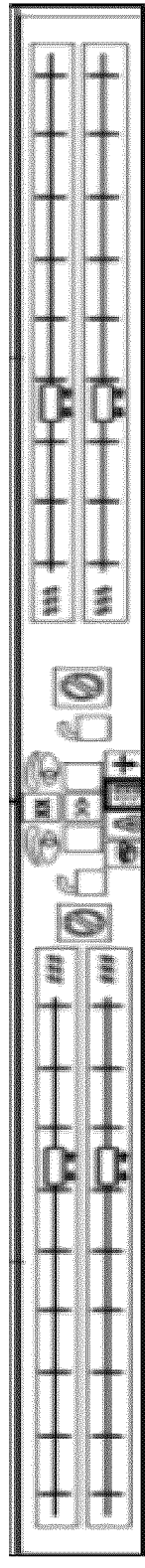
FIG. 11 shows an example embodiment of show color filter settings sliders.

When the show color filter settings 836 is selected by the user, the camera settings sliders area 580 may display (or toggle on/off) a specific set of sliders (for each eye) relating to a color filter that can be accessed and altered. An example of show color filter settings sliders 1100 is shown in FIG. 11.

The show color filter settings sliders 1100 may be adjusted by the user to set a color filter over the left and/or right eye. One slider for each eye can allow the user to select a color value in nanometers that correspond approximately to light wavelength so that the user can control which colors are filtered in a VR stimulus to each eye of the subject. It is possible that RGB color values set by the sliders may not necessarily match the color wavelength precisely as not all wavelengths of light can be accurately represented by the RGB color space available on computer hardware, but if future hardware becomes capable of displaying a wider color gamut this will not affect the function of the design. The other slider for each eye can be used to adjust the intensity or amount of filtering applied to the VR stimulus that is presented to each eye of the subject during VR testing. Lock buttons, when toggled on by the user, allow the movement of one slider on one side to move the same amount as a corresponding slider on the other side so that the VR stimuli sent to both eyes have the same filter setting. As with the other sliders, these color filter slider settings can be saved in the subject's data file whenever they are changed.

The show color filter settings sliders 1100 may be used to adjust color filter settings, for example, to enable the user to set a color filter that is applied to a VR stimulus for each or both of the subject's eyes during VR testing. The top slider may be used by the user to control the color wavelength in nanometers (e.g., approximately, as not all color wavelengths can be replicated on a computer monitor) and the bottom slider intensity in percent. It has been theorized that certain color filters may assist subjects with certain forms of colorblindness, and this functionality may allow for experimentation in that regard. The settings for the show color filter settings sliders 1100 may be changed based on the subject's preferences and then saved to the subject's preference file. Pressing the lock toggle button on either side of the screen may make the sliders synch to each other so the VR stimuli shown to both eyes are equally affected simultaneously.

Figure 12:
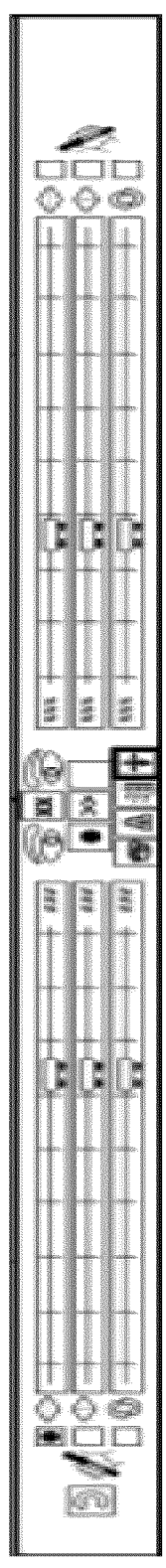
FIG. 12 shows an example embodiment of show displacement settings sliders.

When the show displacement settings 838 is selected by the user, the camera settings sliders area 580 may display (or toggle on/off) a specific set of sliders (for each eye) relating to displacement that can be accessed and altered. An example of these, the show displacement settings sliders 1200 is shown in FIG. 12.

The show displacement settings sliders 1200 may work similarly to the diopter settings sliders and look nearly identical, with the main difference being that they translate the camera in distance along the x, y, or z axis. The amount of translation may be indicated in millimeters next to each slider. When moved, like all the other sliders, these slider values can be individually saved to the subject's data file for reloading when the subject returns later.

The show displacement settings sliders 1200 may enable the user to adjust displacement settings, where each eye camera in VR can be translated along the x, y, or z axis up to + or − some maximum number of millimeters. This can extend either the maximum or minimum IPD by moving the foveal center point past the maximum or minimum physical IPD setting on the hardware device, or compensate for eye deformities where they are positioned beyond normal physical locations. Displacement settings may be saved whenever they are changed to the subject's preference file. Sliders for each eye may represent horizontal, vertical, and z depth displacement. Next to each slider may be a "VR control" toggle where, if selected by the user, enables the subject to use a VR controller thumb pad or stick to move that particular slider back and forth with thumb movements.

In at least one embodiment, next to each slider may be a toggle for VR controller control. If selected, moving the thumb on the LEFT or active VR controller (if only one is present and it is indicated as RIGHT or LEFT) can move the slider value up or down, allowing the subject to gently adjust the setting of the selected slider. A reset button can put all sliders back to zero. Whenever slider values change, their value can be saved to the subject preferences file and can be reloaded when the subject is reloaded into the system later.

Figure 13:
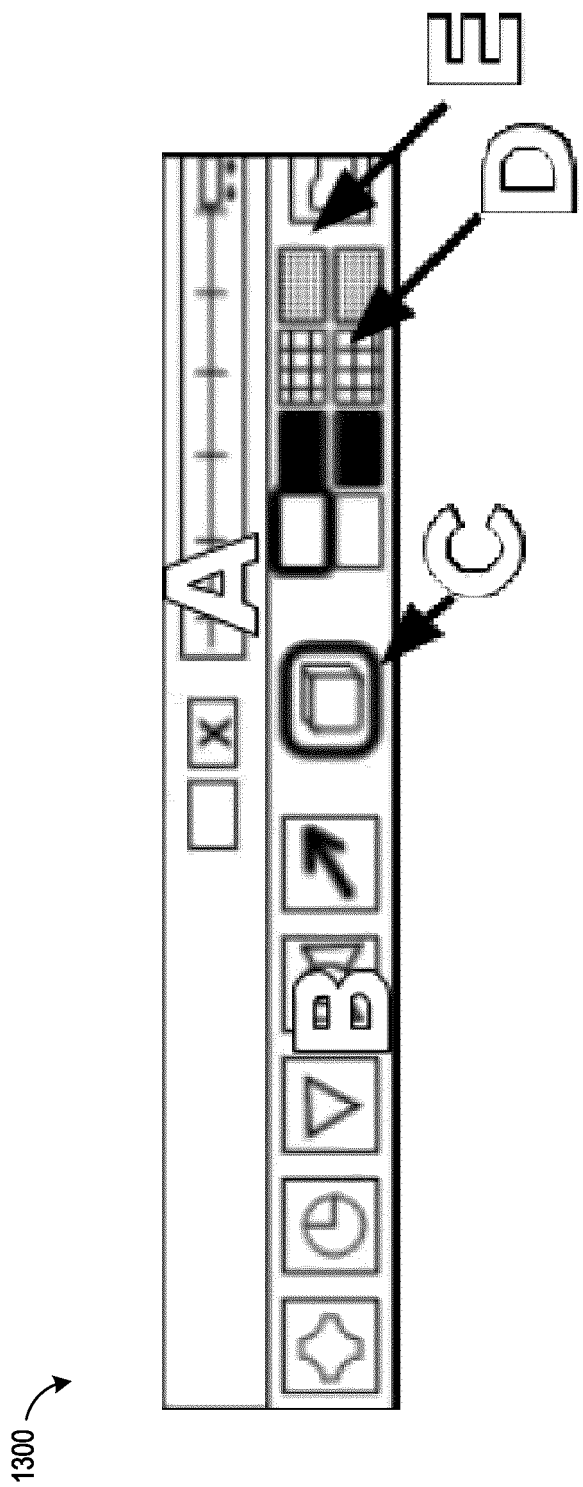
FIG. 13 shows a letter-coded screen image of an example embodiment of a test settings area.

Referring now to FIG. 13, shown therein is a letter-coded screen image of an example embodiment of the test settings area 1300 of VR test creation interface 400.

The UI for each test may be created or shown in the test-specific UI area 550. Each VR test may consist of some kind of visual stimulus that may be based, for example, on one or more of the gold standards in ophthalmic testing. The VR stimulus may be "attached" to the head rotation or not attached, depending on the test requirement, and the VR position of the stimulus may always move with the position of the subject's head. If attached using the rotation lock button, the VR stimulus may always appear directly in front of the subject's face at the exact specified distance no matter where they turn their head. If not, it may still remain the specified distance but not necessarily in front of the subject's face.

Each test may be represented by an icon that is a button graphic, but may also appear in the top left of the user interface, and as the current protocol if the given test is the one that is being currently displayed by the protocol.

Test settings may all appear, for example, in the part of the interface that is directly above the test and protocol selection buttons, but directly below the subject visual settings controls.

In general, the settings may be what are recorded by the protocols and relate to what VR stimulus needs to be presented to the subject to conduct a given VR vision test.

The "general settings" are defined as those settings that are recorded by the protocols and relate to what VR stimulus needs to be presented to the subject to conduct a given VR vision test. In development mode, a developer may, for example, select GUI elements and associate functionality (e.g., scripts, code, triggers, events, procedures) with them to develop a VR vision test. The general settings may include one or more of:

(A) Test specific settings: these settings may change depending on which test is selected.

(B) Test selection: these buttons may indicate which VR tests are available and which one is currently selected.

(C) Test stimulus settings window launch: this may be used to open a test stimulus settings window, which allows selection of the position and rotation of the test VR stimulus relative to the subject's head in any or all three axes (x,y,z rotation and position).

(D) Room colors: these may be used to define the colors of the "room" or virtual walls, floors, and small objects that are apparent in the room in which the subject is located in VR. If none of these are selected, there is no room displayed (i.e., no walls, floor, or objects), and only the skybox appears.

(E) Skybox colors: these may be used to define the colors of the "skybox" or distant sky and horizon at infinity. This may represent the inside of a giant sphere at visual infinity where the subject is effectively at its center. For example, this sphere cannot be turned off, but it can appear totally black or totally white rendering it non-apparent.

In at least one embodiment, the user may develop VR tests that achieve the same goals as the gold standard tests, but can be delivered more effectively. The UI for a newly developed test may be created in the test-specific UI area 550. The user may, for example, integrate "Art" into the tests so researchers can more fully customize the VR environment for subjects, and the concept of integrating clinical tests into character-driven stories may be realized.

Figure 14A:
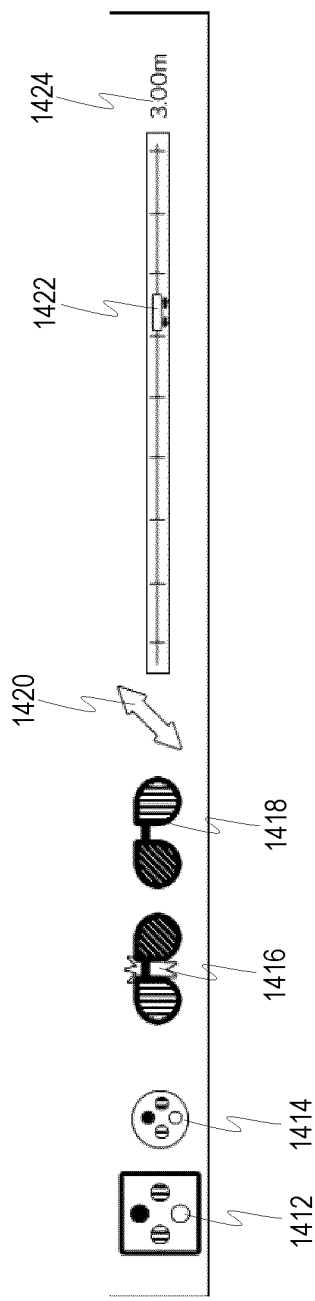
FIG. 14A shows an example embodiment of a test-specific UI area for a Worth 4 Dot VR test.

Referring now to FIG. 14A, shown therein is an example embodiment of the test-specific UI area 550 of VR test creation interface 400 for a Worth 4 Dot test. The Worth 4 Dot VR test is a VR approximation of the real-life Worth 4 Dot test. The Worth 4 Dot (WFD) test may be used for the assessment of eye function. For example, two different VR stimuli, a larger square and a small flashlight sized one, may be shown to the subject while the subject is "virtually" wearing red and green filters over their eyes.

In the test-specific UI area 550, there may be one or more (e.g., from left to right) of: a large WFD stimulus toggle button 1412; a small WFD stimulus toggle button 1414; a left green, right red camera filter toggle button 1416; a left red, right green camera filters toggle button 1418; a distance indicator icon 1420; a distance slider 1422; and a distance amount text 1424.

Figure 14B:
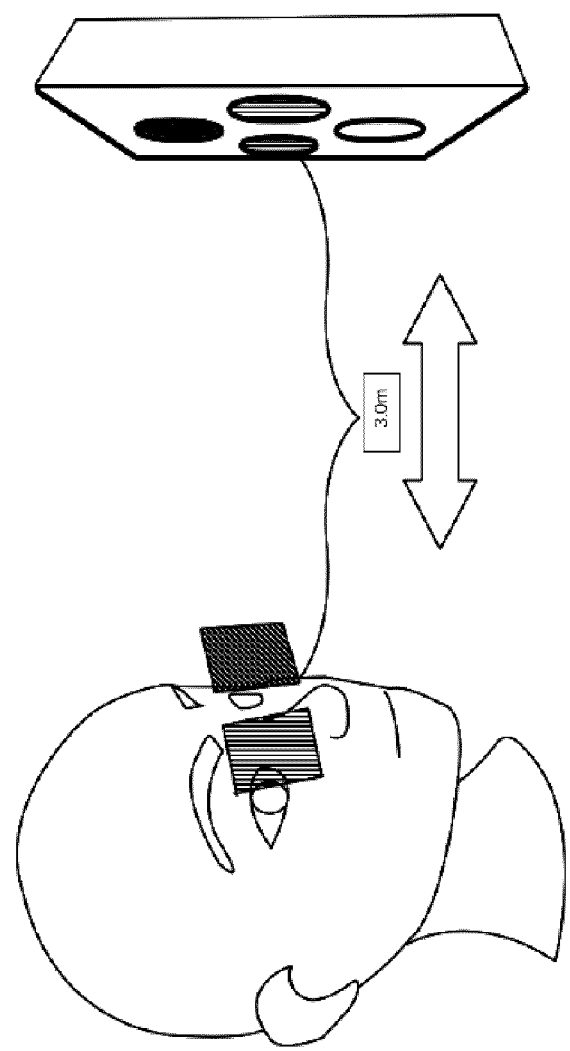
FIG. 14B shows a schematic diagram of an example of the Worth 4 Dot VR test corresponding to the UI of FIG. 14A.

The Worth 4 Dot VR test may be set up by the user using the above elements of the test-specific UI area 550 (e.g., as shown in FIG. 14B). The large WFD stimulus toggle button 1412 and small WFD stimulus toggle button 1414 can be selected by the user during VR vision testing to toggle between large stimulus and small stimulus, with sizes displayed in VR being in compliance with the size of the gold standard WFD test as approximately 20 cm squared for the large stimulus, and 6 cm squared for the small stimulus.

The left green, right red camera filters toggle button 1416 and the left red, right green camera filters toggle button 1418 can be selected by the user during VR vision testing to toggle between providing green filter left/red filter right, green filter right/red filter left, or no filter to the VR stimuli that are presented to the subject.

The distance slider 1422 may be set by the user to a defined stimulus distance for performing the WFD test where such distances may range from about 0.3 m to 6 m.

Figure 15A:
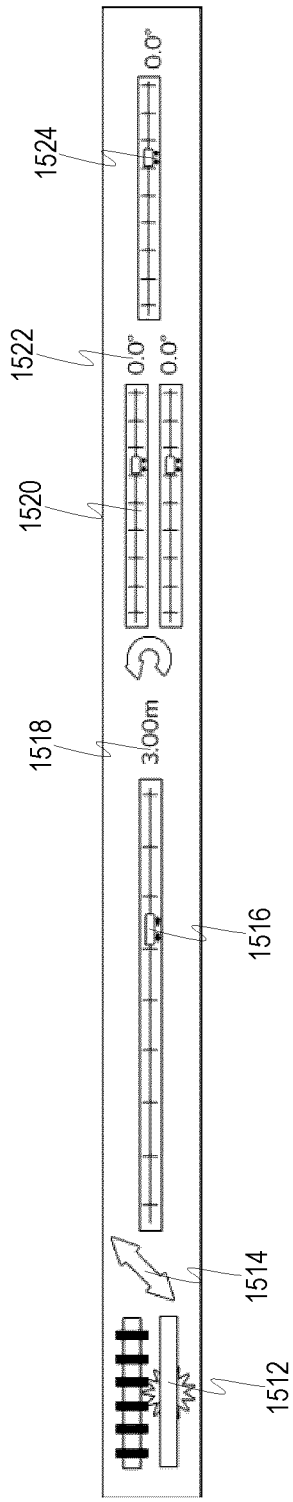
FIG. 15A shows an example embodiment of a test-specific UI area for a Bagolini Striated Lens VR test.

Referring now to FIG. 15A, shown therein is an example embodiment of the test-specific UI area 550 of VR test creation interface 400 for a Bagolini Striated Lens VR test. The Bagolini Striated Lens VR test is a VR approximation of the real-life Bagolini Striated Lens test. The Bagolini Striated Lens test may be used to detect the presence or extent of binocular functions in the subject's eye. For example, this test may show two beams or white rods of light crossed at 45 degrees perpendicular to each other in VR to the subject. One beam may be shown in only one eye of the subject, and the other beam may be shown in only the other eye of the subject. The beams may be individually rotated torsionally.

In the test-specific UI area 550, there may be one or more (e.g., from left to right) of: select gradations or deselect gradations toggle buttons 1512 (e.g., where gradient highlight indicates selection choice); a distance icon 1514; a distance slider 1516; a distance amount input 1518; individual element rotation sliders 1520 (e.g., where top is left rotation, bottom is right rotation); rotation amount inputs 1522 for individual rotation sliders; and an overall rotation amount slider 1524.

Figure 15B:
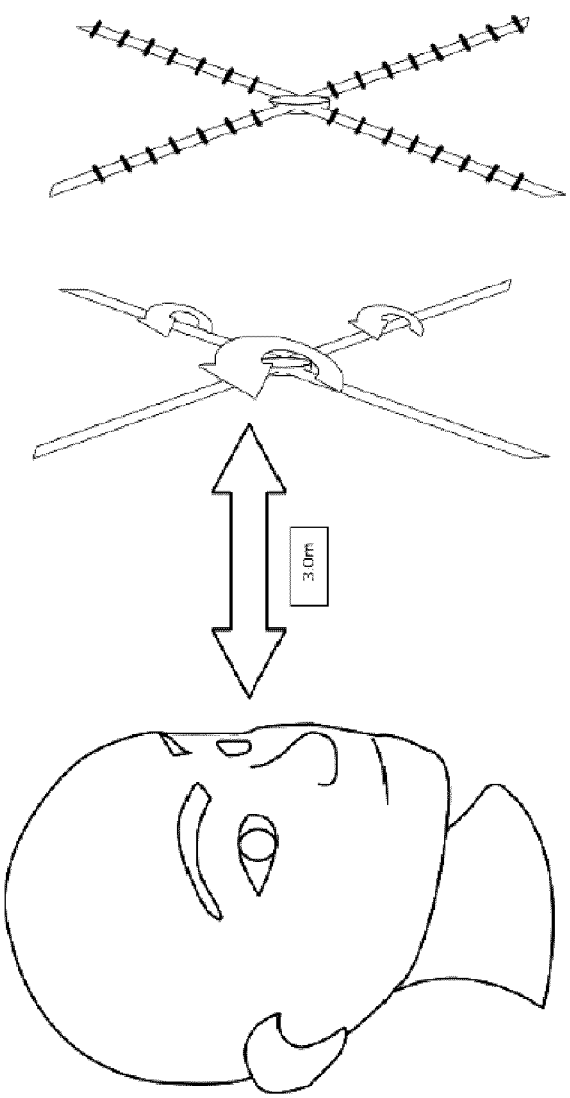
FIG. 15B shows a schematic diagram of an example of the Bagolini Striated Lens VR test corresponding to the UI of FIG. 15A.

The Bagolini VR test may be set up by the user using the above elements of the test-specific UI area 550 (e.g., as shown in FIG. 15B). To set up the test, a user may use the VR test creation interface 400 to put a rotatable thin cylinder in the VR stimulus defaulting at opposite angles to make an 'x', with a centerpoint that appears to both of the subject's eyes.

The select gradations or deselect gradations toggle buttons 1512 can be used to place colored gradations along the length of each long cylinder. The distance slider 1516 can be used to move the entire VR stimulus toward and away from the subject's eyes. The individual element rotation sliders 1520 can be used to rotate the left and right VR stimuli independently. The overall rotation amount slider 1524 can be used to rotate both stimuli simultaneously. It should be understood that whenever the terms left and right VR stimuli are used herein it is understood that they are independently presented to the left and right eyes of the subject, respectively.

Figure 16A:
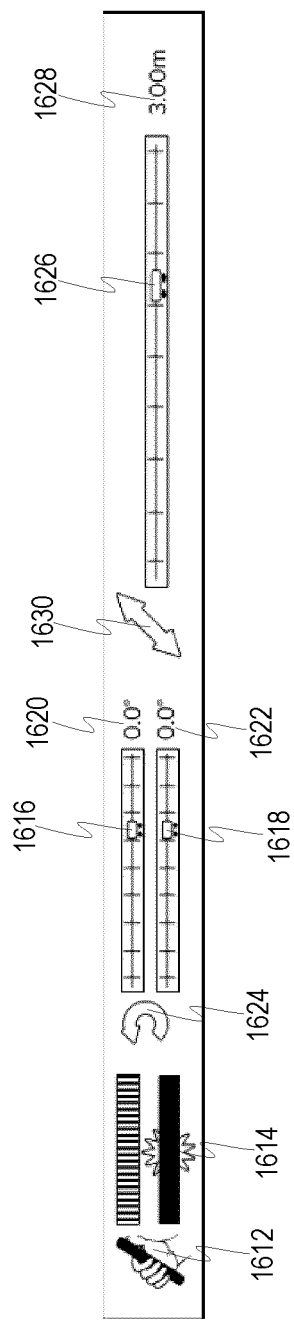
FIG. 16A shows an example embodiment of a test-specific UI area for a Double Maddox Rod VR test.

Referring now to FIG. 16A, shown therein is an example embodiment of the test-specific UI area 550 of VR test creation interface 400 for the Double Maddox Rod VR test. The Double Maddox Rod VR test is a VR approximation of the real-life Double Maddox Rod test. The Double Maddox Rod test may be used to determine cyclodeviations. For example, the test may show one red horizontal rod, and one white horizontal rod VR stimulus to each of the subject's eyes, respectively. The subject may be asked what is the correct rotation that should be applied to one of the rods in the VR stimulus to make it perfectly parallel to the other rod to indicate torsional rotation of their eyes.

In the test-specific UI area 550, there may be one or more (e.g., from left to right) of: a VR control indicator icon 1612; a VR controls red bar and VR controls white bar toggle button 1614; a red bar (top) rotation slider 1616; a white bar (bottom) rotation slider 1618; a red bar rotation amount text indicator 1620; a white bar rotation amount text indicator 1622; a reset rotation button 1624; a stimulus distance slider 1626; a stimulus distance text indicator 1628; and a distance icon 1630.

Figure 16B:
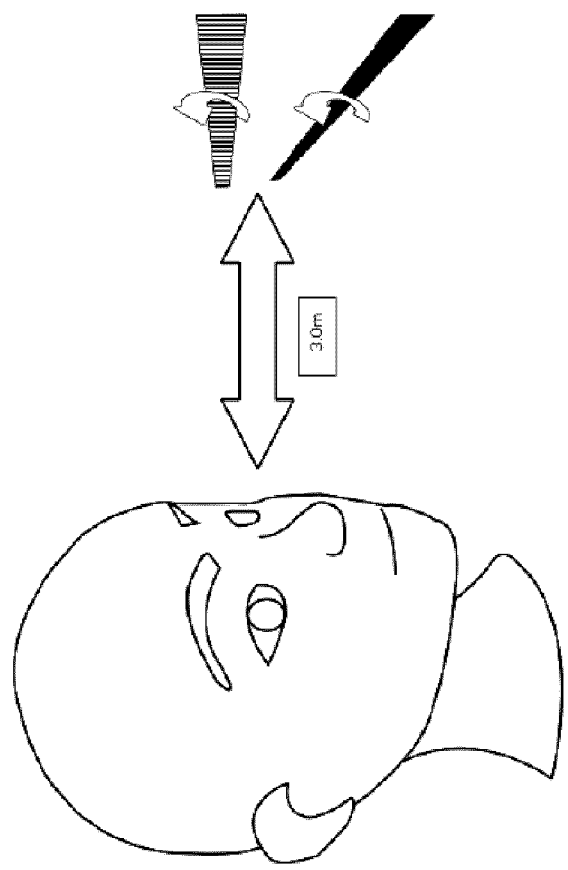
FIG. 16B shows a schematic diagram of an example of the Double Maddox Rod VR test corresponding to the UI of FIG. 16A.

The Double Maddox Rod VR test may be set up by the user using the above elements of the test-specific UI area 550 (e.g., as shown in FIG. 16B). To set up the test, the VR test creation interface 400 may begin by positioning a red rod, and a white rod extended mostly but not entirely across the visual stimulus in each eye respectively so they appear parallel to each other with red above and white below.

The VR controls red bar and VR controls white bar toggle button 1614 can be used as a toggle for VR controller triggers to rotate either the red or white stimulus. The red bar (top) rotation slider 1616 and white bar (bottom) rotation slider 1618 can be used to rotate the red or white stimulus. The reset rotation button 1624 can be used to set rotation of both rods in the VR stimulus to zero. The stimulus distance slider 1626 can be used to move one or more of the VR stimuli toward or away from the subject's eyes.

Referring now to FIG. 17A, shown therein is an example embodiment of the test-specific UI area 550 of VR test creation interface 400 for a Contrast Sensitivity and Visual Acuity VR test. The Contrast Sensitivity and Visual Acuity VR test is a VR approximation of the real-life Contrast Sensitivity and Visual Acuity test. The Contrast Sensitivity test may be used to measure the ability to distinguish between finer and finer increments of light versus dark. For example, the Contrast Sensitivity test may provide a chart to show letters that vary from high contrast to minimal contrast and the subject is asked to identify all the letters on the chart while standing in normal lighting conditions. The Visual Acuity tests may be used to measure the ability to see the details of a letter or symbol from a specific distance. For example, the Visual Acuity test may provide a typical letter-based eye chart or a symbol-based eye chart (e.g., for subjects who do not know the roman alphabet) and the subject is asked to identify all the letters or symbols on the chart.

In the test-specific UI area 550, there may be one or more (e.g., from left to right) of: a scale icon 1712; a scale amount slider 1714; a scale amount text 1716; a distance icon 1718; a distance amount slider 1720; and a distance amount text 1722.

The Contrast Sensitivity VR test may be set up by the user using the above elements of the test-specific UI area 550. To set up the test, the user may use the VR test creation interface 400 to begin displaying a standard letters based contrast sensitivity chart image. The scale amount slider 1714 can be adjusted by the user to resize the object's vertical and horizontal scale. The distance amount slider 1720 can also be adjusted by the user to move the VR stimulus toward or away from the subject's eyes in VR space.

The Visual Acuity VR test may be set up by the user using the above elements of the test-specific UI area 550 (e.g., as shown in FIG. 17B). To set up the test, the user may use the VR test creation interface 400 to display a standard letters based visual acuity chart image. The scale amount slider 1714 can then be adjusted by the user to resize the object's vertical and horizontal scale. The distance amount slider 1720 can also be adjusted by the user to move the VR stimulus toward or away from the subject's eyes in VR space.

Figure 18A:
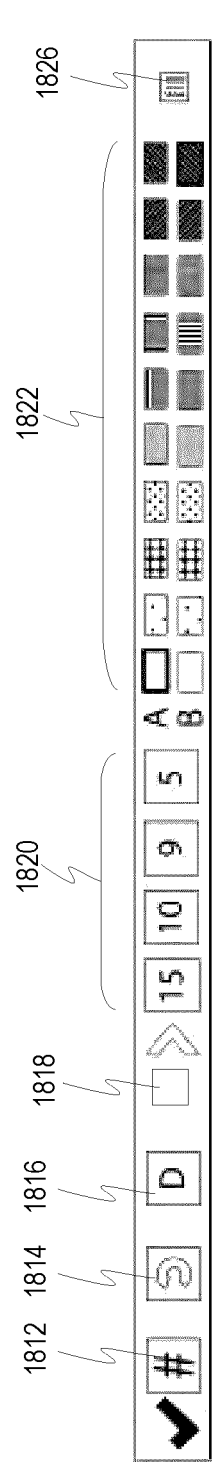
FIG. 18A shows an example embodiment of a test-specific UI area for a Farnsworth D15 VR test.

Referring now to FIG. 18A, shown therein is an example embodiment of the test-specific UI area 550 of VR test creation interface 400 for the Farnsworth D15 VR test. The Farnsworth D15 VR test is a VR approximation of the real-life Farnsworth D15 color vision test. The Farnsworth D15 test (or Farnsworth-Munsell 100 hue test) may be used to test color sensitivity. For example, the subject is presented with a VR stimulus comprising several discs at varying hues. The subject may be asked to arrange the discs in order of hue, starting with a particular one, placing discs in order of similarity to the original hue from left to right.

In the test-specific UI area 550, there may be one or more (e.g., from left to right) of: a show numbered order toggle button 1812 (which overlays numbers on the arrangeable color discs in VR view displaying the correct numeric order as opposed to the order of placement by the subject); a refresh current test button 1814 (which resets the test and scrambles the arrangeable color discs); a D15 test toggle button 1816; show/hide advanced custom test controls 1818; a number of discs in test toggle buttons 1820; a Color A toggle button 1822 (e.g., starting at left color); a Color B toggle button 1824 (e.g., starting at right color); and a show or hide rainbow cube in VR toggle button 1826.

Figure 18B:
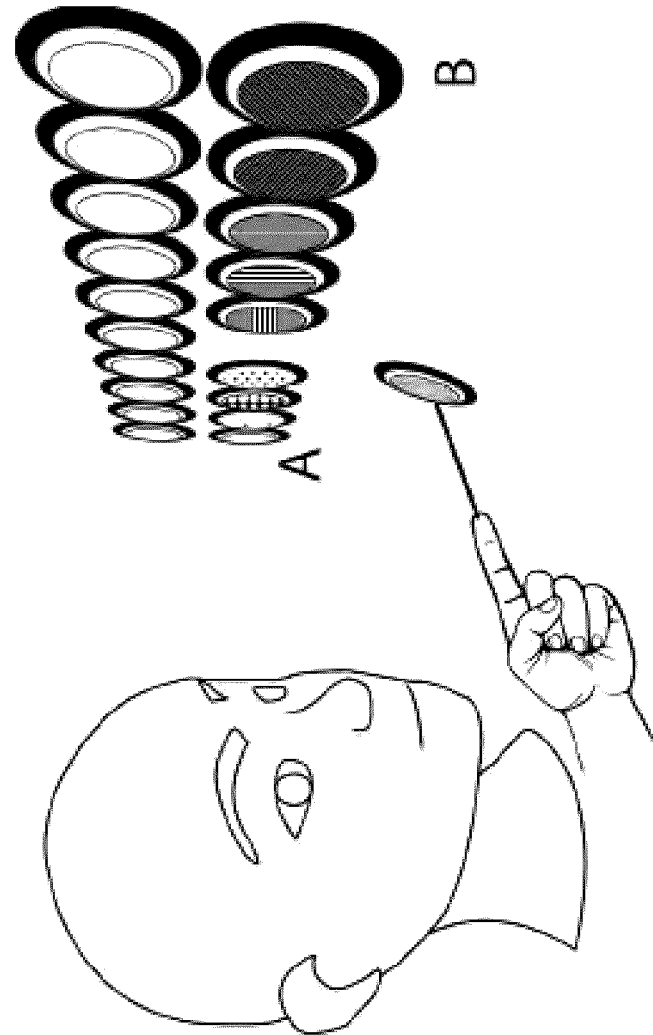
FIG. 18B shows a schematic diagram of an example view of the Farnsworth D15 VR test corresponding to the UI of FIG. 18A.

The Farnsworth D15 VR test may be set up by the user using the above elements of the test-specific UI area 550 (e.g., as shown in FIG. 18B). To set up the test, the user may use the VR test creation interface 400 to display a VR stimulus having a series of small color discs that can be dragged by the subject from a lower row to an upper row. The objective for the subject is to use the VR controller (with a small pick-up/drop object like an antenna at the end of it) trigger button to pick up and drop colored circles above the bottom row but in the proper order from left hue to right. The specific pick up and drop control may vary with the VR system hardware capabilities.

The show numbers toggle 1812 can be used to display numbers indicating the proper order of hues on or off in the subject's field of view in VR. The refresh current test button 1814 can be used by the user to reset the test. The D15 test toggle 1816 can be used by the user to select and set up the standard Farnsworth D15 test. The show/hide advanced custom test controls 1818 can be used by the user to open up other options for color selection; and toggling may show/hide related buttons. The number of discs in test toggle button 1820 can be used to set the number of color hues in the test, such as 15, 11, 9, or 5. The color A toggle button 1822 and the color B toggle button 1824 can be used to set the extent of hues for the custom test and intervening colors may be calculated mathematically between those two extents. The show or hide rainbow cube in VR toggle button 1826 can be used to display a rainbow gradient cube toggle to show colors of the rainbow in the context of the VR test, which may help illustrate the effects of color filters (e.g., from subject camera controls).

In VR, the subject may see the normal controllers and the color discs in a row with their order set at random. Using a VR controller, the subject may put the end of a small rod "inside" each disc, press the trigger to "pick up" the disc, and then drop it on a semi-transparent disc in the row directly above it.

In VR, the subject may initially see color discs that have black rings around them and a select/drag antenna, so that the subject can then select drag targets that are transparent but easily visible, as shown in FIG. 18B. FIG. 18B may also be used as a model for creating or performing a variation of the Farnsworth D15 test that generates VR visual test stimuli based on a specified range of colors.

An example of what the subject sees and/or does in VR while being tested is shown in FIG. 18B, which may include one or more of:

(A) colored discs presented in VR for the subject to select and move by pressing a trigger button;
(B) a trigger button for selecting or moving colored discs;
(C) attaching a disc by holding the trigger button down and moving the tip of the rod at the end of the controller into a disc;
(D) matching the disc by moving the disc to a semi-transparent target in the row above, while trying to match the disc to the left as closely as possible; and
(E) placed discs, after all the discs are placed, with the actual numerical order of the discs being displayed at any time.

Figure 19A:
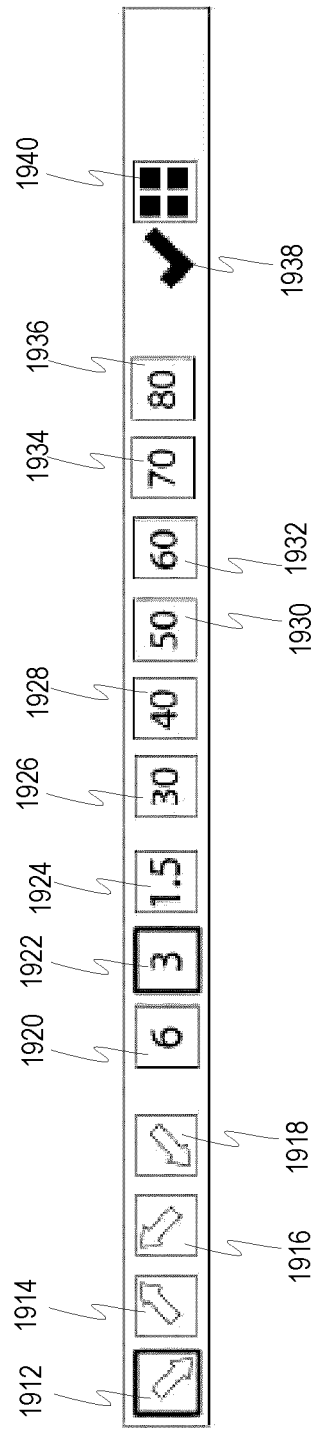
FIG. 19A shows an example embodiment of a test-specific UI area for a Frisby Stereopsis VR test.

Referring now to FIG. 19A, shown therein is an example embodiment of the test-specific UI area 550 of VR test creation interface 400 for a Stereopsis VR test. The Frisby Stereopsis VR test is a VR approximation of the real-life Frisby Stereopsis test. The Frisby Stereopsis VR test may be used to help identify the subject's depth perception ability using only the difference in location between their two eyes. For example, the test may endeavor to remove all monocular cues such as size differences, lighting cues, and visual occlusion. It may show four different patterns with one part of one of the patterns slightly closer to the subject than the rest of the patterns. The Frisby Stereopsis VR test may provide advantages over the real-world Frisby Stereopsis test by reducing or eliminating other monocular clues such as shadow/glare and/or perspective distortion.

In the test-specific UI area 550, there may be one or more (e.g., from left to right) of:
(A) Corner buttons that can be used to select which corner the stereopsis stimulus is displayed, such as a bottom-right corner button 1912, a top-right corner button 1914, a top-left corner button 1916, and a bottom-left corner button 1918. These corner buttons may be used as arrow toggles to indicate which of the four tests have the stereopsis stimulus (stimulus part that is closer to the subject).
(B) Distance toggle buttons to set the stereopsis VR stimulus at different distances from the non-stereopsis stimulus, such as a 6 mm distance toggle button 1920, a 3 mm distance toggle button 1922, and a 1.5 mm distance toggle button 1924. The closer stimulus part may be compared to the rest of the test stimulus.
(C) Distance toggle buttons for overall stimulus distance from the subject, such as a 30 mm distance toggle button 1926, a 40 mm distance toggle button 1928, a 50 mm distance toggle 1930 button, a 60 mm distance toggle button 1932, a 70 mm distance toggle button 1934, and a 80 mm distance toggle button 1936.
(D) A turn stimulus on or off toggle button 1938 (which may be unique, such as a checkmark indicating "ON" in an otherwise dark grey box).
(E) An icon representing the VR stimulus 1940.

Figure 19C:
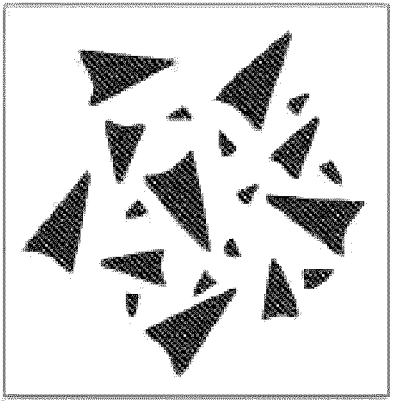
FIG. 19C shows an example of a close-up of a view of the Frisby Stereopsis VR test.
Figure 19B:
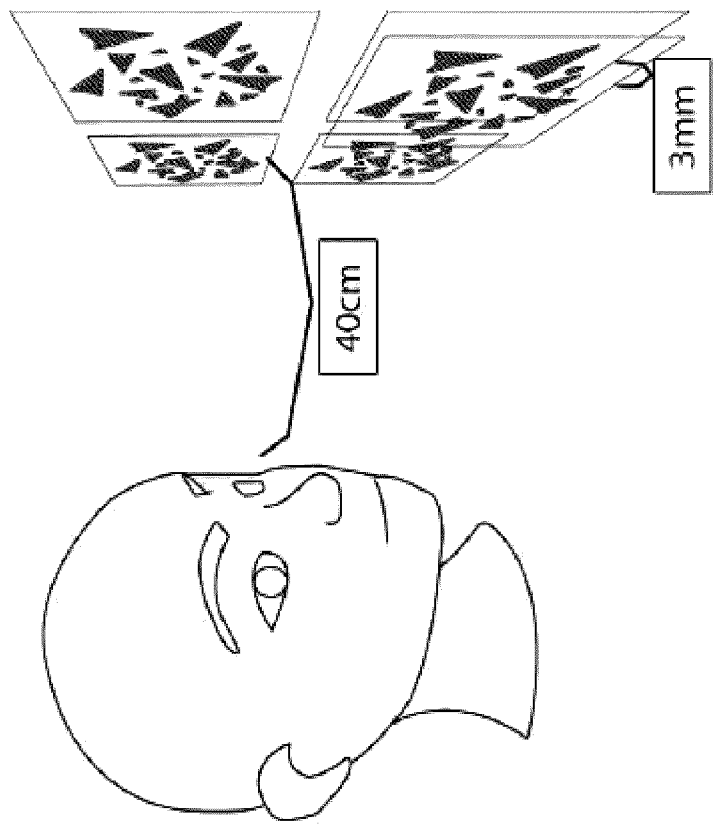
FIG. 19B shows a schematic diagram of an example view of the Frisby Stereopsis VR test corresponding to the UI of FIG. 19A.

The Stereopsis VR test may be set up by the user using the above elements of the test-specific UI area 550 (e.g., as shown in FIGS. 19B and 19C). To set up the test, the user may use the VR test creation interface 400 to begin displaying the standard Frisby Stereopsis stimulus at the gold standard size and thickness specifications.

The user can then use the corner buttons 1912-1918 to put a depth varied VR stimulus in any of the four corners. The depth toggle buttons can be used by the user to put the depth varied stimulus at different depths, such as 6 mm, 3 mm, and 1.5 mm. The distance toggle buttons can be used by the user to put the overall stimulus exactly at prescribed distances, such as 30, 40, 50, 60, 70, and 80 mm from the subject. The turn stimulus on or off toggle button 1938 can be set by the user so that settings can be adjusted while the VR stimulus is off, and then it can be turned on to avoid monocular or movement clues.

In VR, the subject may see the Frisby Stereopsis test layout, as shown in FIG. 19B. When the VR stimulus is presented so that it is viewed monocularly by the subject, it is likely very impossible for the subject to tell which part of which square is closer than the rest. When the VR stimulus is presented so that it is viewed close up by the subject, as shown in FIG. 19C, monocular cues may indicate that the center of one of the squares is standing out, including color difference, occlusion, and an oblique angle for view. These are, for example, the kinds of things that the test endeavors to overcome.

Referring now to FIG. 20A, shown therein is an example embodiment of the test-specific UI area 550 of VR test creation interface 400 for the Synoptophore VR test. The Synoptophore VR test is a VR approximation of the real-life Synoptophore test. The Synoptophore test may be used to detect abnormal retinal correspondence (ARC), or measure heterophorias and heterotropias. For example, the synoptophore may be a large, complex device that displays a slide in each eye of the subject. The slides can be translated horizontally, vertically, and depthwise, as well as rotated horizontally, vertically, or torsionally. Accordingly, the subject can move the slides until they match a certain criteria, such as a lion in the left eye appearing in a cage displayed in the right eye. Some of the slides, when shown together, may appear to show depth or stereopsis, like part of the slide image is closer to or farther away than the other. Accordingly, the slides can be moved by the subject until the subject manages to achieve stereopsis, and then the settings can determine what kind of corrective prism or surgical re-orientation of the eye the subject may require.

In the test-specific UI area 550, there may be one or more (e.g., from left to right) of: a horizontally reverse left eye stimulus toggle button 2012; a horizontally reverse right eye stimulus toggle button 2014; a swap left and right eye stimulus toggle button 2016; a black or white stimulus background toggle button 2018; an actual stimulus toggle button 2020; a stimulus distance slider 2022; and a stimulus distance amount text indicator 2024.

The Synoptophore VR test may be set up by the user using the above elements of the test-specific UI area 550, for example, as shown in FIGS. 20B and 20C. FIGS. 20B and 20C may also be used as models for VR representations of a Synoptophore device. To set up the test, the user may use the VR test creation interface 400 to begin displaying a standard Synoptophore VR stimulus.

The horizontally reverse left eye stimulus toggle button 2012 and the horizontally reverse right eye stimulus toggle button 2014 can be used by the user to flip either slide stimulus horizontally. The swap left and right eye stimulus toggle button 2016 can be used by the user to flip in which of the subject eyes each stimulus slide is seen. The black or white stimulus background toggle button 2018 can be used to toggle between a black background and a white background. The actual stimulus toggles 2020 can be used to select or cycle through each slide art type, such as a lion, a rabbit, a swing, balls, lanterns, and a circle bisect stimulus. The stimulus distance slider 2022 can be used to move a stimulus toward or away from the subject's eyes in VR with meters displayed as in all distance sliders.

In at least one embodiment, use of rotation sliders (prismatic and torsional are used along with the VR controllers so the user can select and move certain sliders as on a physical synoptophore device.

Figure 21A:
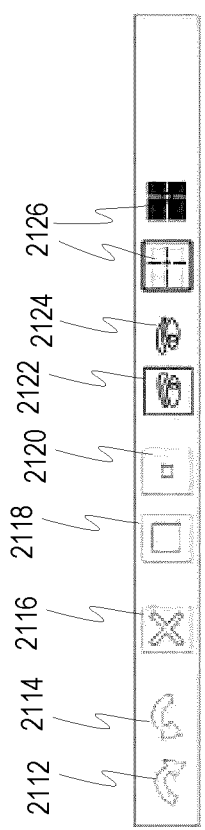
FIG. 21A shows an example embodiment of a test-specific UI area for a Lees Screen VR test.

Referring now to FIG. 21A, shown therein is an example embodiment of the test-specific UI area 550 of VR test creation interface 400 for the Lees Screen test. The Lees Screen VR test is a VR approximation of the real-life Lees Screen test. The Lees Screen test may be used to detect incomitant strabismus, or measure incomitant ocular deviations in various positions of gaze. For example, the test may display a screen with small circular targets to one of the subject's eyes, and allow the subject to point to where the targets would be if the screen was in the other eye as well. By displaying a VR screen to only one eye, the other eye perceives that the VR screen is being presented to both eyes, so the subject can place targets to match where they think the targets are, but misaligned eyes will cause targets placed by the subject to be placed in the wrong positions. This may help determine discrepancies between the visual field, especially when the subject's eye is at its extreme extents (e.g., looking hard to the top and bottom corners). The test may affect the effectiveness for torsional comparisons between each of the subject's eyes, for example, by capturing torsional rotation as well as position of the targets. The test-specific UI area 550 may be expanded, for example, to combine features of the Lees, Harms, and Hess tests.

In the test-specific UI area 550, there may be one or more (e.g., from left to right) of: an undo last marker drop button 2112; a redo last marker undone button 2114; a delete all markers button 2116; a show close up stimulus toggle button 2118; a show distant stimulus toggle button 2120; a show/hide left eye orientation Lees Screen test button 2122; a show/hide right eye orientation Lees Screen test button 2124; and a black or white screen background toggle button 2126.

Figure 21B:
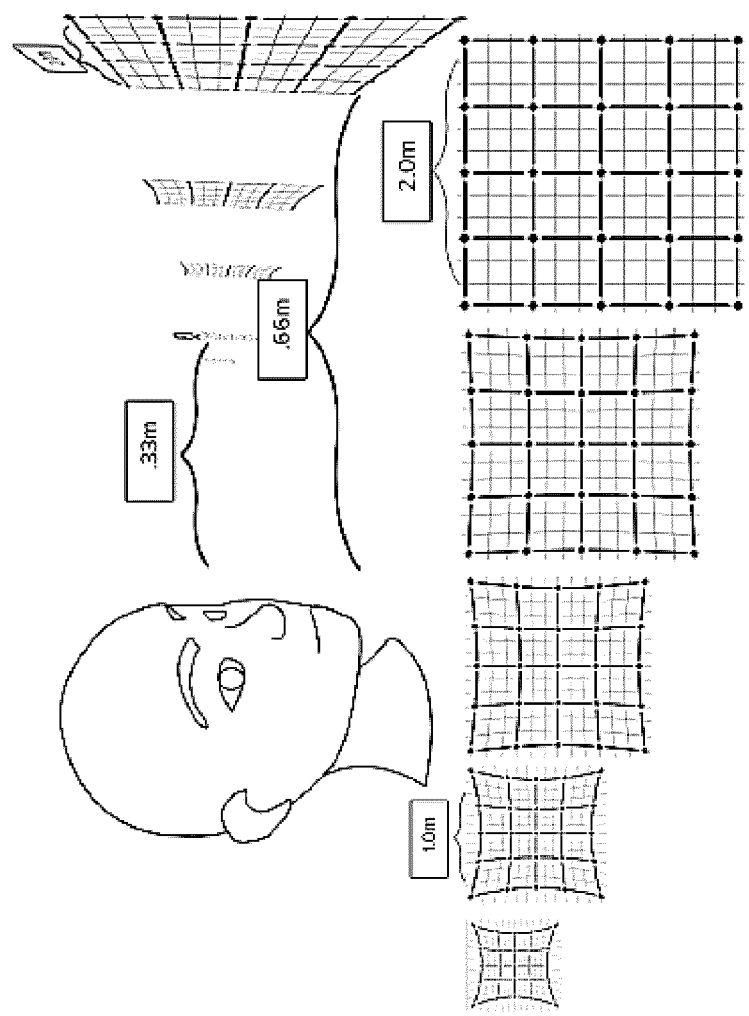

The Lees Screen VR test may be set up using the above elements of the test-specific UI area 550 (e.g., as shown in FIGS. 21B and 21C). To set up the test, the user may use the VR test creation interface 400 to begin displaying the Lees screen in VR in either the subject's left or right eye, where the subject's opposite eye has a VR controller indicator that allows the subject to try to line it up vertically, horizontally, and rotationally, with the grid displayed to the subject's other eye and place markers using the VR controller trigger.

The undo last marker drop button 2112 and the redo last marker undone button 2114 can be used by the user to undo or redo the last marker placement to the beginning of the test. The delete all markers button 2116 can be used by the user to delete all markers. The show close up stimulus toggle button 2118 and the show distant stimulus toggle button 2120 can be used to display the VR stimulus close up with a small scale (e.g., to match the gold standard), or to display the VR stimulus as being moved far away with a large scale as an option. The show/hide left eye orientation Lees Screen test button 2122 and show/hide right eye orientation Lees Screen test button 2124 can be used to swap the display screens on which the VR stimuli are shown (i.e., the subject's left or right eye is presented with the grid). The black or white screen background toggle button 2126 can be used to choose whether the grid is black with white lines, or white with black lines.

The show close up stimulus toggle button 2118 and the show distant stimulus toggle 2120 button may together be considered as a distance/scale option. The default screen stimuli may be, for example, approximately 0.75 meters away from the eye and about 1 meter square. The show distant stimulus toggle button 2120 may indicate the toggle that will place the VR object, for example, 3 meters away in VR from the subject's eyes and make the screen large enough to look the same size in the visual field as it does when it is close. An advantage of providing the Lees Screen test as described above in VR as compared to in real life is that making a huge Lees Screen type stimulus at great distance is practically prohibitive.

An example of what the subject sees and/or does in VR while being tested with the Lees Screen VR test is shown in FIGS. 21B and 21C, which may include one or more of:

(A) The subject positions red targets by moving the VR controller to the parts of the grid where small circles appear to the subject's eye that is opposite to the controller. When the subject presses the VR controller trigger, this places a target at the x, y position and torsional rotation the subject desires.

(B) When a given test is finished, the left VR stimulus that was presented to the subject's left eye can be presented to the subject's right eye in the subsequent test and the right VR stimulus that was presented to the subject's right eye can be presented to the subject's left eye in the subsequent test.

(C) The VR stimulus presented to the opposite eye has a different color target but works the same way. For example, the subject may place little colored dots with cross hairs on them at positions on the Lees Screen. The subject performs the exercise for their left and right eyes where the Lees Screen is first displayed to their right eye so that the subject places targets in their left field of view so as to compare alignment of the eyes. The VR stimulus may be switched for presentation from the left eye to the right eye and vice versa, and then the targets may be a different color as they are placed at a new location by the subject. At the end of the VR visual test, both screens are shown as well as the locations of all the targets that were placed by the subject during the test so that the clinician can assess the result—optionally creating a screen print for later analysis.

(D) When the tests on both eyes have been completed, the test results reveal where each side of the targets were placed for each eye, and the results may be analyzed.

(E) At any time during or after the tests, the colors in the VR stimulus can be swapped from black background/white grid to white background/black grid using the black or white screen background toggle button 2126.

The test may involve presenting a VR stimulus having a thick line stroke that is visually attached to a controller and shown to the subject's opposite eye compared to the subject's eye which is presented with a VR stimulus having an actual grid, as shown in FIG. 21C. For example, as the subject is looking at the VR stimulus that is presented to the subject's left eye, the subject may press the trigger of the VR controller to leave a marker, such as a red marker, that is centered at an x, y position selected by the user and has a rotation, as shown in FIG. 21C, and for the VR stimulus that is shown to the subject's right eye, a centered marker potentially having a different color but otherwise having the same x, y position and rotation may be created.

For example, the subject may have a light-beam like line projecting from the VR controller that they are holding. At the end of the light beam is a small circle with cross hairs. If the subject twists the circle torsionally, and then presses the VR controller trigger, the test will show not only the location of the circle that the subject just placed, but also how the subject torsionally twisted it when the subject placed the circle at a given position. The subject's aim is to match the x, y position as well as the angle of the lines in the grid torsionally.

Once both tests are complete, the user may, for example, display the position and angles of all of the targets that were placed by the subject during the test and then immediately take a screenshot so that a record of the performance for the subject is retained.

In at least one embodiment, the Lees Screen VR test may include allowing the user to vary the distortion (e.g., cause less distortion) as the VR stimulus is moved farther away from the subject's eyes in VR and simultaneously becomes larger to ensure that it takes up the same VR visual field amount. This can be attributed to how in the Lees test, as compared to the Harms test, some optical distortion calculations may be used to "pinch" distort the VR stimulus. This VR test may be configured so that the VR stimulus is normally presented in this way so the user does not need to make any special selections. Advantageously, this aspect of the test can be done more accurately and easily in VR than in physical reality, since an object at a variable distance can easily be shown in VR and be distorted and scaled in real time as the object moves farther or nearer to the subject's eyes in VR.

Figure 22:
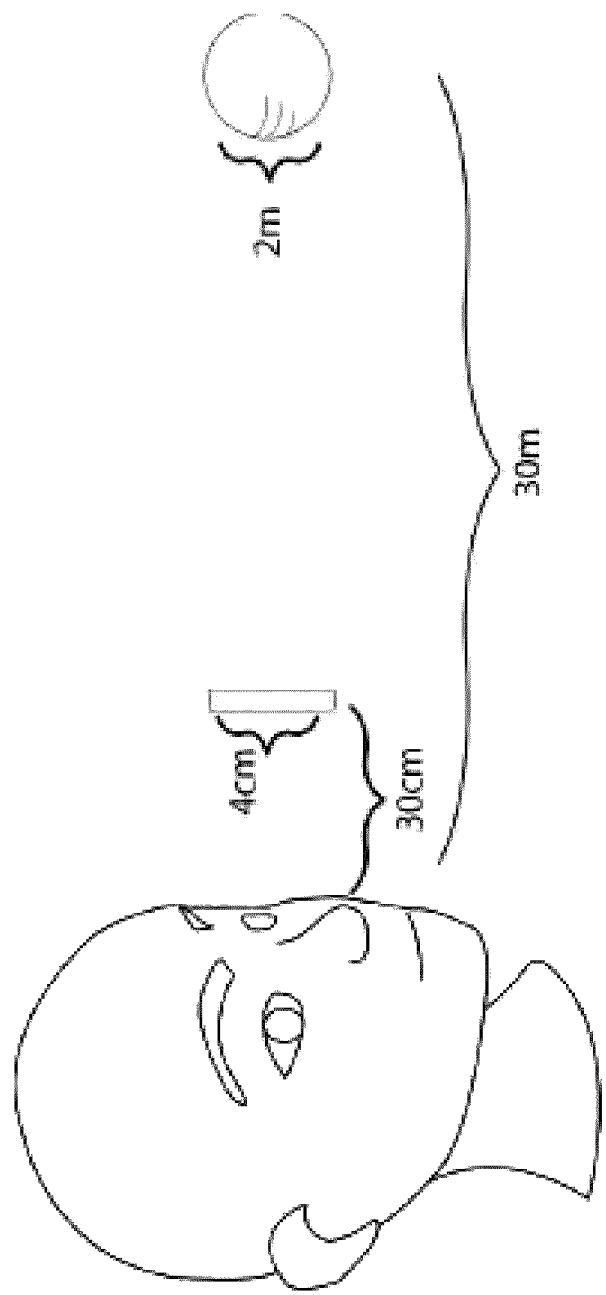
FIG. 22 shows a schematic diagram of an example representation of a Brock String VR test.

Referring now to FIG. 22, shown therein is a schematic diagram of an example of a Brock String VR test. In at least one embodiment, the test-specific UI area 550 of VR test creation interface 400 can be set up to perform a Brock String VR test. The Brock String VR test is a VR approximation of the real-life Brock String test. The Brock String VR test may be used to test convergence insufficiency and other anomalies of binocular vision. For example, the test may show a VR stimulus with a small gold bar that is at close proximity to the subject's eyes in VR, and a large red sphere that is several meters away from the subject's eyes in VR. If the IPD settings are correct and stereopsis is possible for the subject, then converging on the small gold bar makes it appear as if there are two red spheres. Conversely, if the subject's eyes converge on the red sphere, two gold bars may then be shown on either side of the sphere.

This is analogous to what happens in the real world due to the convergence being done with the subject's eye muscles. In the real world, a subject may do this test with their thumb and another object (e.g., a light or small item) a few meters away. The subject may hold their thumb a few inches from their face and focus on it. The subject may then notice that the far away object appears as two images while their thumb is one object. If the subject does the opposite and focuses on the distant image, then two thumbs appear in their view. The Brock String VR test may have advantages over the real-life test such as more accurate and consistent results.

Figure 23:
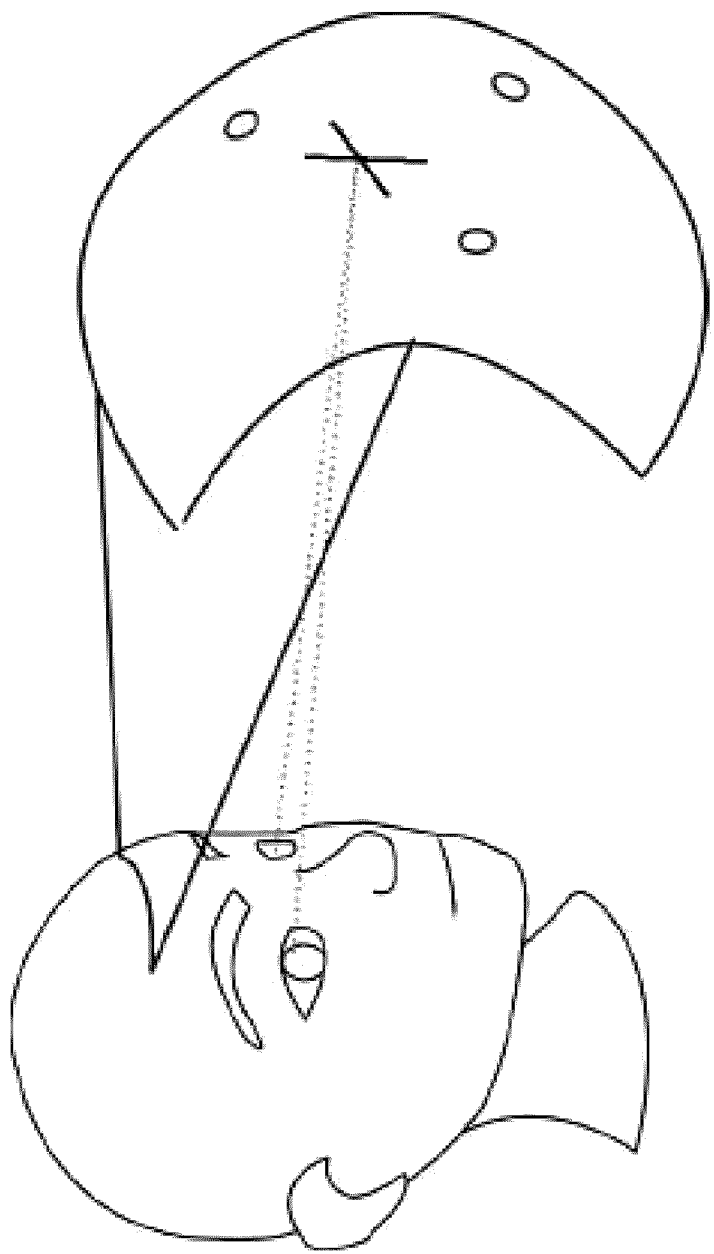
FIG. 23 shows a schematic diagram of an example representation of a Visual Field VR test.

Referring now to FIG. 23, shown therein is a schematic diagram of an example of a Visual Field VR test. In at least one embodiment, the test-specific UI area 550 of the VR test creation interface 400 can be set up to allow the user to perform a Visual Field VR test on the subject. The Visual Field VR test is a VR approximation of the real-life Visual Field test. The Visual Field VR test may be used to test dysfunction in the subject's central and peripheral vision. For example, the VR stimulus for this VR test may be generated to show objects at various places within the subject's visual field while the subject keeps their gaze fixed. The objects may be visible to only one of the subject's eyes at a time. The VR stimulus may be modified such that the objects may move out of the subject's visual field and then back in. The subject may signal when they see the object come back into view in VR. Alternatively, or in addition, one of the eye tracking sensors 124 or 126 may be used to detect when the subject's eye sees the object come back into view. For example, the subject may look at the stimulus if it suddenly appears in an otherwise empty space, and the user can tell what the subject is looking at when tracking the subject's pupil.

In at least one embodiment, the Visual Field VR test may involve "virtually attaching" a stimulus to the head of the subject in VR, so that the entire stimulus fires various flashes inside of a "sphere shape" in a similar fashion as the Humphrey visual field test. However, the VR stimulus is modified so that the position of the sphere shape moves with the subject's head and the subject's eye position is tracked to ensure centering relative to the head/eye gaze position of all the flashes. This ensures the widest possible visual field test as the subject can move their eyes as well as their head to ensure wider gaze assessment, even with limited VR hardware visual field extents. Accordingly, at least one of the subject's eye positions may be independently tracked by the head unit 112, and values corresponding to the eye positions may be tracked and recorded by the computer 140.

Figure 24:
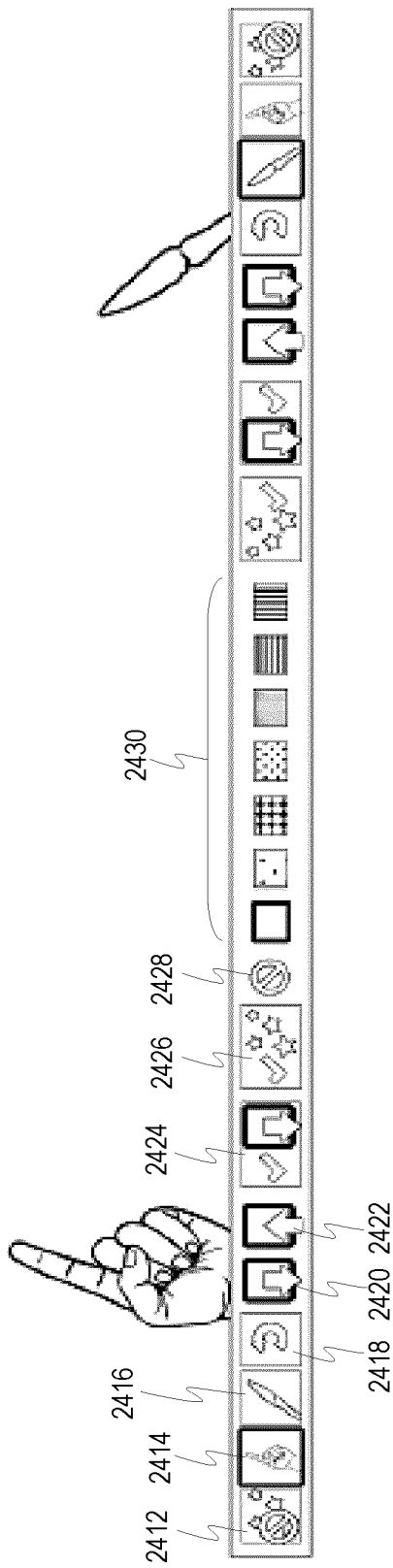
FIG. 24 shows an example embodiment of a test-specific UI area for an art program with a magnified view of a portion thereof.

Referring now to FIG. 24, shown therein is an example embodiment of the test-specific UI area 550 of VR test creation interface 400 for an art program, which may be used, for example, as a test or a practice environment.

In the test-specific UI area 550, there may be one or more (e.g., from left to right) of: a delete all particles button 2412; a choose regular controller mode button 2414; a choose paintbrush mode button 2416; a delete all painted items button 2418; a drop all painted items button 2420; a reposition all painted items button 2422; an allow controller to drop items toggle button 2424; an allow painting of particles toggle button 2426; a hide the environment toggle button 2428 (which may disable drop); and a choose color of environment toggle button 2430. These buttons and toggles may apply in order for the left side, and in reverse for the right side.

The user may set up the art program environment by using the above elements of the test-specific UI area 550. To set up the test, the user uses the VR test creation interface 400 to begin providing an environment for a subject to "paint" in 3D using a VR controller trigger. The subject can toggle between "brush" mode and "controller" mode.

In brush mode, the subject can create virtual objects in midair as they hold the trigger. When it is sensed that the subject applies more pressure on the trigger, the shape can be made larger in the VR environment. The shapes can be placed in the VR environment so that their position matches the rotation and position of the controller determined by the subject at the time of being instantiated. Shapes and colors can be determined based on inputs that are provided by the subject via the thumb controller when in brush mode. Additional options to allow the subject to select particle effects can be implemented in a similar manner. While in paint mode, when the subject's thumb touches the pad or stick on the VR controller, all of the paint options can be displayed in the VR environment. Movement of the subject's thumb on the thumbpad can be tracked by a tiny ball that is displayed in the VR environment. On overlap/collision between the tiny ball and any of the objects shown in the VR environment, the object can be displayed slightly larger in the VR environment which indicates selection. The object can then be displayed in normal size when the overlap/collision is no longer occurring. When the tiny ball overlaps/collides with a color sphere, the material is chosen, the material being, for example, a color, texture, image, or effect (e.g., flaming, smoking, refracting, casting shadows). At the same time, the shape selectors and particle selectors can become the same color as the selected material. When the tiny ball overlaps/collides with a shaped object in the VR environment, it becomes the selected shape. The spheres having the same color may adopt the newly selected shape too. When the tiny ball overlaps/collides with a particle selection object, it becomes "highlighted" with additional 3D modelling information, and the painted particles are set to that setting. When the subject presses the thumb button, all of the painted objects can be shown as being "physical" and they drop/bounce/collide with the ground in the VR environment. When the subject presses the thumb button again, all of these "physical" objects can be animated to move back to their original location. "Groups" of objects can be created when the subject lets go of the trigger.

In controller mode, when the subject presses the trigger while touching painted "Groups" the groups can be selected and then the VR environment is modified to show the selected groups moving with the controller. When the subject lets go of the trigger, the group remains at its location at the time when the trigger was released. The paint brush mode can be turned on and off when the subject presses the grip buttons on the VR controller. If either VR controller is on, an icon shaped like a brush or a VR controller can appear in the UI on the display of the head unit 112 and the current mode of either brush/controller (i.e., right and/or left) can be indicated. A maximum number of groups and objects may exist. Once either the maximum number of groups or objects is reached, the earliest object or group that was created can be destroyed, and so there is never more than the maximum number of groups or objects in the VR environment.

Figure 25:
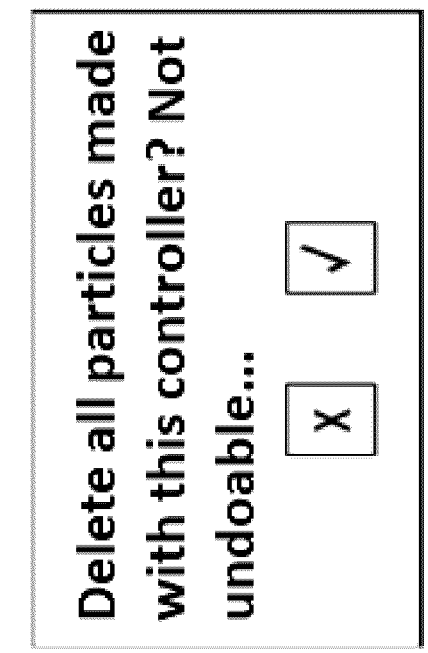
FIG. 25 shows an example of a confirmation popup window in the art program of FIG. 24.

The delete all particles button 2412 can be used by the subject to delete, in the VR environment, all of the particles attached to objects and groups that were created by the corresponding left or right brush. There may be a note on confirmation with a popup that appears as shown in FIG. 25. The choose regular controller mode button 2414 can be selected by the subject to choose controller mode. The choose paintbrush mode button 2416 can be selected by the subject to choose paintbrush mode. The delete all painted items button 2418 can be selected by the subject to refresh and delete everything that was drawn in the VR environment by the corresponding left or right brush. The drop all painted items button 2420 can be selected by the subject to drop all the objects that were just painted to the virtual floor as they become subject to "virtual gravity". The reposition all painted items button 2422 can be selected by the subject to return all of the objects that were just painted to their previous state (e.g., the previous position and rotation of these objects prior to the time when the button 2422 was selected). The allow controller to drop items toggle button 2424 can be selected by the subject to toggle between allow or do not allow the drop/return functionality on the VR controller. The allow painting of particles toggle button 2426 can be selected by the user to toggle between allow or do not allow draw particles on the VR controller. The hide the environment toggle button 2428 (which may disable drop) can be selected by the user to turn off the inner sandbox environment, so that, when off, objects cannot be "dropped" or they will virtually fall forever. The choose color of environment toggle button 2430 can be selected by the user to toggle the color of the inner sandbox environment.

Figure 26:
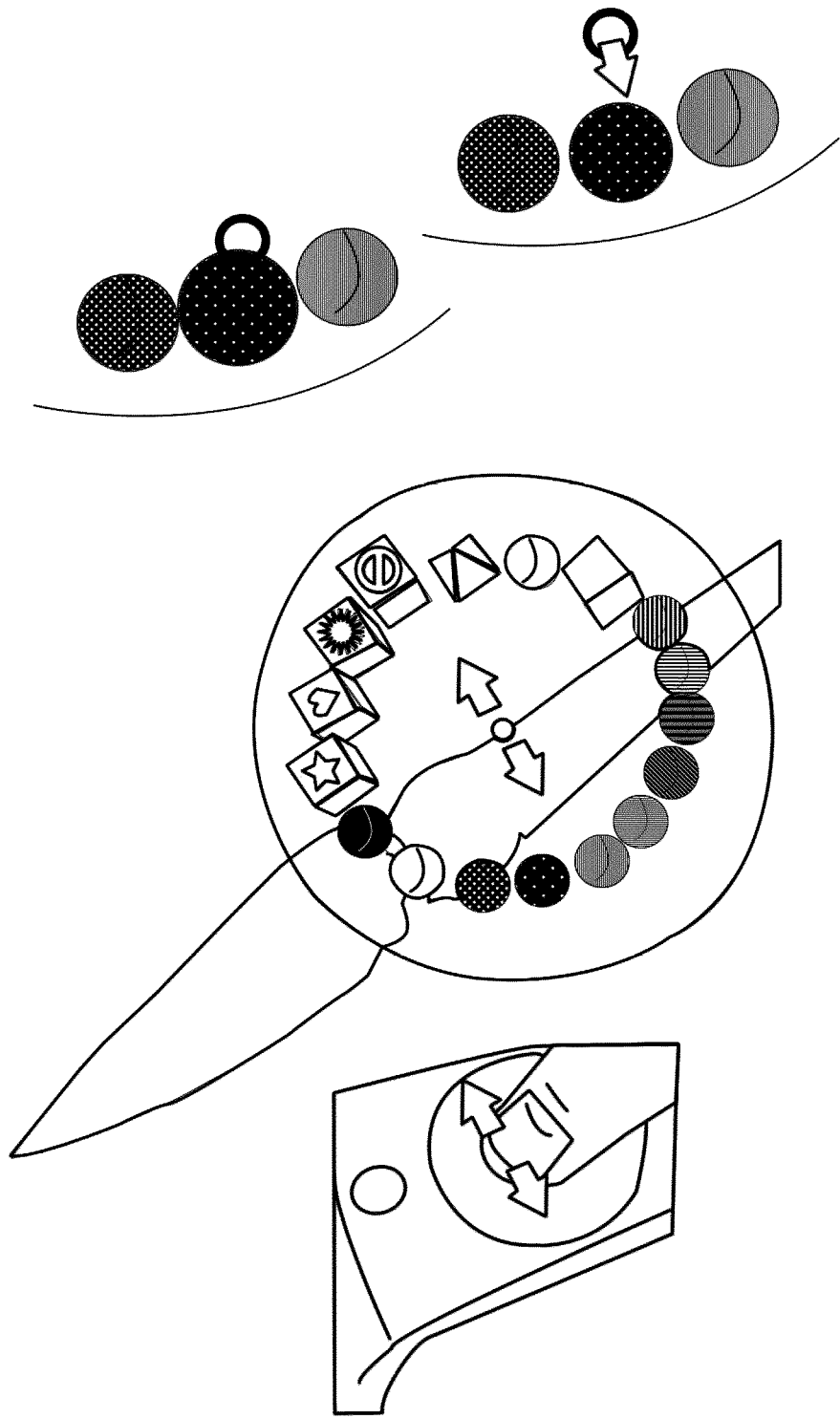
FIG. 26 shows an example embodiment of a VR view of a paint mode controller with a brush menu.

A paint mode controller shown in the VR environment may have a brush menu appear, as shown in FIG. 26, when the subject's (real-life) thumb is on it (e.g., as represented in the VR image by the paintbrush with the disc and all the menu items on it). A small grey ball may be displayed and moved in the VR environment to track the position of the subject's thumb on a virtual semi-transparent disc, as shown in FIG. 26. Brushes may surround the outside of the disc within reach of the subject's thumb, so that the subject can choose material color, shape, and particle type, as shown in FIG. 26. When selected, the selection may be highlighted, as shown in FIG. 26.

Figure 27:
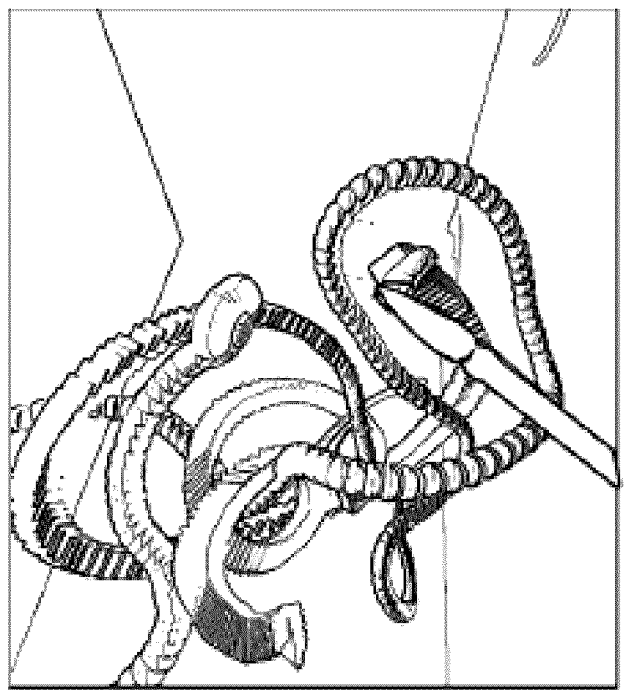
FIG. 27 shows an example of a VR view of art generated by the art program.

In the VR environment, the subject may see what they draw or paint in real time, in perspective, and/or in color, as shown in FIG. 27 (without color though). This may help introduce a subject to VR. The act of creating objects in the VR environment may give the subject a sense of environmental control, which may put them at ease. This may possibly activate the subject's parasympathetic nervous system, making the subject more receptive to any tests that may follow.

Figure 28:
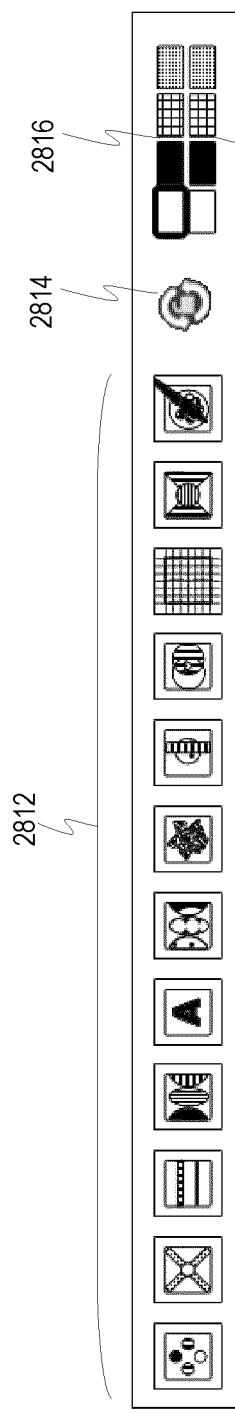
FIG. 28 shows an example embodiment of a test selection area.

Referring now to FIG. 28, shown therein is an example embodiment of the test selection area 560 of VR test creation interface 400. In the test selection area 560, there may be one or more (e.g., from left to right) of: individual test selection toggle buttons 2812 with icons; a lock stimulus tracking toggle button 2814; a top row of toggle buttons 2816 for skybox colors; and a bottom row of toggle buttons 2818 for showing/hiding walls/floor etc. in the specified color.

Figure 29:
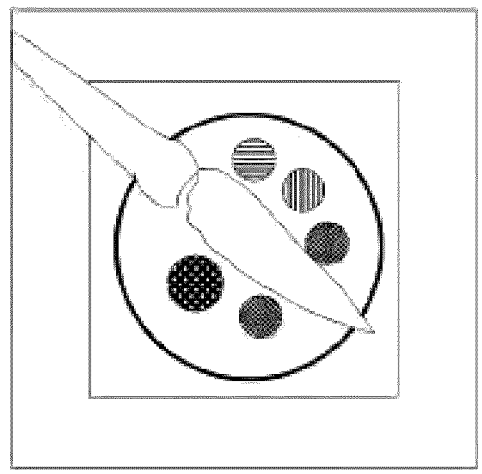
FIG. 29 shows an example of a large version of an icon in the test selection area of FIG. 28.

When an individual test selection toggle 2812 is selected by the user, a large version of its icon (e.g., as shown in FIG. 29) may be displayed in the top-left corner or other suitable position. The individual test selection toggle button 2812 can be used to select any of the tests with corresponding icons that, when selected, shows the given test and its current settings. Additionally, an icon may be displayed (e.g., in the top left of the UI screen) in much larger size to help indicate which test is being displayed at the time. The lock stimulus tracking toggle button 2814 can be selected by the user to lock or unlock the current main visual stimulus to the rotation of the subject's head, which may be indicated by using a small line (which might be colored) on two of the camera heads (e.g., in the top right) to show the position of the stimulus relative to the head of the subject's rotation. The top row of toggle buttons 2816 can be used to change the color of the skybox. The bottom row of toggle buttons 2818 can be used to change the color of (or hide/show) the walls and floor.

Figure 30:
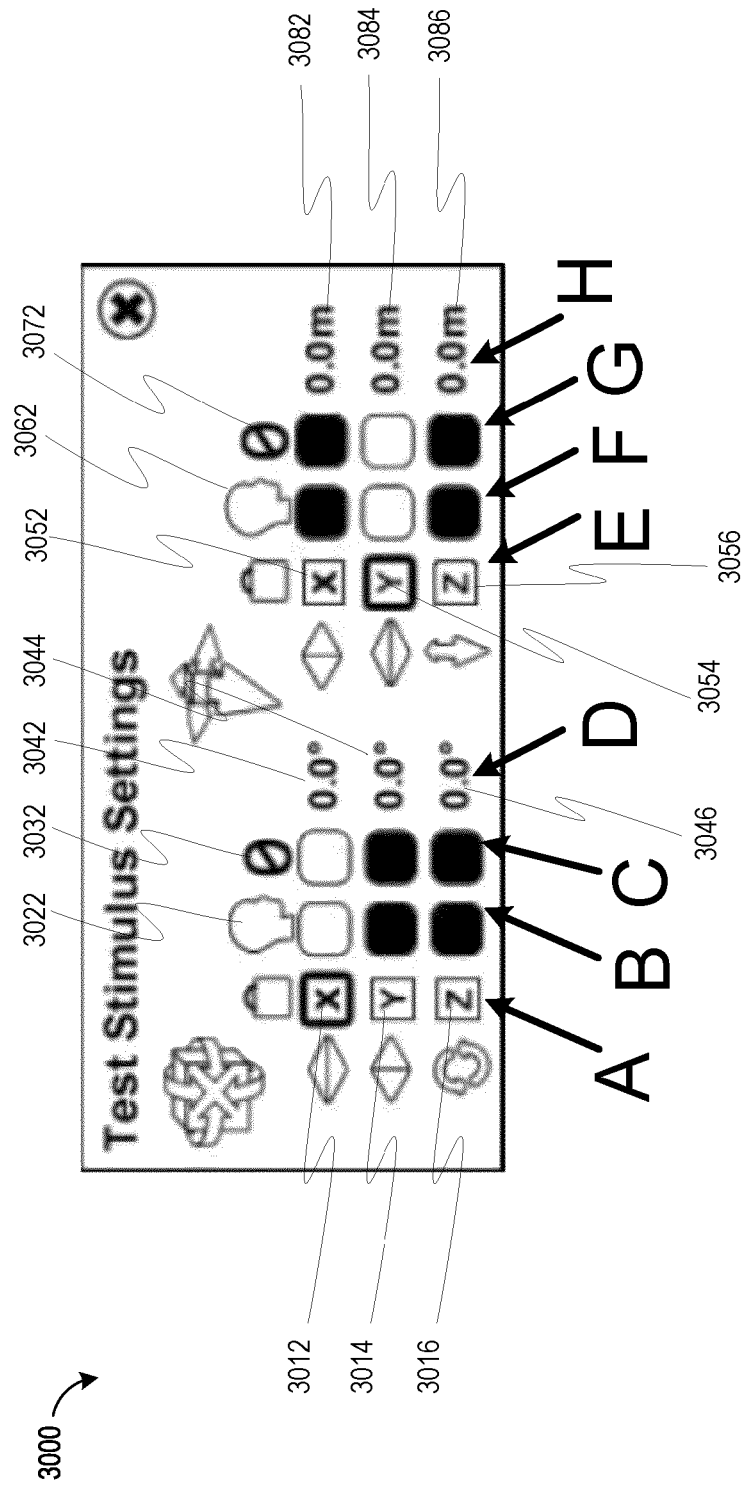
FIG. 30 shows an example embodiment of a test stimulus settings window.

Referring now to FIG. 30, shown therein is an example of a test stimulus settings window 3000 of VR test creation interface 400. When opened, the test stimulus settings window 3000 may be displayed, for example, in the center of the screen or viewing area.

In the test stimulus settings window 3000, there may be one or more (e.g., from left to right) of:
(A) Lock test stimulus rotation toggle buttons in one of the three axes, which locks the stimulus rotation to the subject head rotation in the corresponding axis, such as an X-rotation lock toggle button 3012, a Y-rotation lock toggle button 3014, and a Z-rotation lock toggle button 3016. For example, VR test creation interface 400 allows the user to select one or more these toggle buttons to lock or unlock rotation synchronization between the subject's head and the VR stimulus.
(B) A set the test stimulus rotation axis to the current subject head rotation toggle buttons for x, y and z axis 3022, which is only available when the lock stimulus buttons (A) are off. For example, if rotation synchronization is off, then VR test creation interface 400 allows the user to select this button for the VR stimulus to match the rotation of the subject's head in the corresponding selected axis (x, y, or z).
(C) A reset test stimulus rotation axis to default toggle button 3032 (e.g., zero from program starting rotation).

For example, if rotation synchronization is off, then VR test creation interface 400 allows the user to select this button to return the test stimulus rotation back to its default value for the selected axis x, y, or z (e.g., zero degrees).

(D) A current rotation in degrees of the test stimulus text, such as X-rotation 3042, Y-rotation 3044, and Z-rotation 3046. For example, this text may indicate the current rotation of the test stimulus relative to the test subject's head, which may be updated whenever the value changes.

(E) Lock test stimulus movement toggle buttons in one of the three axes, which locks the stimulus movement to the subject head position along the corresponding axis, such as an X-movement lock toggle button 3052, a Y-movement lock toggle button 3054, and a Z-movement lock toggle button 3056. For example, these displacement toggle buttons may work the same as with rotation, but with displacement (position) instead of rotation.

(F) A set the stimulus movement axis to the current subject head position buttons for x, y, and z axis 3062, which are only available when the lock stimulus button (E) is off. For example, these buttons may be available when the displacement toggles are off.

(G) A reset stimulus movement axis to default toggle button 3072 (e.g., zero distance in VR from program starting position).

(H) Current distance in millimeters of the test stimulus text, such as X-distance text 3082, Y-distance text 3084, and Z-distance text 3086. For example, the text updates may be in meters (as compared to the corresponding text items in the rotation section).

This test stimulus settings window 3000 may have an open/hidden state that is stored in the subject preferences file, and may be reflected on opening of the program. For example, the subject preferences file may be a data file stored in the test subjects folder that is updated when corresponding subject-specific settings are changed.

This test stimulus settings window 3000 may provide the user with the ability to toggle on or off continuous synchronization of the position and rotation of the test VR stimulus relative to the subject's head position in VR (which corresponds to the subject's real-life head position) in any or all three axes. These toggle states may be stored in a "Presets" settings file as they are test-specific.

Correspondingly, buttons may be available to set the test stimulus position and rotation at the current time in any or all three axes. When these buttons are selected by the user, this number may be saved to the subject general settings file to be loaded if the toggles are set to off as directed by the currently loading preset. In addition, buttons may be available to reset the test stimulus position and rotation to zero at any or all three axes.

Figure 31A:
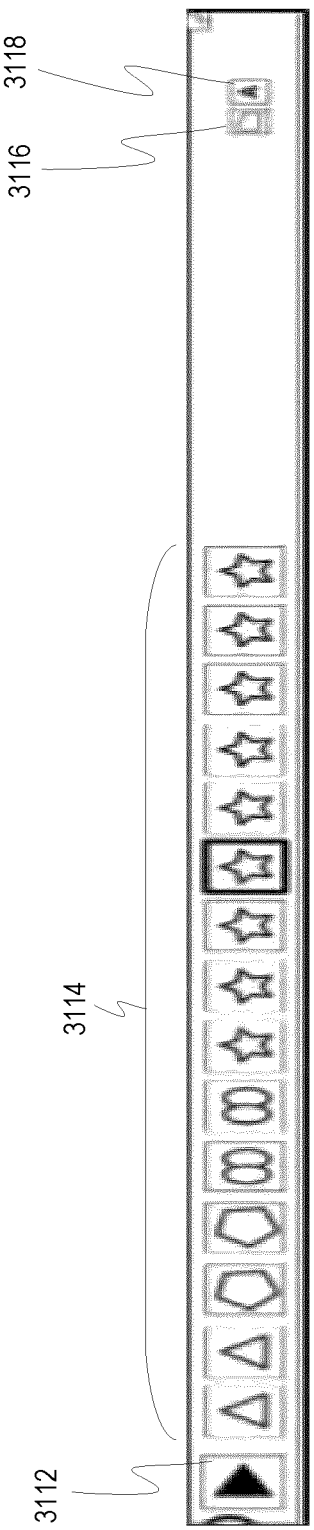
FIGS. 31A, 32A, and 33A show examples of protocol selection & authoring areas while in simple, advanced, and protocol authoring modes, respectively.
Figure 31B:
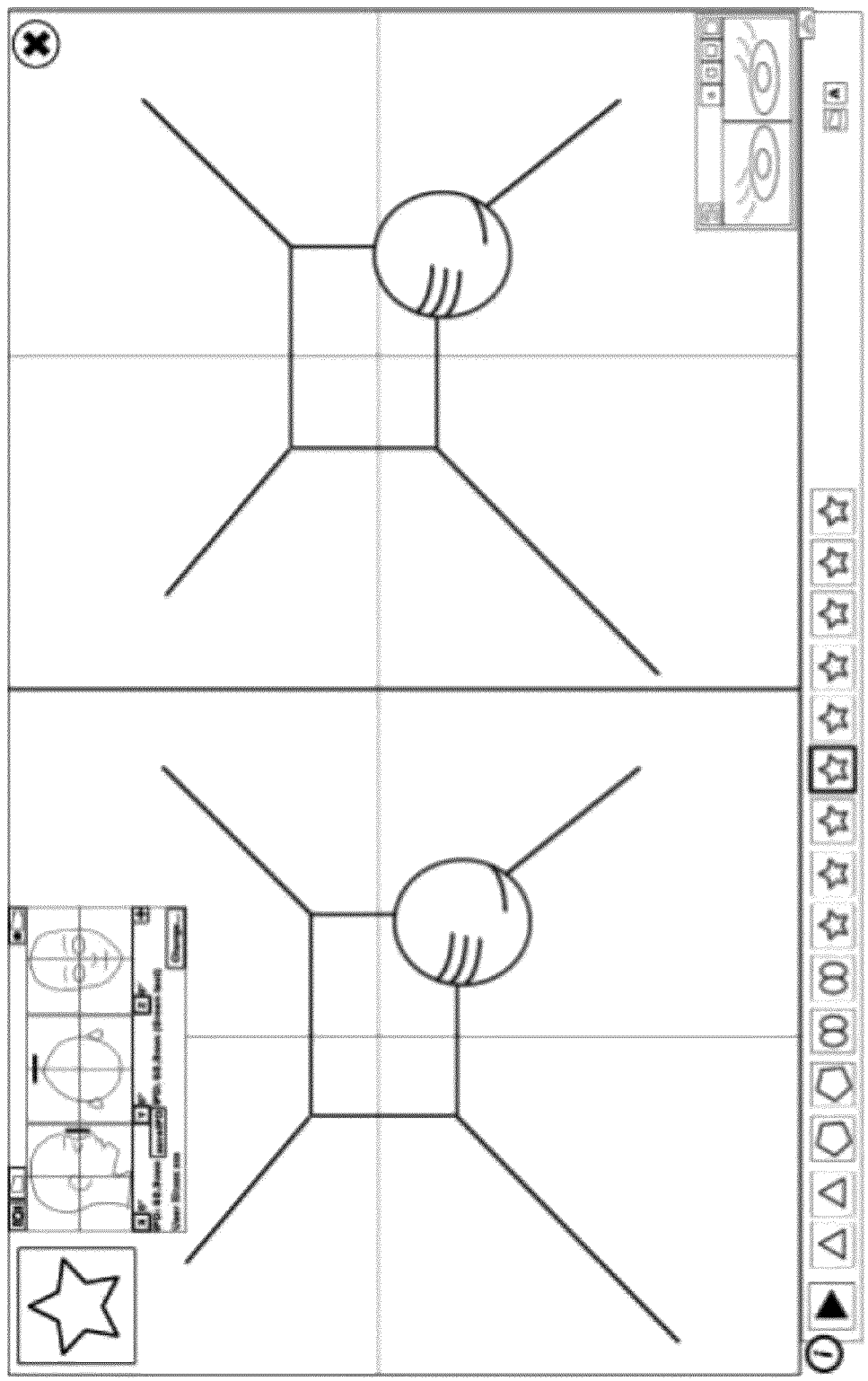
FIGS. 31B and 32B show computer screen images of examples of an overall screen in simple and advanced protocol modes, respectively.

Referring now to FIG. 31A, shown therein is an example of the protocol selection & authoring area 570 of VR test creation interface 400 while in simple protocol mode. The simple protocol mode may hide one or more of the customizable settings sliders for each test (e.g., if the user is not necessarily clinical or a researcher). The overall screen in simple protocol mode may look less complex (as shown in FIG. 31B). The protocol buttons may be alternatively referred to as preset buttons. For example, the simple protocol mode may be configured such that only the protocols are available and individual settings like stimulus distance, rotation, and other customizations are not available to change.

In the protocol selection & authoring area 570, there may be one or more (e.g., from left to right) of:

(A) A play next protocol button 3112: selecting this may advance to the next protocol and move the user and subject through each of the loaded protocol settings. When the last protocol is reached, it may cycle back to the first one.

(B) Protocol selection toggle buttons 3114: these may be highlighted as they are being displayed, and they may be clicked on for selection. For example, a gold frame may indicate the currently displayed protocol; if no gold frame exists, current settings do not match any of the protocols.

(C) A load protocol set button 3116: this may be used to open a file browser (e.g., in Windows) and, on selection, provide a load confirm window, that prompts the user to cancel or confirm. On selection of confirm, the selected protocol set may be loaded.

(D) A switch to advanced protocol selection mode button 3118: this may be selected to toggle between simple mode and advanced protocol selection mode.

Figure 32A:
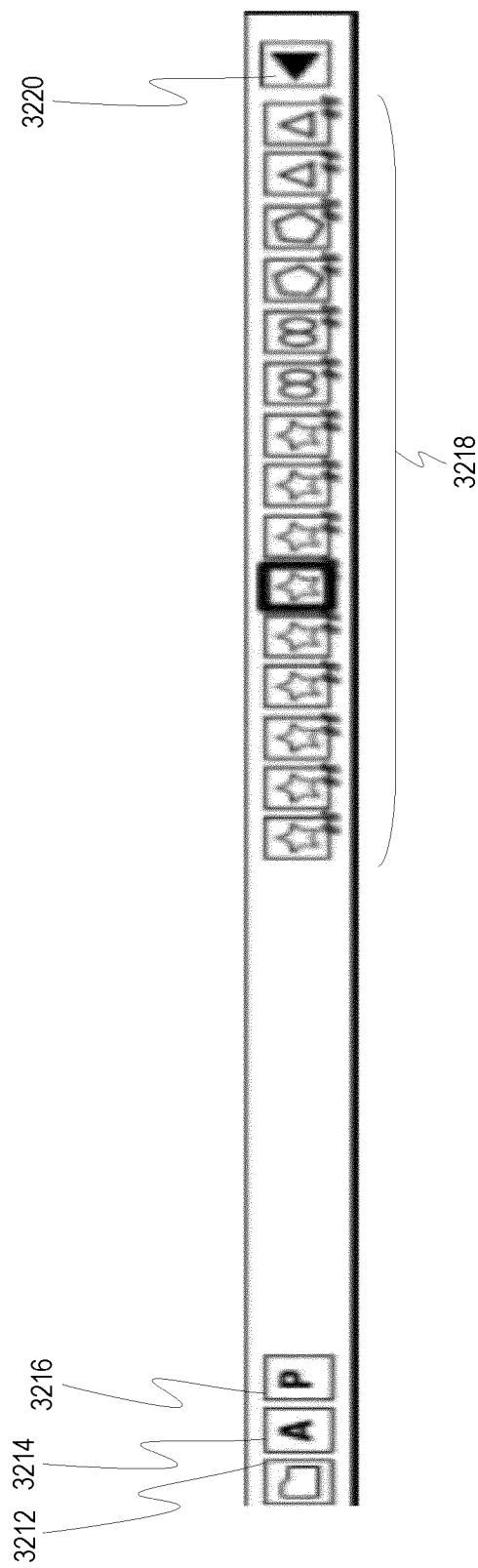
Figure 32B:
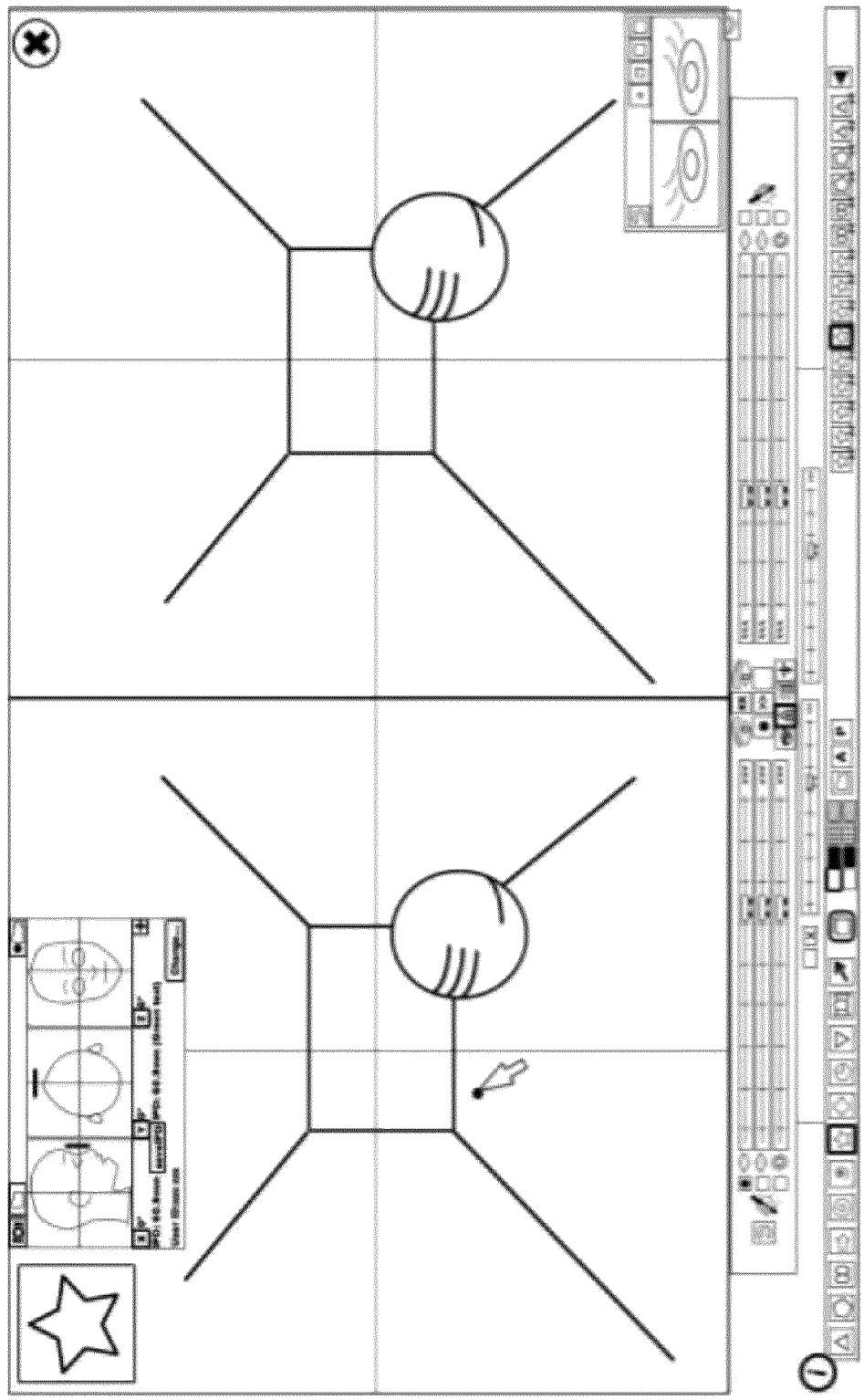

Referring now to FIG. 32A, shown therein is an example of the protocol selection & authoring area 570 of VR test creation interface 400 while in advanced protocol selection mode. The advanced protocol selection mode may show some or all of the customizable settings sliders for each test (e.g., if the user is clinical or a researcher). The overall screen in advanced protocol selection mode may display (potentially many) more features (as shown in FIG. 32B) than what is shown in the simple protocol mode.

In the protocol selection & authoring area 570, there may be one or more (e.g., from left to right) of:

(A) A load protocols from the external file button 3212: this may be used to open a file browser (e.g., in Windows) and, on selection, provide a load confirm window, that prompts the user to cancel or confirm. On confirmation, the selected protocol set may be loaded.

(B) A switch to authoring mode button 3214: this may be selected by the user to toggle between authoring mode and playback mode.

(C) A switch to protocol playback mode button 3216: this may be selected by the user to toggle between playback mode and authoring mode.

(D) Protocol selection toggle buttons 3218: these buttons may be used to select or cycle through a series of currently loaded protocols. For example, a gold frame may indicate the currently displayed protocol while if no gold frame exists, current settings do not match any of the protocols.

(E) A protocol "next" button 3220: may be used to cycle through all the protocols, and when it reaches the one to the far right, it may start over at the first one.

The VR test creation interface 400 may store all test-specific UI settings, which may be accessed either by the user directly selecting them, at which time the stored settings are applied, or by the user selecting the arrow button in the bottom right corner to cycle from one to the next and back to the start again. In this way, a series of preset tests can be quickly accessed by the user and the subject can quickly move from test to test without having to re-setup all of the settings. The presets can be stored in an external presets file.

In place of, or in addition to, the load protocols from the external file button 3212, there may be a reload protocols from the external file button, which can be selected by the user to refresh/restore the current presets from an external file (in case unsaved presets have become corrupted or edited accidentally).

The protocol selection toggle buttons 3216 may be configured to capture the icon from the selected test and use it for when they are displayed. They may be highlighted when selected or when the current settings match the settings they have stored in them.

For example, each protocol may have a specific icon or "logo". The protocol icon matches the logo of the currently selected test during authoring mode so that it can be saved with it. If a protocol is selected and it matches one of the tests including every possible setting, that test icon to the left may be highlighted as well. If a protocol is selected and then the test settings are altered in any way, the protocol becomes unhighlighted, indicating that it no longer is matched by what is being displayed and thus all the settings precisely.

The advanced protocol selection mode may operate as the simple protocol mode. For users who may want to deviate from the supplied protocols (i.e., supplied VR vision tests), then once a particular protocol is selected, individual settings for the protocol may be altered by the user, by utilizing various input GUI elements described herein to implement a desired setting. Once the settings of a given protocol do not match predefined settings for the protocol or settings from the protocol data file, the protocol icon highlighting may be disabled.

The advanced protocol selection mode may be used by the user to create and/or edit protocols and protocol sets. A protocol set refers to a group of protocols. A given protocol is a collection of the current test settings for a given VR test so that the given protocol indicates the particular VR test, the positions (i.e., values) of the test sliders, the position (i.e., values) of the toggle buttons if applicable, and so on for other relevant test settings for the particular VR test, for example. Users may load a set of protocols which are for different VR tests, or the set of protocols may all be the same VR test with different settings being used for each protocol (the later allows the user to quickly perform the same VR test with different settings rather than have to manually update the settings for a particular VR test before they present it to the subject). Changes to the current test settings may be applied to a given selected protocol, and then once all of the changes to each protocol in a protocol set are acceptable, the user may save the protocol set either to overwrite the data files that correspond to the currently loaded protocol set, or to create a new custom protocol set. The user may then return to regular protocol mode, and use the file folder button to select another protocol set or reload the current one.

Referring now to FIG. 33A, shown therein is an example of the protocol selection & authoring area 570 of VR test creation interface 400 while in protocol authoring mode. The protocol authoring mode allows the user to edit already defined protocols.

In the protocol selection & authoring area 570, there may be one or more (e.g., from left to right) of:
  (A) A load protocol set from the external file button 3312: which may be used to open a file browser (e.g., in Windows) and, on selection, provide a load confirm window, that prompts the user to cancel or confirm. On confirmation, the selected protocol set may be loaded.
  (B) A switch to protocol playback mode 3314: may be selected to toggle between protocol authoring mode and playback mode.
  (C) A protocol save button 3316: may be selected to save current test settings to the currently selected protocol.
  (D) A protocol record button 3320: may be selected to record the current presets for a selected protocol (e.g., in internal memory), and when a preset is saved, the current test icon becomes its icon.
  (E) A protocol add button 3322: may be selected to add a default blank preset that can be overwritten with the protocol record button 3320.
  (F) A protocol selection toggle button 3324: may be selected to cycle through the protocols in the current protocol set.
  (G) A protocol delete button 3326: may be selected to delete the currently selected protocol.

In place of, or in addition to, the load protocols from the external file button 3312, there may be a reload protocols from the external file button, which can be used to refresh/restore the current protocols for a given protocol from an external file (in case unsaved protocols have become corrupted or edited accidentally).

The protocol save button 3314 may operate as a "save confirm" button, which may be used to launch a small confirm save window. The confirm save window allows the user to cancel or confirm saving all of the current protocols to the external file, overwriting what was previously there. The confirm save window may display directly over the authoring buttons, preventing them from being selected.

Figure 33B:
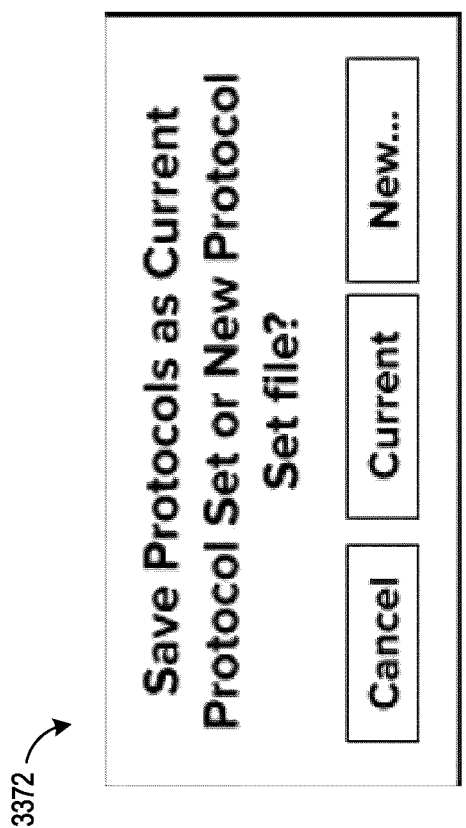
FIG. 33B shows an example of a prompt to save current/new in protocol authoring mode.

The protocol save button 3314 may operate as a "save current/new" button, which may be used to launch a save window, such as prompt 3372 (as shown in FIG. 33B). Prompt 3372 may display directly over one or more buttons, thus preventing them from being selected. Selecting "Cancel" hides the window with no change. Selecting "Current" overwrites the current protocol set file with the protocols as they are in the program, and hides the window, returning to previous. If "New . . . " is selected, this displays a prompt to enter a new protocol set filename and save it or cancel. On selecting cancel or save, the prompt/blackout disappears, returning the user to the former state. On selecting save, the new file with the indicated name is saved. The save button may be semi-transparent/disabled if the filename is invalid, and become enabled and fully opaque when the filename entered is valid.

For example, there may be an external file that contains data that represents a set of protocols. While using the VR test creation interface 400, that set may be loaded into program memory, but the file itself remains distinct. Protocols may be updated, changed, and/or edited, but they remain distinct until the protocol set is actually saved and the settings stored in temporary program memory, which is then written to the external file.

In place of, or in addition to, the switch to protocol playback mode button 3314, there may be a return to regular protocol mode button, which can be used to return when editing is completed.

In place of, or in addition to, one of the above buttons, there may be a return to regular protocol mode button (from protocol authoring mode), which may be used, for example, when editing is completed.

During use, the currently saved preset may be highlighted as in the standard way with toggles (e.g., to show that only one preset can be active at a time). For example, a gold frame may indicate the currently saved protocol.

The protocol selection toggle buttons 3324 may, for example, indicate their order (e.g., in the bottom right of each icon) and which test they represent with their icon. A plurality of protocols may, for example, be the same test only with different test settings.

Referring now to FIG. 34, shown therein is an example of a recording user interface 3400 of VR test creation interface 400. The recording user interface 3400 may be configured so that one or more of all VR trackable object movement, UI settings, and objects are recordable. In addition, the recording user interface 3400 may be operated to allow a user to select one or more recorded data files for playback (i.e., display) in VR.

Figure 35:
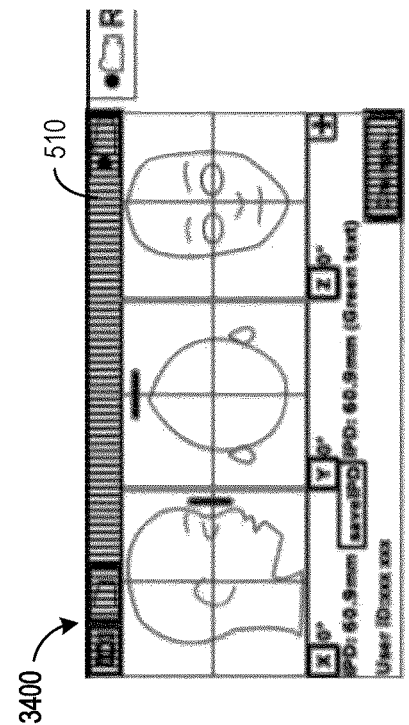
FIG. 35 shows an example of a subject data window while recording.

The recording user interface 3400 may modify the subject data area 510 before, during, and after recording. For example, some buttons may be set to a disabled state while recording, as shown in FIG. 35.

The recording user interface 3400 may provide additional status indicators, such as a recording indicator 3412 that provides a recording time stamp.

The recording user interface 3400 may be configured to capture all changed data from position/rotation of headset, hand controllers, which buttons the subject has interacted with, and their data state information (e.g., trigger pressure, x-y position of thumb on thumb pad or stick).

Recording may be selected by the user to capture slider position and toggle states at any given moment. The recording may be selected and configured by the user to capture the streaming video of eye cameras simultaneously. If available, recording may capture eye position/rotation and pupil size by using the eye tracking sensors 124 and 126.

A recording is started when the record scene button 616 is selected by the user. Once the record scene button 616 is selected, a confirmation window may appear to allow the user to confirm they want to commence recording. On confirmation, recording may begin, and a file may be created in the currently selected subject folder that can be accessed for later playback.

During recording, a recording interface may appear and one or more elements may be recorded. For example, all UI changes, such as slider positions, toggles, and the object positions and states affected by these value changes, may be recorded. As such, during recording, a rotation of the VR user's camera (e.g., a few degrees horizontally using the slider) may be recorded and may appear when played back. The current position and rotation of the subject's head and controllers may be recorded and may appear as such on playback. At least one of eye video and eye telemetry data may also be recorded.

During recording, file/open, change user, and capture screenshot functions may be disabled and the start record mode button may also be visibly disabled. These may become re-enabled when recording mode is fully exited.

Once recording has been stopped, a confirmation window may appear with three choices: save the recording, resume the current recording from the current position, and cancel and discard the recording. Selecting save the recording places the current recording as a .rec file into the current subjects folder and closes the dialogue. Selecting return resumes recording and closes the dialogue box. Selecting delete deletes the recording and exits the user from recording mode, also closing the dialogue box.

Figure 36:
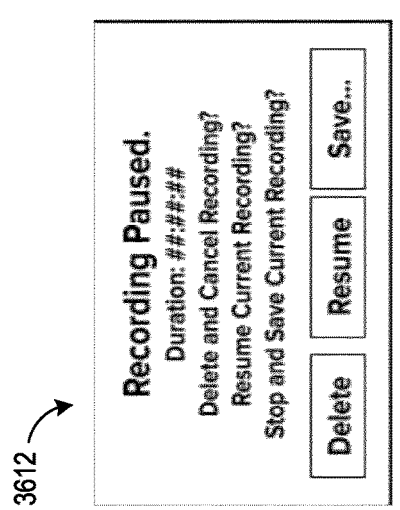
FIG. 36 shows an example of a recording paused dialog box.
Figure 37:
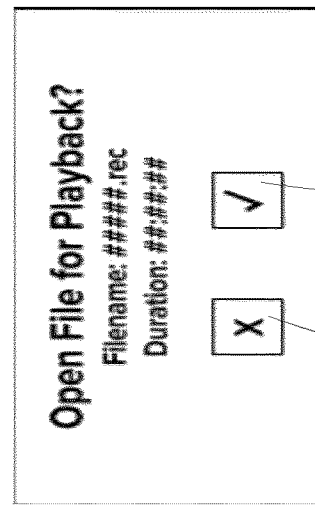
FIG. 37 shows an example of a playback file open confirm dialog box.

When the pause button is pressed, a recording paused dialogue box 3612 may appear, as shown in FIG. 36. After a recording has been saved, a playback file open confirm dialogue box 3712 may appear, as shown in FIG. 37. When a No (e.g., 'X') button 3714 is selected, the dialogue box 3712 closes and returns to the previous view. When a Yes (e.g., a checkmark) button 3716 is selected, the dialogue box 3712 closes and initiates a playback mode.

Figure 38:
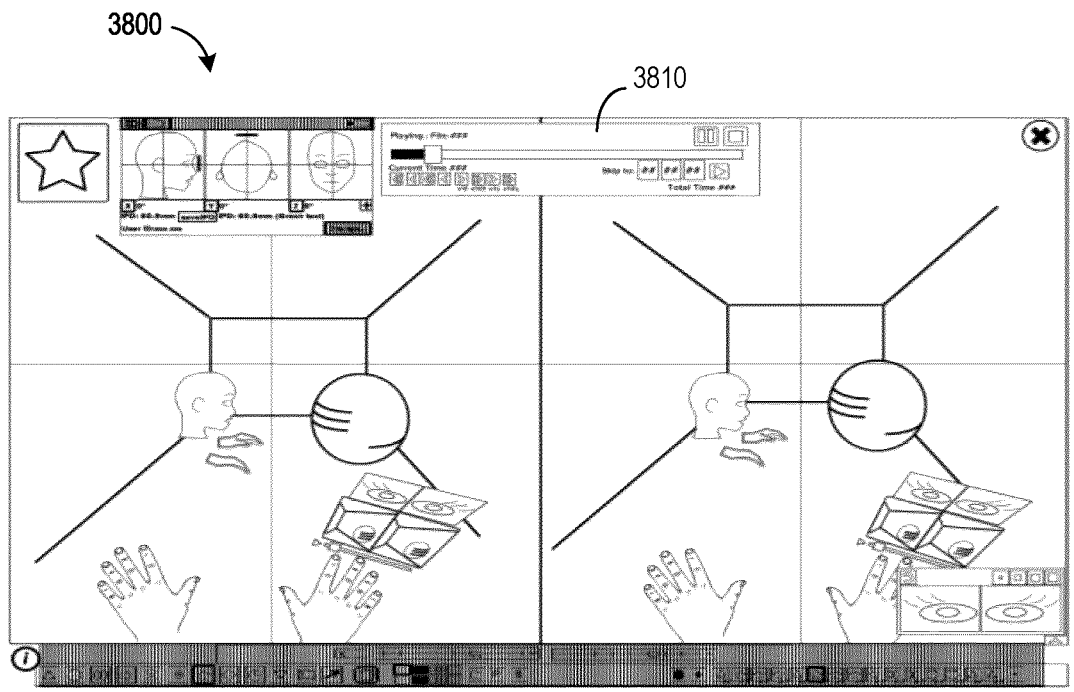
FIG. 38 shows a computer screen image of an example embodiment of a playback mode user interface.

Referring now to FIG. 38, shown therein is a computer screen image of an example embodiment of a playback mode user interface 3800 of VR test creation interface 400. During playback, a playback mode control window 3810 may appear (e.g., to the right of the subject data area 510). Playback files may be accessed by the file dialogue box provided by the operating system. If a file is a .rec file, it may prompt the open file for playback dialogue, indicating the filename and duration of the chosen file.

Figure 39:
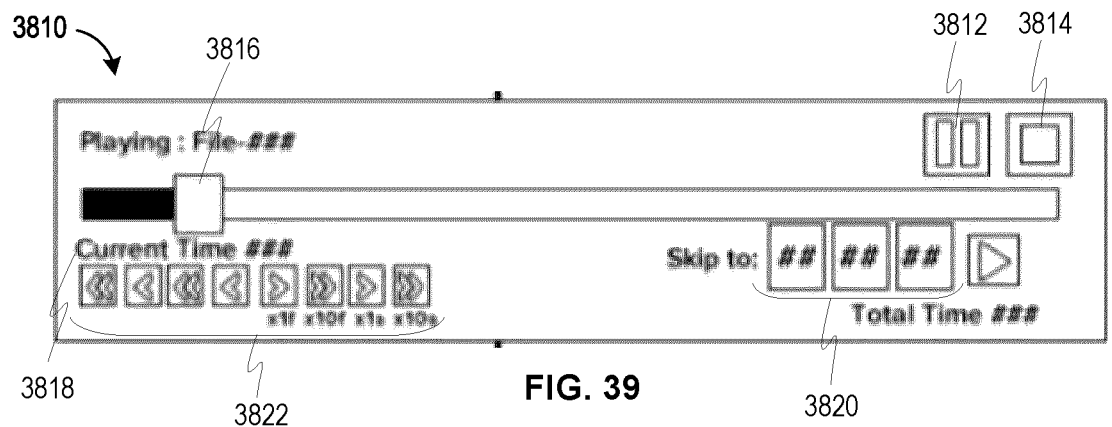
FIGS. 39 and 40 show examples of playback mode control windows in play normally and pause modes, respectively.
Figure 40:
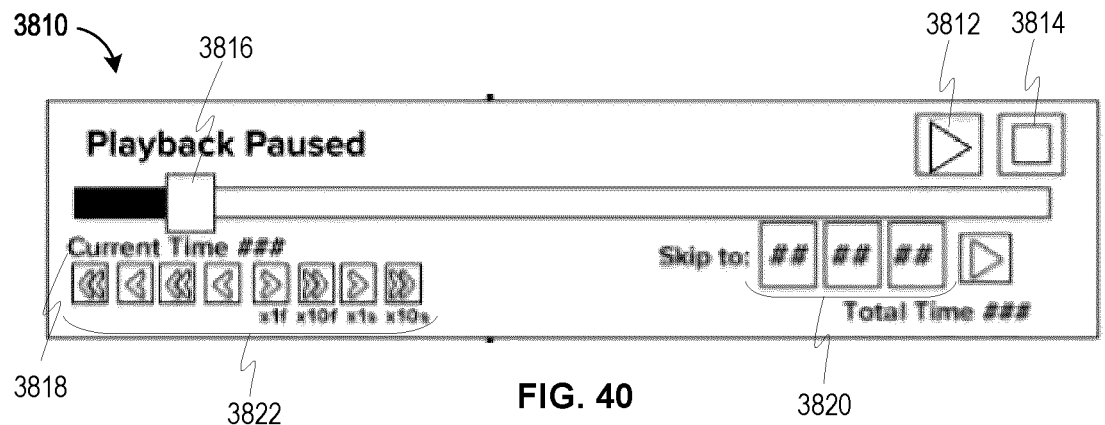

The playback mode control window 3810 may have a variety of modes such as, but not limited to, at least one of fast reverse, play in reverse, step back continuously, step back once, step forward once, step forward continuously, play normally, and fast forward, as well as pause, stop, and seek to a specific time. FIG. 39 shows the playback mode control window 3810 in play normally mode. FIG. 40 shows the playback mode control window 3810 in pause mode.

In the playback mode control window 3810, there may be one or more of:

(A) A pause/play button 3812, which toggles between pausing and playing.
(B) A stop playback and exit playback mode button 3814.
(C) A playback head button 3816, whose position relative to the long background rectangle it appears in front of shows the current relative time compared to the overall duration of the file. Clicking and dragging this button may affect the current playback time accordingly.
(D) A current time 3818, displayed in minutes:seconds: frames (or other suitable time units).
(E) A seek to input text box 3820. The user may enter minutes, seconds, and frames into these boxes and press the arrow directly to the right of them to seek to the indicated part of the .rec file.
(F) Precision jump buttons 3822. They may function (e.g., from left to right), for example, as follows: go back 10 seconds, go back 1 second, go back 10 frames, go back 1 frame, go forward 1 frame, go forward 10 frames, go forward 1 second, go forward 10 seconds.

In playback mode, all controls except for playback controls may be temporarily disabled during playback. Furthermore, simulated head, eyes, and hand controllers may be altered in real time reflecting the current data in the selected recording file. Non playback related controls may be disabled during playback.

The user may view the recorded data in the VR environment and directly observe the simulated head, eyes, and hand controller movements as they update their position, rotation, and button states, as well as being affected by the settings in the UI.

For example, the user can put the VR headset on and watch the subject's head movement, controller movement, and the VR visual stimulus objectively. The previously recorded subject may be represented by a 3D head and simulated controllers which indicate pressed buttons as well as positions based on their state at the current time index in the recorded data. In addition, color filters that were recorded as "on" may appear as "sunglasses" on the simulated head, with semi-transparent materials approximating the color filter effect (e.g., as opposed to filtering the overall cameras).

In the UI, sliders may move and toggle buttons may change states reflecting current data in the selected recording file. A button in the UI may open a dialogue to choose a file for playback from the subject data folder, and on selection playback may commence. A pause button may be selected by the user to temporarily pause playback. A text box may indicate the current time index. Another text box may indicate the total duration of the current recorded data file. An input text box may enable the user to manually enter a time index to jump to. A button next to the input text box may exist which, when selected, moves the time index to the indicated value. A slider may, when dragged back and forth by the user, jump to the relative time index as a percent of the entire length of the recording. A stop button, when selected by the user, stops playback, hides playback controls, and returns the user interface to non-playback mode, at which time all UI controls will become interactable again. One or more (e.g., six) precision seek buttons may be used to seek at different rates, with the outside seek buttons moving either forward or backward 10 s, the next inner seek buttons 1 s, the next inner seek buttons 10 frames, and the innermost seek buttons 1 frame.

Playback controls may also be selected through the VR controllers. For example, slider scrubbing may be accessible by the controller thumb pad or stick as it is with the UI settings sliders. The controller grip or alt buttons may be used to select play/pause playback. The trigger may be used to interact with a playback UI in VR that resembles the one in the main desktop UI. When the controller collides with a given VR UI element, the user may pull the controller trigger to activate it like a mouse click does on the desktop UI. For example, in playback mode, the user can see the original representation of the recorded subject, but with the user being a separate entity in VR, such that the user may enter the VR environment and look at the subject as the subject is being tested. The user may have various actions that they can perform in this mode, such as at least one of looking down at their controllers, seeing a UI that shows the view from the recorded subject's eye view, seeing a video of the subject's eyes, and being able to interact with a play/pause/timeline using another controller.

Figure 41:
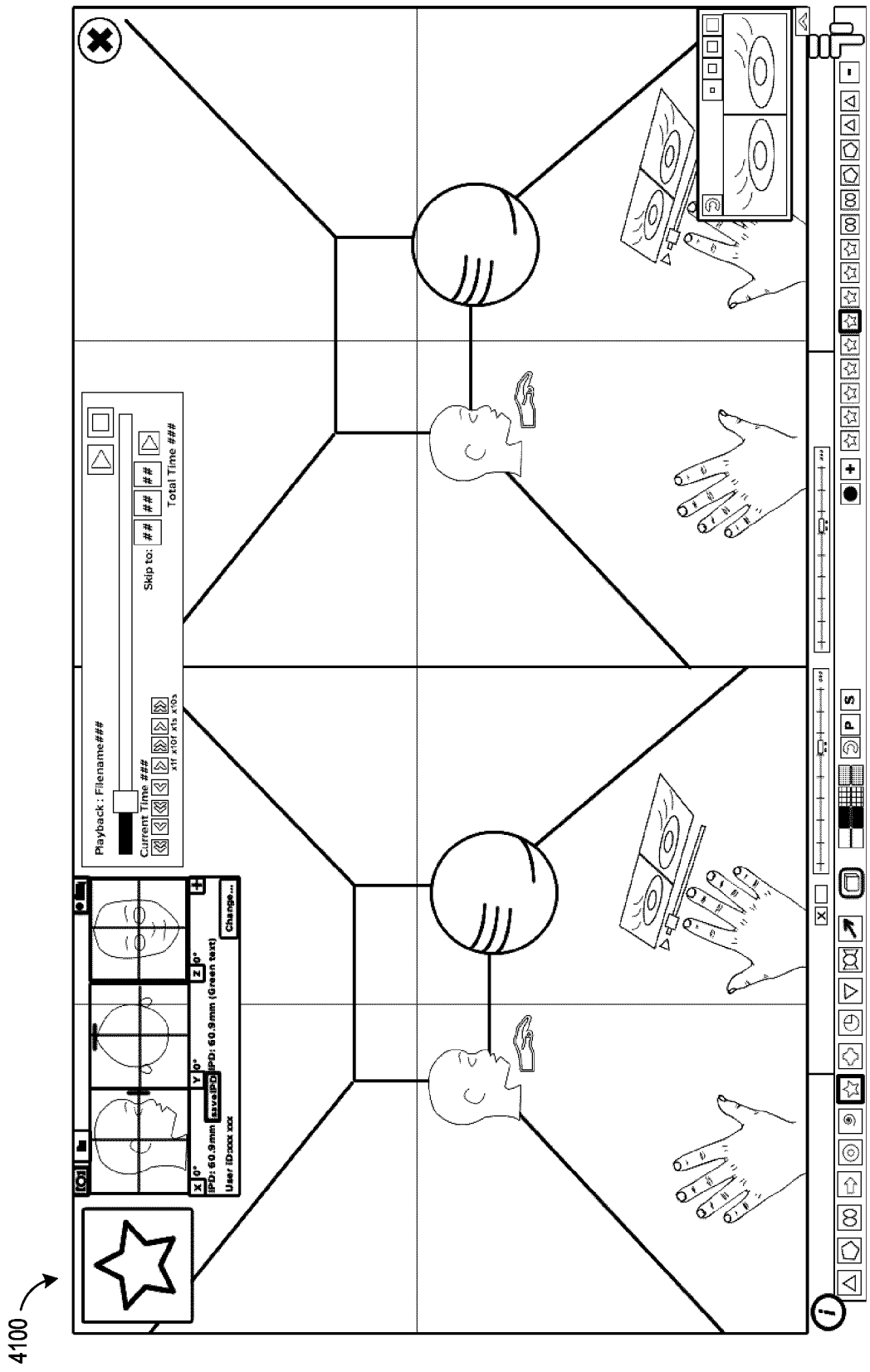
FIG. 41 shows a computer screen image of an example embodiment of a playback in VR view.

Referring now to FIG. 41, shown therein is a computer screen image of an example embodiment of a playback in VR view 4100 of VR test creation interface 400. The user may enter playback in VR view 4100, for example, by pressing on the pause/play button 3812 while wearing a VR headset. The VR test creation interface 400 may cause the VR headset to provide, for example, a VR version of the playback mode user interface 3800, a VR version of the playback mode user interface 3800 with some features hidden and/or additional features shown, the same view as experienced by the subject, or a combination thereof. The VR headset may thereby provide, for example, eye videos, perspectives of the subject's view, playhead pause/play status, time position, and time elapsed displayed as attached to the VR controller.

In at least one embodiment, when a file is being played back, the VR test creation interface 400 shows the perspective of the subject right above the VR controller and also shows playhead position, as well as the eye videos if they are available. This may advantageously contribute to displaying test data during playback to a clinician while they themselves are in VR.

Referring now to FIG. 42, shown therein is a flow chart of an example embodiment of a method 4200 of creating and updating a protocol. Method 4200 may be carried out, for example, by some or all of system 100. Method 4200 may be implemented, for example, on some or all of computer 140.

Broadly speaking, some or all of method 4200 may be used to create a protocol while in protocol authoring mode (e.g., using the protocol selection & authoring area 570). For example, to create a protocol, method 4200 includes: providing a plurality of visual objects (at 4232); providing one or more subject environments (at 4232); receiving one or more first inputs relating to a selection of the plurality of visual user interface objects (at 4234, 4236, 4238); for each of the one or more first inputs, receiving one or more second inputs relating to a functionality of the selection of the one or more first inputs (at 4234, 4236, 4238); generating measurement instructions to obtain one or more subject measurements from one or more sensors, based at least on the one or more first inputs and the one or more second inputs (at 4242); and generating the protocol based at least on the one or more first inputs, the one or more second inputs, and the measurement instructions (at 4244).

At 4212, the VR test application 160 is executed by the computer 140.

At 4214, the computer 140 prompts the user for a Subject ID. The computer 140 may confirm the entry of a Subject ID or skip entry at the option of the user.

At 4216, the computer 140 receives input from the user to enter protocol authoring mode (e.g., by selecting or pressing on 'A').

At 4218, the computer 140 receives input from the user to read an existing protocol. The existing protocol may be selected from a series of protocols. However, the user may skip this step when creating a new protocol, for example.

At 4220, the computer 140 receives input from the user to create a new protocol or update an existing protocol.

At 4222, the computer 140 determines whether the user has decided to create a new protocol or update an existing protocol based on the user input. If the user decision is to create (C), then the method proceeds to 4224. If the user decision is to update (U), the method proceeds to 4228.

At 4224, the computer 140 receives input from the user to select an existing protocol. The user may do so, for example, by selecting a test icon corresponding to an existing protocol.

At 4226, the computer 140 receives input from the user to add a protocol based on an existing protocol (e.g., an existing test). The user may do so, for example, by pressing a plus (i.e., '+') icon. For example, pressing plus while another protocol is selected causes a new protocol to be created that starts as a copy of the previously selected protocol, and can be edited from that point.

At 4228, the computer 140 receives input from the user to select an existing protocol for updating. The user may then update certain settings for the selected protocol. The computer 140 receives these updated settings and inputs them in a modified file for this updated protocol.

At 4230, the computer 140 receives input to confirm save. The user may do so, for example, by clicking on 'Y'. The computer 140 then saves the modified file for the modified protocol. When the VR test application 160 is exited and returned to, the new protocol will appear.

At 4232, the computer 140 displays a new protocol matching the previously selected icon. The new protocol may be highlighted. If the new protocol is not highlighted, the user may click the new protocol to highlight it.

At 4234, the computer 140 receives input from the user to adjust the settings of the protocol using test-specific controls. For example, in a given test, distance/rotation sliders may be available, in which case the user may enter a number of degrees or meters (or other suitable unit) to specify an orientation and/or distance for a VR stimulus from the subject's eyes in VR. In another example, color filters may be available, in which case, a toggle (e.g., 0/1, on/off) may be stored to correspond with the toggle button. In another example, hiding or showing certain aspects of a stimulus may be available, in which case, toggles may be used to turn a stimulus on or off. All settings programmed as available may be recorded in a protocol in the position they are in at the time a local record button is pressed.

At 4236, the computer 140 receives input from the user to choose a background and/or floor type for the VR environment during the VR test. The default may be no background or floor, for example.

At 4238, the computer 140 receives input from the user to alter the stimulus orientation settings. The user may input the settings using, for example, the test stimulus settings window 3000. When a given setting is locked and the local record button is pressed, the state of the lock (i.e., locked or unlocked) may be stored in the currently selected preset for saving.

At 4240, the computer 140 receives input from the user to locally record the protocol. The user may do so, for example, by selecting a button with a red circle (or the letters "REC") on it.

At 4242, the computer 140 receives input from the user to select another protocol then select the new protocol to ensure the settings change to what is indicated by the protocol. For example, when the user input is to select a protocol, the computer 140 updates the currently displayed settings to match the selected protocol settings.

At 4244, the computer 140 receives input from the user to save all protocols to an external protocol file, which may be stored, for example, in the data files 168. The computer 140 may prompt the user to confirm save.

In at least one embodiment, method 4200 includes additional steps related to deleting an existing protocol. For example, the computer 140 may receive input from the user to delete a protocol, such as when the user selects a minus ('−') button on the user interface. The computer 140 may display a popup window in that case, which will allow the user to confirm deletion, for example, by selecting a yes ('Y') button. The user may make the deletion permanent, for example, by carrying out act 4244.

In accordance with the teachings herein, the example embodiments that are described provide technical solutions to one or more technical problems. For example, test stimuli for vision tests often need to be precise and a consistent distance away from a subject, which may be difficult in real life due to various physical barriers and human error. However, with VR visual testing, lighting is more controllable so that it is consistent and precise from test to test, such that location, color, shadows, and glare are not issues. Furthermore, test equipment in real life can wear and get damaged, which decreases its precision. However, in a VR environment, the VR stimulus, being virtual, does not wear out or become dirty/scratched. With VR visual testing, the tests may also be fully recordable, with biometric data obtained in real time, such that it can be saved for later analysis (e.g., at up to 90 samples per second). The data may also be non-person identifiable as it can be entirely telemetry based. Users may view the data in VR so as to provide the closest thing to being with the patient when they are being analyzed while maintaining patient privacy.

The example embodiments that are described may provide additional advantages over real-life visual testing. For example, prisms and color filters are cumbersome to mount or hold in front of a subject as they turn their eyes and can simply not practically be used with certain equipment like the Bagolini or Lees test. However, with VR visual testing, it is possible to apply prismatic/torsional rotation, displacement, color filter, blurring, or occlusion consistently and easily to any VR visual stimulus. In another aspect, torsional rotation of a visual stimulus in physical reality is currently impossible outside of the Synoptophore; whereas in VR, it can be applied to all vision tests.

Test-specific advantages are also particularly noticeable with the Frisby Stereopsis test, which suffers in physical reality from movement of the visual stimulus (e.g., a human holding the device, where even the slightest movement can spoil the test). In a VR environment, the visual stimuli can be positioned perfectly still relative to the subject's head. The Synoptophore machine can be entirely replaced with VR software such that there are no worn out, faded slides, and in VR the visual field is much wider, which allows for the subject's eyes to be more clearly monitored and tracked during the entire test. In physical reality the stimulus used with the Synoptophore is limited while with VR visual testing, a VR laser pointer can be used by the user to point at specific parts of the VR stimulus to help direct the subject's glance. The Lees test also has many advantages in VR, particularly that the stimulus distance in VR can be varied, whereas in physical tests the VR stimulus cannot move. With VR visual testing, it is also possible to measure torsional alignment, which is currently either cumbersome or impossible in physical reality.

It should be understood that the various user interfaces may have a different appearance in alternative embodiments. Furthermore, in other embodiments some of the VR vision tests described herein are not provided by the system 100 while in other embodiments more VR vision tests can be implemented in the system 100. For example, the system 100 may be provided with other VR tests that implement other existing gold-standard tests.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A method of updating a protocol for a Virtual Reality (VR) medical test via a user device having at least one processor, the VR medical test being performed on a subject via a VR device worn by the subject, wherein the method is performed by the at least one processor and the method comprises:
   displaying GUI elements associated with the protocol on the user device, the GUI elements having user adjustable settings for modifying a functioning of the VR medical test;
   receiving at least one selection input from the user device corresponding to a selection of at least one of the GUI elements;
   receiving at least one setting input from the user device that corresponds to the selection of the at least one selected GUI elements;
   modifying the user adjustable setting for each of the at least one selected GUI elements according to the corresponding at least one setting input; and
   updating the protocol based at least on the user adjustable setting for each of the at least one selected GUI elements and a plurality of operations associated with the VR device.

2. The method of claim 1, wherein the method further comprises determining at least one of the plurality of operations to be executed on the VR device during the VR medical test based at least in part on the at least one selection input and the at least one setting input.

3. The method of claim 1, wherein the VR medical test is a VR vision test.

4. The method of claim 1, wherein the GUI elements comprise at least one of one or more VR methods, one or more VR features, or one or more VR controls.

5. The method of claim 4, wherein the one or more VR methods comprise at least one of: left eye tracking, right eye tracking, head rotation tracking, or laser pointer placement.

6. The method of claim 4, wherein the one or more VR features comprise at least one of: a subject data area, a subject VR view, or an eye camera area.

7. The method of claim 4, wherein the one or more VR controls comprise at least one of: at least one state button, at least one toggle button, at least one slider, and at least one VR controller icon.

8. The method of claim 3, wherein determining at least one of the plurality of operations comprises organizing a VR visual stimulus including determining an intensity, one or more colors, and one or more shapes of at least one object in the VR visual stimulus.

9. The method of claim 3, wherein determining at least one of the plurality of operations comprises filtering a visual stimulus with specific wavelengths of color at varying intensities to obtain data from the subject during VR testing relating to color sensitivity.

10. The method of claim 3, wherein determining at least one of the plurality of operations comprises at least one of altering an orientation and/or position of an object in the visual stimulus, and displaying the visual stimulus to one or both eyes of the subject.

11. The method of claim 3, wherein determining at least one of the plurality of operations comprises representing and recording each axis of rotation of the subject's head relative to a direction of presentation of the VR visual stimulus to the subject.

12. The method of claim 3, wherein the at least one of the GUI elements comprises a user controllable setting for allowing the user to set at least one of a distance, an orientation, and an intensity of a visual VR stimulus using the user device.

13. The method of claim 3, wherein the at least one of the GUI elements comprises a sensor control and the user adjustable setting therefor allows the user to select when the sensor is used to obtain measurements of the subject during testing.

14. The method of claim 3, wherein the method further comprises receiving user input for the sensor control for controlling at least one of an eye tracker, a camera, a force feedback sensor, an EEG sensor, and a motion tracker.

15. The method of claim 3, wherein the functionality of the selection comprises at least one of displacement, rotation, or color filtering.

16. The method of claim 1, wherein the method further comprises:

receiving at least one recording input from the user device corresponding to recording instructions associated with recording data during execution of the VR medical test on the VR device.

17. The method of claim 16, wherein the recording instructions comprise at least one of tracking one or both subject eyes, recording a position of the subject's head, recording a rotation of the subject's head, and recording a selection made by the subject through a hand gesture or interaction with a VR controller.

18. The method of claim 3, wherein the VR vision test is a Bagolini Striated Lens VR test and the method further comprises receiving user input to adjust settings for GUI elements associated with a gradations input, a distance input, and a rotation input.

19. The method of claim 3, wherein the VR vision test is a Frisby Stereopsis VR test and the method further comprises receiving user input to adjust settings for GUI elements associated with a stereopsis stimulus selection input and a distance input.

20. The method of claim 3, wherein the VR vision test is a Synoptophore VR test and the method further comprises receiving user input to adjust settings for GUI elements associated with a reverse eye stimulus input, a swap eye stimulus input, an actual stimulus input, and a stimulus distance input.

21. The method of claim 3, wherein the VR vision test is a Lees Screen VR test and the method further comprises receiving user input to adjust settings for GUI elements associated with a show close-up stimulus input, a show distant stimulus input, and a show eye orientation input.

22. A system for allowing a user to update a protocol for a Virtual Reality (VR) medical test to be performed on a subject via a VR device worn by the subject, wherein the system comprises:
 a display that shows a graphical user interface having GUI elements representing settings for the protocol;
 an input device that is adapted to receive user inputs from the user for at least one of the GUI elements;
 a memory unit that is adapted to store a protocol data file for the updated protocol; and
 a processor unit that is operatively coupled to the display, the input device and the memory unit, the processor unit having at least one processor, the memory unit comprising a non-transient computer-readable storage medium having stored thereon computer-executable instructions for execution by the processor unit to perform the method according to claim 1.

23. A non-transitory computer readable medium comprising a plurality of instructions that are executable on a processor of a system for adapting the system to implement a method to allows a user to update a protocol for a Virtual Reality (VR) medical test to be performed on a subject via a VR device worn by the subject, wherein the method is defined according to claim 1.

* * * * *